(12) United States Patent
Froehlich et al.

(10) Patent No.: US 10,465,181 B2
(45) Date of Patent: *Nov. 5, 2019

(54) MUTATIONS IN IRON-SULFUR CLUSTER PROTEINS THAT IMPROVE XYLOSE UTILIZATION

(71) Applicant: LALLEMAND HUNGARY LIQUIDITY MANAGEMENT LLC, Budapest (HU)

(72) Inventors: Allan Froehlich, Hartland, VT (US); Brooks Henningsen, Lebanon, NH (US); Sean Covalla, Thetford Center, VT (US); Rintze M. Zelle, Lebanon, NH (US)

(73) Assignee: Lallemand Hungary Liquidity Management LLC, Budapest (HU)

( * ) Notice: Subject to any disclaimer, the term of this patent is extended or adjusted under 35 U.S.C. 154(b) by 30 days.

This patent is subject to a terminal disclaimer.

(21) Appl. No.: 15/884,449

(22) Filed: Jan. 31, 2018

(65) Prior Publication Data

US 2018/0251750 A1   Sep. 6, 2018

Related U.S. Application Data

(63) Continuation of application No. 14/821,955, filed on Aug. 10, 2015, now Pat. No. 9,920,312.

(60) Provisional application No. 62/035,748, filed on Aug. 11, 2014.

(51) Int. Cl.
*C12N 9/92* (2006.01)
*C07K 14/395* (2006.01)
*C12P 7/06* (2006.01)

(52) U.S. Cl.
CPC .............. *C12N 9/92* (2013.01); *C07K 14/395* (2013.01); *C12P 7/06* (2013.01); *C12Y 503/01005* (2013.01); *Y02E 50/17* (2013.01)

(58) Field of Classification Search
None
See application file for complete search history.

(56) References Cited

FOREIGN PATENT DOCUMENTS

WO   WO 2012/071121   *   5/2012   .............. C12N 1/00

* cited by examiner

*Primary Examiner* — Suzanne M Noakes
*Assistant Examiner* — Jae W Lee
(74) *Attorney, Agent, or Firm* — Nutter McClennen & Fish LLP

(57) ABSTRACT

There is provided an engineered host cells comprising (a) one or more mutations in one or more endogenous genes encoding a protein associated with iron metabolism; and (b) at least one gene encoding a polypeptide having xylose isomerase activity, and methods of their use thereof.

Figure 1:
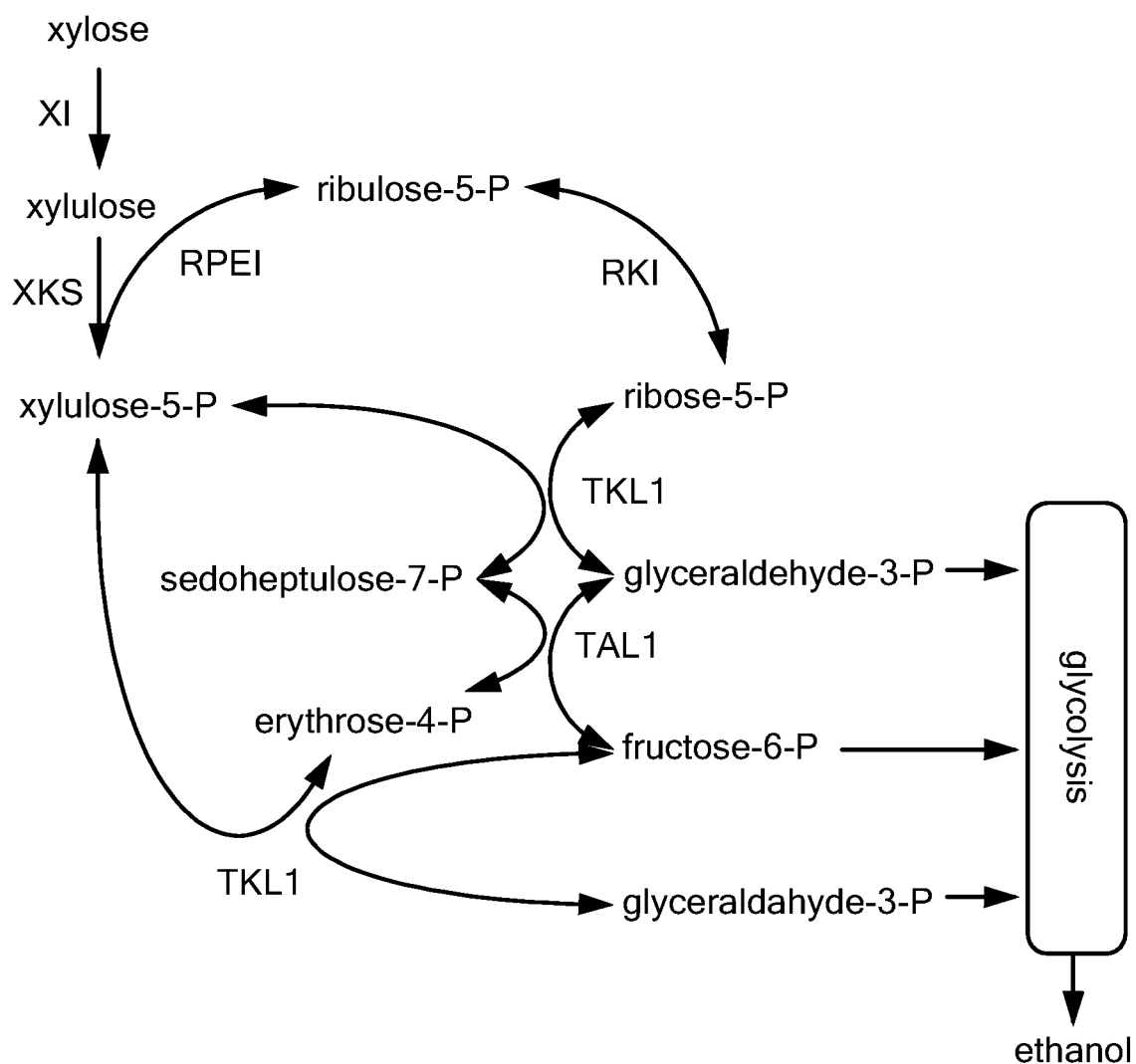

21 Claims, 10 Drawing Sheets
Specification includes a Sequence Listing.

Schematic representation of xylose fermentation in genetically engineered *S. cerevisiae*

Figure 5: Growth rates of yeast cells heterologously expressing selected XIs with and without a mutation in *YFH1*
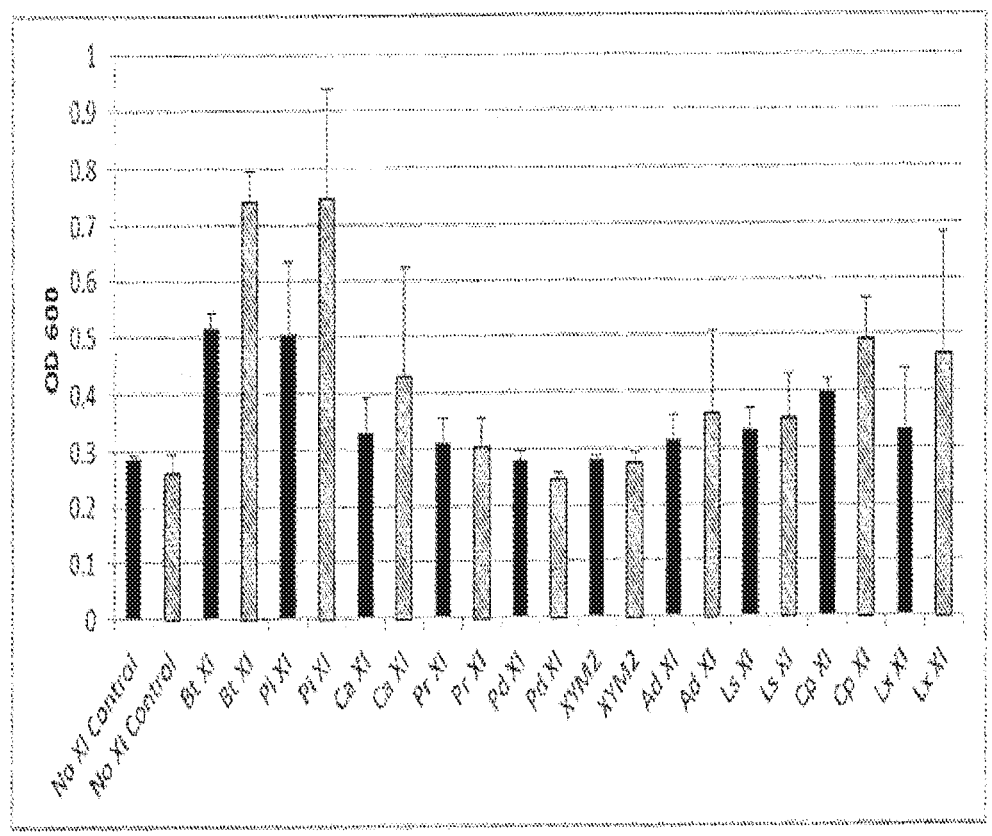

SEQUENCE LISTING

```
<160> NUMBER OF SEQ ID NOS: 42

<210> SEQ ID NO 1
<211> LENGTH: 436
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Chimeric Xylose Isomerase 1

<400> SEQUENCE: 1

Met Ser Glu Leu Phe Gln Asn Ile Pro Lys Ile Lys Tyr Glu Gly Ala
```

-continued

```
  1               5                  10                 15
Asn Ser Lys Asn Pro Leu Ala Phe His Tyr Tyr Asp Ala Glu Lys Glu
             20                 25                 30
Ile Met Gly Lys Lys Met Lys Asp Trp Leu Arg Phe Ala Met Ala Trp
             35                 40                 45
Trp His Thr Leu Cys Ala Glu Gly Ser Asp Gln Phe Gly Pro Gly Thr
             50                 55                 60
Lys Thr Phe Pro Trp Asn Glu Gly Thr Asp Pro Ile Glu Lys Ala Lys
65                  70                 75                 80
Gln Lys Val Asp Ala Gly Phe Glu Ile Met Thr Lys Leu Gly Ile Glu
             85                 90                 95
His Tyr Cys Phe His Asp Val Asp Leu Val Asp Glu Gly Lys Asn Val
             100                105                110
Glu Glu Tyr Glu Lys Asn Leu Lys Thr Ile Val Ala Tyr Leu Lys Glu
             115                120                125
Lys Gln Lys Glu Thr Gly Ile Lys Leu Leu Trp Gly Thr Ala Asn Val
             130                135                140
Phe Gly His Ala Arg Tyr Met Asn Gly Ala Ala Thr Asn Pro Asp Phe
145                 150                155                160
Asp Val Val Ala Arg Ala Ala Val Gln Ile Lys Asn Ala Ile Asp Ala
             165                170                175
Thr Ile Glu Leu Gly Gly Glu Asn Tyr Val Phe Trp Gly Gly Arg Glu
             180                185                190
Gly Tyr Met Ser Leu Leu Asn Thr Asn Met Lys Arg Glu Lys Asp His
             195                200                205
Leu Ala Met Met Leu Thr Met Ala Arg Asp Tyr Gly Arg Lys Asn Gly
             210                215                220
Phe Lys Gly Thr Phe Leu Ile Glu Pro Lys Pro Met Glu Pro Thr Lys
225                 230                235                240
His Gln Tyr Asp Val Asp Ser Glu Thr Val Ile Gly Phe Leu Arg His
             245                250                255
Tyr Gly Leu Asp Lys Asp Phe Ala Leu Asn Ile Glu Val Asn His Ala
             260                265                270
Thr Leu Ala Gly His Thr Phe Glu His Glu Leu Gln Ala Ala Ala Asp
             275                280                285
Ala Gly Met Leu Cys Ser Ile Asp Ala Asn Arg Gly Asp Tyr Gln Asn
             290                295                300
Gly Trp Asp Thr Asp Gln Phe Pro Met Asp Ile Tyr Glu Leu Ala Gln
305                 310                315                320
Ala Trp Leu Val Ile Leu Glu Gly Gly Gly Leu Thr Thr Gly Gly Thr
             325                330                335
Asn Phe Asp Ala Lys Thr Arg Arg Asn Ser Thr Asp Leu Glu Asp Ile
             340                345                350
Phe Ile Ala His Ile Gly Gly Met Asp Ala Phe Ala Arg Ala Leu Met
             355                360                365
Ile Ala Ala Asp Ile Leu Glu Asn Ser Asp Tyr Arg Lys Met Arg Ala
             370                375                380
Glu Arg Tyr Ala Ser Phe Asp Ala Gly Glu Gly Lys Ala Phe Glu Asp
385                 390                395                400
Gly Lys Leu Thr Leu Glu Asp Leu Arg Thr Ile Ala Leu Arg Asp Gly
             405                410                415
Glu Pro Lys Gln Ile Ser Gly Lys Gln Glu Leu Tyr Glu Met Ile Val
             420                425                430
```

Asn Leu His Ile
    435

<210> SEQ ID NO 2
<211> LENGTH: 1311
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Chimeric Xylose Isomerase 1

<400> SEQUENCE: 2

```
atgtctgaat tgttccaaaa catcccaaag atcaagtacg aaggtgctaa ctctaagaac      60
ccattggctt tccactacta cgacgctgaa aaggaaatca tgggtaagaa gatgaaggac     120
tggttgagat cgctatggc ttggtggcac actttgtgtg ctgaaggttc tgaccaattc     180
ggtccaggta ctaagacttt cccatggaac gaaggtactg acccaatcga aaaggctaag     240
caaaaggttg acgctggttt cgaaatcatg actaagttgg gtatcgaaca ctactgtttc     300
cacgacgttg acttggttga cgaaggtaag aacgttgaag aatacgaaaa gaacttgaag     360
actatcgttg cttacttgaa ggaaaagcaa aaggaaactg gtatcaagtt gttgtggggt     420
actgctaacg ttttcggtca cgctagatac atgaacggtg ctgctactaa cccagacttc     480
gacgttgttg ccagagctgc tgttcaaatt aagaacgcta ttgacgctac tattgaattg     540
ggtggtgaaa actacgtttt ctggggtggt agagaaggtt acatgtcttt gttgaacacc     600
aacatgaaga gagaaaagga tcatttggcc atgatgttga ctatggctag agattacggt     660
agaaagaatg gttcaaggg tactttcttg atcgaaccta aacctatgga acctactaag     720
caccaatacg atgttgattc cgaaaccgtt atcggtttct tgagacatta cggtttggat     780
aaggatttcg ccttgaacat cgaagttaac catgctactt tggctggtca tactttcgaa     840
catgaattgc aagctgctgc tgatgctggt atgttgtgtt ctattgatgc taacagaggt     900
gactaccaaa atggttggga tactgatcaa ttcccaatgg atatctacga attggctcaa     960
gcttggttgg ttattttgga aggtggtggt ttgactactg tggtactaa ttttgatgcc    1020
aagaccagaa gaaactccac tgatttggaa gacatcttca ttgcccatat cggtggtatg    1080
gatgcttttg ctagagcttt gatgattgct gccgatattt ggaaaactc cgactacaga    1140
aagatgagag ctgaaagata cgcttctttt gatgctggtg aaggtaaggc tttcgaagat    1200
ggtaaattga ccttggaaga tttgagaacc attgctttga gagatggtga acctaagcaa    1260
atttccggta agcaagaatt atacgaaatg atcgtcaact gcacatcta a             1311
```

<210> SEQ ID NO 3
<211> LENGTH: 438
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Chimeric Xylose Isomerase 2

<400> SEQUENCE: 3

Met Ala Lys Glu Tyr Phe Pro Phe Thr Gly Lys Ile Pro Phe Glu Gly
1               5                  10                  15

Lys Asp Ser Lys Asn Val Met Ala Phe His Tyr Tyr Glu Pro Glu Lys
            20                  25                  30

```
Val Val Met Gly Lys Lys Met Lys Asp Trp Leu Lys Phe Ala Met Ala
         35              40              45
Trp Trp His Thr Leu Gly Gly Ala Ser Ala Asp Gln Phe Gly Gly Gln
         50              55              60
Thr Arg Ser Tyr Glu Trp Asp Lys Ala Ala Asp Ala Val Gln Arg Ala
65              70              75              80
Lys Asp Lys Met Asp Ala Gly Phe Glu Ile Met Asp Lys Leu Gly Ile
                 85              90              95
Glu Tyr Phe Cys Phe His Asp Val Asp Leu Val Glu Glu Gly Glu Thr
                100             105             110
Ile Ala Glu Tyr Glu Arg Arg Met Lys Glu Ile Thr Asp Tyr Ala Leu
             115             120             125
Val Lys Met Lys Glu Tyr Pro Asn Ile Lys Leu Leu Trp Gly Thr Ala
         130             135             140
Asn Val Phe Gly His Ala Arg Tyr Met Asn Gly Ala Ala Thr Asn Pro
145             150             155             160
Asp Phe Asp Val Val Ala Arg Ala Ala Val Gln Ile Lys Asn Ala Ile
                165             170             175
Asp Ala Thr Ile Glu Leu Gly Gly Glu Asn Tyr Val Phe Trp Gly Gly
             180             185             190
Arg Glu Gly Tyr Met Ser Leu Leu Asn Thr Asn Met Lys Arg Glu Lys
         195             200             205
Asp His Leu Ala Met Met Leu Thr Met Ala Arg Asp Tyr Gly Arg Lys
         210             215             220
Asn Gly Phe Lys Gly Thr Phe Leu Ile Glu Pro Lys Pro Met Glu Pro
225             230             235             240
Thr Lys His Gln Tyr Asp Val Asp Ser Glu Thr Val Ile Gly Phe Leu
             245             250             255
Arg His Tyr Gly Leu Asp Lys Asp Phe Ala Leu Asn Ile Glu Val Asn
             260             265             270
His Ala Thr Leu Ala Gly His Thr Phe Glu His Glu Leu Gln Ala Ala
         275             280             285
Ala Asp Ala Gly Met Leu Cys Ser Ile Asp Ala Asn Arg Gly Asp Tyr
         290             295             300
Gln Asn Gly Trp Asp Thr Asp Gln Phe Pro Met Asp Ile Tyr Glu Leu
305             310             315             320
Ala Gln Ala Trp Leu Val Ile Leu Glu Gly Gly Leu Thr Thr Gly
             325             330             335
Gly Thr Asn Phe Asp Ala Lys Thr Arg Arg Asn Ser Thr Asp Leu Glu
             340             345             350
Asp Ile Phe Ile Ala His Ile Gly Gly Met Asp Ala Phe Ala Arg Ala
             355             360             365
Leu Met Ile Ala Ala Asp Ile Leu Glu Asn Ser Asp Tyr Arg Lys Met
         370             375             380
Arg Ala Glu Arg Tyr Ala Ser Phe Asp Ala Gly Glu Gly Lys Ala Phe
385             390             395             400
Glu Asp Gly Lys Leu Thr Leu Glu Asp Leu Arg Thr Ile Ala Leu Arg
                405             410             415
Asp Gly Glu Pro Lys Gln Ile Ser Gly Lys Gln Glu Leu Tyr Glu Met
             420             425             430
Ile Val Asn Leu His Ile
             435
```

<210> SEQ ID NO 4
<211> LENGTH: 1317
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Chimeric Xylose Isomerase 2

<400> SEQUENCE: 4

```
atggctaagg aatacttccc attcactggt aagatcccat tcgaaggtaa ggactctaag      60
aacgttatgg ctttccacta ctacgaacca gaaaaggttg ttatgggtaa gaagatgaag     120
gactggttga agttcgctat ggcttggtgg cacactttgg gtggtgcttc tgctgaccaa     180
ttcggtggtc aaactagatc ttacgaatgg gacaaggctg ctgacgctgt tcaaagagct     240
aaggacaaga tggacgctgg tttcgaaatc atggacaagt ggggtatcga atacttctgt     300
ttccacgacg ttgacttggt tgaagaaggt gaaactatcg ctgaatacga agaagaatg      360
aaggaaatca ctgactacgc tttggttaag atgaaggaat acccaaacat caagttgttg     420
tggggtactg ctaacgtttt cggtcacgct agatacatga cggtgctgc tactaaccca      480
gacttcgacg ttgttgccag agctgctgtt caaattaaga cgctattga cgctactatt      540
gaattgggtg tgaaaacta cgttttctgg ggtggtagag aaggttacat gtctttgttg      600
aacaccaaca tgaagagaga aaaggatcat ttggccatga tgttgactat ggctagagat     660
tacggtagaa agaatggttt caagggtact ttcttgatcg aacctaaacc tatggaacct     720
actaagcacc aatacgatgt tgattccgaa accgttatcg gtttcttgag acattacggt     780
ttggataagg atttcgcctt gaacatcgaa gttaaccatg ctactttggc tggtcatact     840
ttcgaacatg aattgcaagc tgctgctgat gctggtatgt tgtgttctat tgatgctaac     900
agaggtgact accaaaatgg ttgggatact gatcaattcc caatggatat ctacgaattg     960
gctcaagctt ggttggttat tttggaaggt ggtggtttga ctactggtgg tactaatttt    1020
gatgccaaga ccagaagaaa ctccactgat ttggaagaca tcttcattgc ccatatcggt    1080
ggtatggatg cttttgctag agctttgatg attgctgccg atattttgga aaactccgac    1140
tacagaaaga tgagagctga agatacgct tcttttgatg ctggtgaagg taaggctttc    1200
gaagatggta aattgacctt ggaagatttg agaaccattc tttgagaga tggtgaacct    1260
aagcaaattt ccggtaagca agaattatac gaaatgatcg tcaacttgca catctaa      1317
```

<210> SEQ ID NO 5
<211> LENGTH: 437
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Chimeric Xylose Isomerase 3

<400> SEQUENCE: 5

Met Val Lys Glu Tyr Phe Pro Ala Ile Gln Lys Ile Lys Phe Glu Gly
1               5                   10                  15

Lys Asp Ser Lys Asn Pro Met Ala Phe His Tyr Tyr Asp Ala Glu Lys
            20                  25                  30

Glu Ile Met Gly Lys Lys Met Lys Asp Trp Leu Arg Phe Ala Met Ala
        35                  40                  45

Trp Trp His Thr Leu Cys Ala Glu Gly Ser Asp Gln Phe Gly Pro Gly
 50                  55                  60

Thr Lys Thr Phe Pro Trp Asn Glu Gly Thr Asp Pro Ile Glu Lys Ala
 65                  70                  75                  80

Lys Gln Lys Val Asp Ala Gly Phe Glu Ile Met Thr Lys Leu Gly Ile
                 85                  90                  95

Glu His Tyr Cys Phe His Asp Val Asp Leu Val Asp Glu Gly Lys Asn
            100                 105                 110

Val Glu Glu Tyr Glu Lys Asn Leu Lys Thr Ile Val Ala Tyr Leu Lys
        115                 120                 125

Glu Lys Gln Lys Glu Thr Gly Ile Lys Leu Leu Trp Ser Thr Ala Asn
130                 135                 140

Val Phe Gly His Lys Arg Tyr Met Asn Gly Ala Ala Thr Asn Pro Tyr
145                 150                 155                 160

Phe Pro Thr Val Ala Cys Val Gly Thr Gln Ile Lys Asn Ala Ile Asp
                165                 170                 175

Ala Cys Ile Ala Leu Gly Gly Gly Asn Tyr Val Phe Trp Gly Gly Arg
            180                 185                 190

Glu Gly Tyr Met Ser Leu Leu Asn Thr Asn Met Lys Arg Glu Lys Asp
        195                 200                 205

His Leu Ala Met Met Leu Thr Met Ala Arg Asp Tyr Gly Arg Lys Asn
210                 215                 220

Gly Phe Lys Gly Thr Phe Leu Ile Glu Pro Lys Pro Met Glu Pro Thr
225                 230                 235                 240

Lys His Gln Tyr Asp Val Asp Ser Glu Thr Val Ile Gly Phe Leu Arg
                245                 250                 255

His Tyr Gly Leu Asp Lys Asp Phe Ala Leu Asn Ile Glu Val Asn His
            260                 265                 270

Ala Thr Leu Ala Gly His Thr Phe Glu His Glu Leu Gln Ala Ala Ala
        275                 280                 285

Asp Ala Gly Met Leu Cys Ser Ile Asp Ala Asn Arg Gly Asp Tyr Gln
290                 295                 300

Asn Gly Trp Asp Thr Asp Gln Phe Pro Met Asp Ile Tyr Glu Leu Ala
305                 310                 315                 320

Gln Ala Trp Leu Val Ile Leu Glu Gly Gly Leu Thr Thr Gly Gly
                325                 330                 335

Thr Asn Phe Asp Ala Lys Thr Arg Arg Asn Ser Thr Asp Leu Glu Asp
            340                 345                 350

Ile Phe Ile Ala His Ile Gly Gly Met Asp Ala Phe Ala Arg Ala Leu
        355                 360                 365

Met Ile Ala Ala Asp Ile Leu Glu Asn Ser Asp Tyr Arg Lys Met Arg
370                 375                 380

Ala Glu Arg Tyr Ala Ser Phe Asp Ala Gly Glu Gly Lys Ala Phe Glu
385                 390                 395                 400

Asp Gly Lys Leu Thr Leu Glu Asp Leu Arg Thr Ile Ala Leu Arg Asp
                405                 410                 415

Gly Glu Pro Lys Gln Ile Ser Gly Lys Gln Glu Leu Tyr Glu Met Ile
            420                 425                 430

Val Asn Leu His Ile
        435

<210> SEQ ID NO 6
<211> LENGTH: 1314
<212> TYPE: DNA

<210> SEQ ID NO 7
<211> LENGTH: 438
<212> TYPE: PRT
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Chimeric Xylose Isomerase 3

<400> SEQUENCE: 6

```
atggttaagg aatacttccc agctatccaa aagatcaagt tcgaaggtaa ggactctaag      60
aacccaatgg ctttccacta ctacgacgct gaaaaggaaa tcatgggtaa agaagatgaag    120
gactggttga gattcgctat ggcttggtgg cacactttgt gtgctgaagg ttctgaccaa    180
ttcggtccag gtactaagac tttcccatgg aacgaaggta ctgacccaat cgaaaaggct    240
aagcaaaagg ttgacgctgg tttcgaaatc atgactaagt gggtatcga acactactgt    300
ttccacgacg ttgacttggt tgacgaaggt aagaacgttg aagaatacga aaagaacttg    360
aagactatcg ttgcttactt gaaggaaaag caaaaggaaa ctggtatcaa gttgttgtgg    420
tctactgcta acgttttcgg tcacaagaga tatatgaacg gtgctgctac taatccatac    480
tttccaactg ttgcttgcgt tggtactcaa atcaagaatg ctattgatgc ttgcattgct    540
ttgggtggtg aaaattatgt tttctggggt ggtagagaag gttacatgtc tttgttgaac    600
accaacatga agagagaaaa ggatcatttg gccatgatgt tgactatggc tagagattac    660
ggtagaaaga atggtttcaa gggtactttc ttgatcgaac taaacctat ggaacctact    720
aagcaccaat acgatgttga ttccgaaacc gttatcggtt tcttgagaca ttacggtttg    780
gataaggatt tcgccttgaa catcgaagtt aaccatgcta cttttggctgg tcatactttc    840
gaacatgaat tgcaagctgc tgctgatgct ggtatgttgt gttctattga tgctaacaga    900
ggtgactacc aaaatggttg ggatactgat caattcccaa tggatatcta cgaattggct    960
caagcttggt tggttatttt ggaaggtggt ggtttgacta ctggtggtac taattttgat   1020
gccaagacca aagaaactc cactgatttg aagacatct tcattgccca tatcggtggt   1080
atggatgctt tgctagagc tttgatgatt gctgccgata ttttggaaaa ctccgactac   1140
agaaagatga gagctgaaag atacgcttct tttgatgctg gtgaaggtaa ggctttcgaa   1200
gatggtaaat tgaccttgga agatttgaga accattgctt tgagagatgg tgaacctaag   1260
caaatttccg gtaagcaaga attatacgaa atgatcgtca acttgcacat ctaa          1314
```

<210> SEQ ID NO 7
<211> LENGTH: 438
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Directed Chimeric Xylose Isomerase 1

<400> SEQUENCE: 7

```
Met Ala Lys Glu Tyr Phe Pro Phe Thr Gly Lys Ile Pro Phe Glu Gly
1               5                   10                  15

Lys Asp Ser Lys Asn Val Met Ala Phe His Tyr Tyr Glu Pro Glu Lys
            20                  25                  30

Val Val Met Gly Lys Lys Met Lys Asp Trp Leu Lys Phe Ala Met Ala
        35                  40                  45

Trp Trp His Thr Leu Gly Gly Ala Ser Ala Asp Gln Phe Gly Gly Gln
    50                  55                  60

Thr Arg Ser Tyr Glu Trp Asp Lys Ala Ala Asp Ala Val Gln Arg Ala
```

```
                65                  70                  75                  80
Lys Asp Lys Met Asp Ala Gly Phe Glu Ile Met Asp Lys Leu Gly Ile
                    85                  90                  95

Glu Tyr Phe Cys Phe His Asp Val Asp Leu Val Glu Gly Glu Thr
                100                 105                 110

Ile Ala Glu Tyr Glu Arg Arg Met Lys Glu Ile Thr Asp Tyr Ala Leu
                115                 120                 125

Val Lys Met Lys Glu Tyr Pro Asn Ile Lys Leu Leu Trp Gly Thr Ala
            130                 135                 140

Asn Val Phe Gly Asn Lys Arg Tyr Ala Asn Gly Ala Ser Thr Asn Pro
145                 150                 155                 160

Asp Phe Asp Val Val Ala Arg Ala Ile Val Gln Ile Lys Asn Ala Ile
                165                 170                 175

Asp Ala Thr Ile Lys Leu Gly Gly Thr Asn Tyr Val Phe Trp Gly Gly
                180                 185                 190

Arg Glu Gly Tyr Met Thr Leu Leu Asn Thr Asp Met Lys Arg Glu Gln
                195                 200                 205

Glu His Leu Ala Arg Phe Leu Thr Met Ala Lys Asp Tyr Ala Arg Lys
            210                 215                 220

Gln Gly Phe Thr Gly Thr Phe Phe Ile Glu Pro Lys Pro Cys Glu Pro
225                 230                 235                 240

Thr Lys His Gln Tyr Asp Tyr Asp Ala Ala Thr Val Ile Gly Phe Leu
                245                 250                 255

Arg His Phe Gly Leu Asp Lys Asp Phe Lys Leu Asn Leu Glu Val Asn
                260                 265                 270

His Ala Thr Leu Ala Gly His Thr Phe Glu His Glu Leu Ala Cys Ala
            275                 280                 285

Val Asp Ala Gly Met Leu Gly Ser Ile Asp Ala Asn Arg Gly Asp Tyr
            290                 295                 300

Gln Asn Gly Trp Asp Thr Asp Gln Phe Pro Ile Asp Gln Tyr Glu Leu
305                 310                 315                 320

Val Gln Ala Trp Met Glu Ile Ile Arg Gly Gly Phe Thr Thr Gly
                325                 330                 335

Gly Thr Asn Phe Asp Ala Lys Thr Arg Arg Asn Ser Thr Asp Leu Glu
                340                 345                 350

Asp Ile Ile Ile Ala His Ile Ser Gly Met Asp Ala Met Ala Arg Ala
            355                 360                 365

Leu Glu Asn Ala Ala Lys Leu Leu Thr Glu Ser Pro Tyr Lys Lys Met
            370                 375                 380

Lys Ala Asp Arg Tyr Ala Ser Phe Asp Ser Gly Met Gly Lys Asp Phe
385                 390                 395                 400

Glu Asp Gly Lys Leu Thr Phe Glu Gln Val Tyr Glu Tyr Gly Lys Lys
                405                 410                 415

Val Asn Glu Pro Lys Gln Thr Ser Gly Lys Gln Glu Leu Tyr Glu Ala
                420                 425                 430

Ile Val Ala Met Tyr Met
            435

<210> SEQ ID NO 8
<211> LENGTH: 1317
<212> TYPE: DNA
<213> ORGANISM: Artificial Sequence
<220> FEATURE:
<223> OTHER INFORMATION: Description of Artificial Sequence: Synthetic
      polynucleotide
```

<220> FEATURE:
<223> OTHER INFORMATION: Directed Chimeric Xylose Isomerase 1

<400> SEQUENCE: 8

```
atggctaagg aatacttccc attcactggt aagatcccat tcgaaggtaa ggactctaag      60
aacgttatgg ctttccacta ctacgaacca gaaaaggttg ttatgggtaa gaagatgaag     120
gactggttga agttcgctat ggcttggtgg cacactttgg gtggtgcttc tgctgaccaa     180
ttcggtggtc aaactagatc ttacgaatgg acaaggctg ctgacgctgt tcaaagagct      240
aaggacaaga tggacgctgg tttcgaaatc atggacaagt gggtatcga atacttctgt     300
ttccacgacg ttgacttggt tgaagaaggt gaaactatcg ctgaatacga agaagaatg      360
aaggaaatca ctgactacgc tttggttaag atgaaggaat acccaaacat caagttgttg     420
tggggtactg ctaacgtttt cggtaacaag agatacgcta acggtgcttc tactaaccca     480
gacttcgacg ttgttgctag agctatcgtt caaatcaaga cgctatcga cgctactatc      540
aagttgggtg gtactaacta cgttttctgg ggtggtagag aaggttacat gactttgttg     600
aacaccgaca tgaagagaga caagaacatt tggctagat cttgaccat ggctaaagat       660
tacgctagaa agcaaggttt caccggtact tttttcattg aacctaagcc atgcgaacct     720
accaaacatc aatatgatta cgatgctgcc accgttattg gttttttgag acatttcggt     780
ttggacaagg acttcaagtt gaacttggaa gttaaccatg ctactttggc tggtcacact     840
ttcgaacacg aattggcttg tgctgttgac gctggtatgt tgggttctat cgacgctaac     900
agaggtgact accaaaacgg ttgggacact gaccaattcc caatcgacca atacgaattg     960
gttcaagctt ggatggaaat catcagaggt ggtggtttca ctactggtgg tactaacttc     1020
gacgctaaga ctagaagaaa ctctactgac ttggaagaca tcatcatcgc tcacatctct     1080
ggtatggacg ctatggctag agctttggaa aacgctgcta agttgttgac tgaatctcca     1140
tacaagaaga tgaaggctga cagatacgct tctttcgact ctggtatggg taaggacttc     1200
gaagacggta agttgacttt cgaacaagtt tacgaatacg gtaagaaggt taacgaacca     1260
aagcaaactt ctggtaagca agaattgtac gaagctatcg ttgctatgta catgtga       1317
```

<210> SEQ ID NO 9
<211> LENGTH: 443
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Directed Chimeric Xylose Isomerase 2

<400> SEQUENCE: 9

```
Met Lys Leu Thr Val Gly Asp Lys Glu Tyr Phe Lys Gly Ile Lys Pro
  1               5                  10                  15

Ile Lys Phe Glu Gly Lys Asp Ser Lys Asn Val Met Ala Phe His Tyr
             20                  25                  30

Tyr Glu Pro Glu Lys Val Val Met Gly Lys Lys Met Lys Asp Trp Leu
         35                  40                  45

Lys Phe Ala Met Ala Trp Trp His Thr Leu Gly Gly Ala Ser Ala Asp
     50                  55                  60

Gln Phe Gly Gly Gln Thr Arg Ser Tyr Glu Trp Asp Lys Ala Ala Asp
 65                  70                  75                  80

Ala Val Gln Arg Ala Lys Asp Lys Met Asp Ala Gly Phe Glu Ile Met
                 85                  90                  95
```

Asp Lys Leu Gly Ile Glu Tyr Phe Cys Phe His Asp Val Asp Leu Val
             100                 105                 110

Glu Glu Gly Glu Thr Ile Ala Glu Tyr Glu Arg Arg Met Lys Glu Ile
         115                 120                 125

Thr Asp Tyr Ala Leu Val Lys Met Lys Glu Tyr Pro Asn Ile Lys Leu
130                 135                 140

Leu Trp Gly Thr Ala Asn Val Phe Gly Asn Lys Arg Tyr Ala Asn Gly
145                 150                 155                 160

Ala Ser Thr Asn Pro Asp Phe Asp Val Val Ala Arg Ala Ile Val Gln
                165                 170                 175

Ile Lys Asn Ala Ile Asp Ala Thr Ile Lys Leu Gly Gly Thr Asn Tyr
            180                 185                 190

Val Phe Trp Gly Gly Arg Glu Gly Tyr Met Thr Leu Leu Asn Thr Asp
            195                 200                 205

Met Lys Arg Glu Gln Glu His Leu Ala Arg Phe Leu Thr Met Ala Lys
210                 215                 220

Asp Tyr Ala Arg Lys Gln Gly Phe Thr Gly Thr Phe Phe Ile Glu Pro
225                 230                 235                 240

Lys Pro Cys Glu Pro Thr Lys His Gln Tyr Asp Tyr Asp Ala Ala Thr
                245                 250                 255

Val Ile Gly Phe Leu Arg His Phe Gly Leu Asp Lys Asp Phe Lys Leu
            260                 265                 270

Asn Leu Glu Val Asn His Ala Thr Leu Ala Gly His Thr Phe Glu His
            275                 280                 285

Glu Leu Ala Cys Ala Val Asp Ala Gly Met Leu Gly Ser Ile Asp Ala
290                 295                 300

Asn Arg Gly Asp Tyr Gln Asn Gly Trp Asp Thr Asp Gln Phe Pro Ile
305                 310                 315                 320

Asp Gln Tyr Glu Leu Val Gln Ala Trp Met Glu Ile Ile Arg Gly Gly
                325                 330                 335

Gly Phe Thr Thr Gly Gly Thr Asn Phe Asp Ala Lys Thr Arg Arg Asn
            340                 345                 350

Ser Thr Asp Leu Glu Asp Ile Ile Ile Ala His Ile Ser Gly Met Asp
            355                 360                 365

Ala Met Ala Arg Ala Leu Glu Asn Ala Ala Lys Leu Leu Thr Glu Ser
370                 375                 380

Pro Tyr Lys Lys Met Lys Ala Asp Arg Tyr Ala Ser Phe Asp Ser Gly
385                 390                 395                 400

Met Gly Lys Asp Phe Glu Asp Gly Lys Leu Thr Phe Glu Gln Val Tyr
                405                 410                 415

Glu Tyr Gly Lys Lys Val Asn Glu Pro Lys Gln Thr Ser Gly Lys Gln
            420                 425                 430

Glu Leu Tyr Glu Ala Ile Val Ala Met Tyr Met
            435                 440

<210> SEQ ID NO 10
<211> LENGTH: 1332
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Directed Chimeric Xylose Isomerase 2

<400> SEQUENCE: 10

```
atgaagttga ccgttggtga caaagaatac ttcaagggta ttaagccaat caagttcgaa      60
ggtaaggact ctaagaacgt tatggctttc cactactacg aaccagaaaa ggttgttatg     120
ggtaagaaga tgaaggactg gttgaagttc gctatggctt ggtggcacac tttgggtggt     180
gcttctgctg accaattcgg tggtcaaact agatcttacg aatgggacaa ggctgctgac     240
gctgttcaaa gagctaagga caagatggac gctggtttcg aaatcatgga caagttgggt     300
atcgaatact ctgttttcca cgacgttgac ttggttgaag aaggtgaaac tatcgctgaa     360
tacgaaagaa gaatgaagga aatcactgac tacgctttgg ttaagatgaa ggaataccca     420
aacatcaagt tgttgtgggg tactgctaac gttttcggta caagagata cgctaacggt      480
gcttctacta acccagactt cgacgttgtt gctagagcta tcgttcaaat caagaacgct     540
atcgacgcta ctatcaagtt gggtggtact aactacgttt ctggggtgg tagagaaggt      600
tacatgactt tgttgaacac cgacatgaag agagaacaag aacatttggc tagattcttg     660
accatggcta agattacgc tagaaagcaa ggtttcaccg gtactttttt cattgaacct       720
aagccatgcg aacctaccaa acatcaatat gattacgatg ctgccaccgt tattggtttt     780
ttgagacatt tcggtttgga caaggacttc aagttgaact tggaagttaa ccatgctact     840
ttggctggtc acactttcga cacgaattg gcttgtgctg ttgacgctgg tatgttgggt       900
tctatcgacg ctaacagagg tgactaccaa acggttggg acactgacca attcccaatc       960
gaccaatacg aattggttca agcttggatg gaaatcatca gaggtggtgg tttcactact    1020
ggtggtacta acttcgacgc taagactaga agaaactcta ctgacttgga agacatcatc    1080
atcgctcaca tctctggtat ggacgctatg gctagagctt tggaaaacgc tgctaagttg    1140
ttgactgaat ctccatacaa gaagatgaag gctgacagat acgcttcttt cgactctggt    1200
atgggtaagg acttcgaaga cggtaagttg actttcgaac aagtttacga atacggtaag    1260
aaggttaacg aaccaaagca aacttctggt aagcaagaat tgtacgaagc tatcgttgct    1320
atgtacatgt ga                                                       1332
```

<210> SEQ ID NO 11
<211> LENGTH: 438
<212> TYPE: PRT
<213> ORGANISM: Bacteroides thetaiotaomicron

<400> SEQUENCE: 11

```
Met Ala Thr Lys Glu Phe Phe Pro Gly Ile Glu Lys Ile Lys Phe Glu
1               5                   10                  15

Gly Lys Asp Ser Lys Asn Pro Met Ala Phe Arg Tyr Tyr Asp Ala Glu
                20                  25                  30

Lys Val Ile Asn Gly Lys Lys Met Lys Asp Trp Leu Arg Phe Ala Met
            35                  40                  45

Ala Trp Trp His Thr Leu Cys Ala Glu Gly Gly Asp Gln Phe Gly Gly
        50                  55                  60

Gly Thr Lys Gln Phe Pro Trp Asn Gly Asn Ala Asp Ala Ile Gln Ala
65                  70                  75                  80

Ala Lys Asp Lys Met Asp Ala Gly Phe Glu Phe Met Gln Lys Met Gly
                85                  90                  95

Ile Glu Tyr Tyr Cys Phe His Asp Val Asp Leu Val Ser Glu Gly Ala
                100                 105                 110

Ser Val Glu Glu Tyr Glu Ala Asn Leu Lys Glu Ile Val Ala Tyr Ala
            115                 120                 125
```

Lys Gln Lys Gln Ala Glu Thr Gly Ile Lys Leu Leu Trp Gly Thr Ala
130                 135                 140

Asn Val Phe Gly His Ala Arg Tyr Met Asn Gly Ala Ala Thr Asn Pro
145                 150                 155                 160

Asp Phe Asp Val Val Ala Arg Ala Ala Val Gln Ile Lys Asn Ala Ile
                165                 170                 175

Asp Ala Thr Ile Glu Leu Gly Gly Glu Asn Tyr Val Phe Trp Gly Gly
                180                 185                 190

Arg Glu Gly Tyr Met Ser Leu Leu Asn Thr Asp Gln Lys Arg Glu Lys
                195                 200                 205

Glu His Leu Ala Gln Met Leu Thr Ile Ala Arg Asp Tyr Ala Arg Ala
210                 215                 220

Arg Gly Phe Lys Gly Thr Phe Leu Ile Glu Pro Lys Pro Met Glu Pro
225                 230                 235                 240

Thr Lys His Gln Tyr Asp Val Asp Thr Glu Thr Val Ile Gly Phe Leu
                245                 250                 255

Lys Ala His Gly Leu Asp Lys Asp Phe Lys Val Asn Ile Glu Val Asn
                260                 265                 270

His Ala Thr Leu Ala Gly His Thr Phe Glu His Glu Leu Ala Val Ala
                275                 280                 285

Val Asp Asn Gly Met Leu Gly Ser Ile Asp Ala Asn Arg Gly Asp Tyr
290                 295                 300

Gln Asn Gly Trp Asp Thr Asp Gln Phe Pro Ile Asp Asn Tyr Glu Leu
305                 310                 315                 320

Thr Gln Ala Met Met Gln Ile Ile Arg Asn Gly Gly Leu Gly Thr Gly
                325                 330                 335

Gly Thr Asn Phe Asp Ala Lys Thr Arg Arg Asn Ser Thr Asp Leu Glu
                340                 345                 350

Asp Ile Phe Ile Ala His Ile Ala Gly Met Asp Ala Met Ala Arg Ala
                355                 360                 365

Leu Glu Ser Ala Ala Ala Leu Leu Asp Glu Ser Pro Tyr Lys Lys Met
370                 375                 380

Leu Ala Asp Arg Tyr Ala Ser Phe Asp Gly Gly Lys Gly Lys Glu Phe
385                 390                 395                 400

Glu Asp Gly Lys Leu Thr Leu Glu Asp Val Val Ala Tyr Ala Lys Thr
                405                 410                 415

Lys Gly Glu Pro Lys Gln Thr Ser Gly Lys Gln Glu Leu Tyr Glu Ala
                420                 425                 430

Ile Leu Asn Met Tyr Cys
                435

<210> SEQ ID NO 12
<211> LENGTH: 1317
<212> TYPE: DNA
<213> ORGANISM: Bacteroides thetaiotaomicron

<400> SEQUENCE: 12
atggcaacaa aagaattttt tccgggaatt gaaagatta aatttgaagg taagatagt        60 aagaacccga tggcattccg ttattacgat gcagagaagg tgattaatgg taaaagatg      120 aaggattggc tgagattcgc tatggcatgg tggcacacat tgtgcgctga aggtggtgat      180
cagttcggtg gcggaacaaa gcaattccca tggaatggta atgcagatgc tatacaggca      240
gcaaaagata gatggatgc aggatttgaa ttcatgcaga gatgggtat cgaatactat       300 tgcttccatg acgtagactt ggtttcggaa ggtgccagtg tagaagaata cgaagctaac      360

```
ctgaaagaaa tcgtagctta tgcaaaacag aaacaggcag aaaccggtat caaactactg    420
tggggtactg ctaatgtatt cggtcacgcc cgctatatga acggtgcagc taccaatcct    480
gacttcgatg tagtagctcg tgctgctgtt cagatcaaaa atgcgattga tgcaacgatt    540
gaacttggcg gagagaatta tgtgttttgg ggtggtcgtg aaggctatat gtctcttctg    600
aacacagatc agaaacgtga aaaagaacac cttgcacaga tgttgacgat gctcgtgac    660 tatgcccgtg cccgtggttt caaaggtact ttcctgatcg aaccgaaacc gatgaaccg    720 actaaacatc aatatgacgt agatacggaa actgtaatcg gcttcctgaa agctcatggt    780
ctggataagg atttcaaagt aaatatcgag gtgaatcacg caactttggc aggtcacact    840
ttcgagcatg aattggctgt agctgtagac aatggtatgt tgggctcaat tgacgccaat    900
cgtggtgact atcagaatgg ctgggataca gaccaattcc cgatcgacaa ttatgaactg    960
actcaggcta tgatgcagat tatccgtaat ggtggtctcg gtaccggtgg tacgaacttt    1020
gatgctaaaa cccgtcgtaa ttctactgat ctggaagata tctttattgc tcacatcgca    1080
ggtatggacg ctatggcccg tgcactcgaa agtgcagcgg ctctgctcga cgaatctccc    1140
tataagaaga tgctggctga ccgttatgct tcatttgatg ggggcaaagg taaagaattt    1200
gaagacggca agctgactct ggaggatgtg gttgcttatg caaaaacaaa aggcgaaccg    1260
aaacagacta gcggcaagca agaactttat gaggcaattc tgaatatgta ttgctaa     1317
```

<210> SEQ ID NO 13
<211> LENGTH: 442
<212> TYPE: PRT
<213> ORGANISM: Parabacteroides distasonis

<400> SEQUENCE: 13

```
Met Ser Tyr Phe Lys Gly Glu Lys Glu Phe Pro Gly Ile Gly Gln
1               5                   10                  15

Ile Gln Phe Glu Gly Arg Glu Ser Lys Asn Pro Leu Ala Phe His Tyr
            20                  25                  30

Tyr Asp Ala Asp Lys Val Val Met Gly Lys Thr Leu Lys Asp His Leu
        35                  40                  45

Arg Phe Ala Met Ala Tyr Trp His Thr Leu Cys Ala Glu Gly Gly Asp
    50                  55                  60

Gln Phe Gly Gly Gly Thr Lys Thr Phe Pro Trp Asn Asp Ser Thr Asp
65                  70                  75                  80

Ala Ile Thr Arg Ala Lys Tyr Lys Met Asp Ala Ala Phe Glu Phe Met
                85                  90                  95

Thr Lys Cys Asn Ile Pro Tyr Tyr Cys Phe His Asp Val Asp Val Val
            100                 105                 110

Asp Glu Ala Pro Thr Leu Gly Glu Phe Glu Lys Arg Leu Gln Thr Met
        115                 120                 125

Val Glu His Ala Lys Glu His Gln Ala Ala Thr Gly Lys Lys Leu Leu
    130                 135                 140

Trp Ser Thr Ala Asn Val Phe Gly His Lys Arg Tyr Met Asn Gly Ala
145                 150                 155                 160

Ala Thr Asn Pro Tyr Phe Pro Thr Val Ala Cys Val Gly Thr Gln Ile
                165                 170                 175

Lys Asn Ala Ile Asp Ala Cys Ile Ala Leu Gly Gly Glu Asn Tyr Val
            180                 185                 190

Phe Trp Gly Gly Arg Glu Gly Tyr Met Ser Leu Leu Asn Thr Asn Met
        195                 200                 205
```

```
Lys Arg Glu Lys Asp His Leu Ala Met Met Leu Thr Met Ala Arg Asp
        210                 215                 220
Tyr Gly Arg Lys Asn Gly Phe Lys Gly Thr Phe Leu Ile Glu Pro Lys
225                 230                 235                 240
Pro Met Glu Pro Thr Lys His Gln Tyr Asp Val Asp Ser Glu Thr Val
                245                 250                 255
Ile Gly Phe Leu Arg His Tyr Gly Leu Asp Lys Asp Phe Ala Leu Asn
            260                 265                 270
Ile Glu Val Asn His Ala Thr Leu Ala Gly His Thr Phe Glu His Glu
        275                 280                 285
Leu Gln Ala Ala Ala Asp Ala Gly Met Leu Cys Ser Ile Asp Ala Asn
    290                 295                 300
Arg Gly Asp Tyr Gln Asn Gly Trp Asp Thr Asp Gln Phe Pro Met Asp
305                 310                 315                 320
Ile Tyr Glu Leu Ala Gln Ala Trp Leu Val Ile Leu Glu Gly Gly
                325                 330                 335
Leu Thr Thr Gly Gly Thr Asn Phe Asp Ala Lys Thr Arg Arg Asn Ser
            340                 345                 350
Thr Asp Leu Glu Asp Ile Phe Ile Ala His Ile Gly Gly Met Asp Ala
        355                 360                 365
Phe Ala Arg Ala Leu Met Ile Ala Ala Asp Ile Leu Glu Asn Ser Asp
    370                 375                 380
Tyr Arg Lys Met Arg Ala Glu Arg Tyr Ala Ser Phe Asp Ala Gly Glu
385                 390                 395                 400
Gly Lys Ala Phe Glu Asp Gly Lys Leu Thr Leu Glu Asp Leu Arg Thr
                405                 410                 415
Ile Ala Leu Arg Asp Gly Glu Pro Lys Gln Ile Ser Gly Lys Gln Glu
            420                 425                 430
Leu Tyr Glu Met Ile Val Asn Leu His Ile
        435                 440

<210> SEQ ID NO 14
<211> LENGTH: 1329
<212> TYPE: DNA
<213> ORGANISM: Parabacteroides distasonis

<400> SEQUENCE: 14
atgtcttact ttaagggtga aaagaattc ttcccaggta tcggtcaaat ccaatttgaa    60
ggtagagaat ccaagaaccc attggctttt cattattacg atgccgataa ggttgtcatg   120
ggtaaaactt tgaaggacca tttgagattc gctatggctt attggcatac tttgtgtgct   180
gaaggtggtg atcaatttgg tggtggtaca aaaactttcc catggaatga ttccaccgat   240
gctattacta gagccaagta caaaatggat gctgcttttg aattcatgac caagtgcaac   300
attccttact actgcttcca cgatgttgat gttgttgatg aagctccaac tttgggtgaa   360
ttcgaaaaaa gattgcaaac catggtcgaa catgccaaag aacatcaagc tgctactggt   420
aaaaagttgt gtgggtctac tgctaatgtt ttcggtcaca agagatatat gaacggtgct   480
gctactaatc catactttcc aactgttgct tgcgttggta ctcaaatcaa gaatgctatt   540
gatgcttgca ttgctttggg tggtgaaaat tatgttttct ggggtggtag agaaggttac   600
atgtctttgt tgaacaccaa catgaagaga gaaaaggatc atttggccat gatgttgact   660
atggctagag attacggtag aaagaatggt ttcaagggta ctttcttgat cgaacctaaa   720
cctatggaac tactaagca ccaatacgat gttgattccg aaaccgttat cggtttcttg   780
```

-continued

```
agacattacg gtttggataa ggatttcgcc ttgaacatcg aagttaacca tgctactttg      840
gctggtcata ctttcgaaca tgaattgcaa gctgctgctg atgctggtat gttgtgttct      900
attgatgcta acagaggtga ctaccaaaat ggttgggata ctgatcaatt cccaatggat      960
atctacgaat tggctcaagc ttggttggtt attttggaag gtggtggttt gactactggt     1020
ggtactaatt ttgatgccaa gaccagaaga aactccactg atttggaaga catcttcatt     1080
gcccatatcg gtggtatgga tgcttttgct agagctttga tgattgctgc cgatattttg     1140
gaaaactccg actacagaaa gatgagagct gaaagatacg cttctttga tgctggtgaa      1200
ggtaaggctt tcgaagatgg taaattgacc ttggaagatt tgagaaccat tgctttgaga     1260
gatggtgaac ctaagcaaat ttccggtaag caagaattat acgaaatgat cgtcaacttg     1320
cacatctaa                                                             1329
```

<210> SEQ ID NO 15
<211> LENGTH: 437
<212> TYPE: PRT
<213> ORGANISM: Cyllamyces aberensis

<400> SEQUENCE: 15

```
Met Val Lys Glu Tyr Phe Pro Ala Ile Gln Lys Ile Lys Phe Glu Gly
1               5                   10                  15
Lys Asp Ser Lys Asn Pro Met Ala Phe His Tyr Tyr Asp Ala Glu Lys
            20                  25                  30
Glu Ile Met Gly Lys Lys Met Lys Asp Trp Leu Arg Phe Ala Met Ala
        35                  40                  45
Trp Trp His Thr Leu Cys Ala Glu Gly Ser Asp Gln Phe Gly Pro Gly
    50                  55                  60
Thr Lys Thr Phe Pro Trp Asn Glu Gly Thr Asp Pro Ile Glu Lys Ala
65                  70                  75                  80
Lys Gln Lys Val Asp Ala Gly Phe Glu Ile Met Thr Lys Leu Gly Ile
                85                  90                  95
Glu His Tyr Cys Phe His Asp Val Asp Leu Val Asp Glu Gly Lys Asn
            100                 105                 110
Val Glu Glu Tyr Glu Lys Asn Leu Lys Thr Ile Val Ala Tyr Leu Lys
        115                 120                 125
Glu Lys Gln Lys Glu Thr Gly Ile Lys Leu Leu Trp Ser Thr Ala Asn
    130                 135                 140
Val Phe Gly His Lys Arg Tyr Met Asn Gly Ala Ser Thr Asn Pro Asp
145                 150                 155                 160
Phe Asp Val Val Ala Arg Ala Ile Val Gln Ile Lys Asn Ala Met Asp
                165                 170                 175
Ala Gly Ile Glu Leu Gly Ala Glu Asn Tyr Val Phe Trp Gly Gly Arg
            180                 185                 190
Glu Gly Tyr Met Ser Leu Leu Asn Thr Asp Gln Lys Arg Glu Lys Glu
        195                 200                 205
His Met Ala Met Met Leu Gly Leu Ala Arg Asp Tyr Ala Arg Ser Lys
    210                 215                 220
Gly Phe Lys Gly Thr Phe Leu Ile Glu Pro Lys Pro Met Glu Pro Thr
225                 230                 235                 240
Lys His Gln Tyr Asp Val Asp Thr Glu Thr Val Ile Gly Phe Leu Arg
                245                 250                 255
Ala His Gly Leu Asp Lys Asp Phe Lys Ile Asn Ile Glu Val Asn His
            260                 265                 270
```

```
Ala Thr Leu Ala Gly His Thr Phe Glu His Glu Leu Ala Cys Ala Val
        275                 280                 285

Asp Ala Gly Met Leu Gly Ser Ile Asp Ala Asn Arg Gly Asp Tyr Gln
    290                 295                 300

Asn Gly Trp Asp Thr Asp Gln Phe Pro Ile Asp Gln Tyr Glu Leu Val
305                 310                 315                 320

Gln Ala Trp Met Glu Ile Ile Arg Gly Gly Phe Thr Thr Gly Gly
                325                 330                 335

Thr Asn Phe Asp Ala Lys Thr Arg Arg Asn Ser Thr Asp Leu Glu Asp
                340                 345                 350

Ile Ile Ile Ala His Ile Ser Gly Met Asp Ala Met Ala Arg Ala Leu
        355                 360                 365

Glu Asn Ala Ala Lys Leu Leu Thr Glu Ser Pro Tyr Lys Lys Met Lys
370                 375                 380

Ala Asp Arg Tyr Ala Ser Phe Asp Ser Gly Met Gly Lys Asp Phe Glu
385                 390                 395                 400

Asp Gly Lys Leu Thr Phe Glu Gln Val Tyr Glu Tyr Gly Lys Lys Val
                405                 410                 415

Asn Glu Pro Lys Gln Thr Ser Gly Lys Gln Leu Tyr Glu Ala Ile
                420                 425                 430

Val Ala Met Tyr Met
        435

<210> SEQ ID NO 16
<211> LENGTH: 1314
<212> TYPE: DNA
<213> ORGANISM: Cyllamyces aberensis

<400> SEQUENCE: 16
atggttaagg aatacttccc agctatccaa agatcaagt tcgaaggtaa ggactctaag      60
aacccaatgg ctttccacta ctacgacgct gaaaaggaaa tcatgggtaa gaagatgaag   120
gactggttga gattcgctat ggcttggtgg cacactttgt gtgctgaagg ttctgaccaa   180
tcggtccag gtactaagac tttcccatgg aacgaaggta ctgacccaat cgaaaaggct    240
aagcaaaagg ttgacgctgg tttcgaaatc atgactaagt gggtatcga acactactgt    300
ttccacgacg ttgacttggt tgacgaaggt aagaacgttg aagaatacga aaagaacttg   360
aagactatcg ttgcttactt gaaggaaaag caaaaggaaa ctggtatcaa gttgttgtgg   420
tctactgcta acgttttcgg tcacaagaga tacatgaacg tgcttctac taacccagac    480
tcgacgttg ttgctagagc tatcgttcaa atcaagaacg ctatggacgc tggtatcgaa    540
ttgggtgctg aaaactacgt tttctggggt ggtagaaag gttacatgtc tttgttgaac    600
actgaccaaa agagagaaaa ggaacacatg gctatgatgt tgggtttggc tagagactac   660
gctagatcta agggtttcaa gggtactttc ttgatcgaac caaagccaat ggaaccaact   720
aagcaccaat acgacgttga cactgaaact gttatcggtt tcttgagagc tcacggtttg   780
gacaaggact tcaagatcaa catcgaagtt aaccacgcta ctttggctgg tcacactttc   840
gaacacgaat ggcttgtgc tgttgacgct ggtatgttgg ttctatcga cgctaacaga    900
ggtgactacc aaaacggttg ggacactgac caattcccaa tcgaccaata cgaattggtt   960
caagcttgga tggaaatcat cagaggtggt ggtttcacta ctggtggtac taacttcgac 1020
gctaagacta agaaactct actgacttg aagacatca tcatcgctca catctctggt     1080
atggacgcta tggctagagc tttggaaaac gctgctaagt tgttgactga atctccatac 1140
```
aagaagatga aggctgacag atacgcttct ttcgactctg gtatgggtaa ggacttcgaa    1200
gacggtaagt tgactttcga acaagtttac gaatacggta agaaggttaa cgaaccaaag    1260
caaacttctg gtaagcaaga attgtacgaa gctatcgttg ctatgtacat gtga          1314

<210> SEQ ID NO 17
<211> LENGTH: 440
<212> TYPE: PRT
<213> ORGANISM: Abiotrophia defectiva

<400> SEQUENCE: 17

Met Ser Glu Leu Phe Gln Asn Ile Pro Lys Ile Lys Tyr Glu Gly Ala
1               5                   10                  15

Asn Ser Lys Asn Pro Leu Ala Phe His Tyr Tyr Asp Ala Glu Lys Ile
            20                  25                  30

Val Leu Gly Lys Thr Met Lys Glu His Leu Pro Phe Ala Met Ala Trp
        35                  40                  45

Trp His Asn Leu Cys Ala Ala Gly Thr Asp Met Phe Gly Arg Asp Thr
    50                  55                  60

Ala Asp Lys Ser Phe Gly Leu Glu Lys Gly Ser Met Glu His Ala Lys
65                  70                  75                  80

Ala Lys Val Asp Ala Gly Phe Glu Phe Met Glu Lys Leu Gly Ile Lys
                85                  90                  95

Tyr Phe Cys Phe His Asp Val Asp Leu Val Pro Glu Ala Cys Asp Ile
            100                 105                 110

Lys Glu Thr Asn Ser Arg Leu Asp Glu Ile Ser Asp Tyr Ile Leu Glu
        115                 120                 125

Lys Met Lys Gly Thr Asp Ile Lys Cys Leu Trp Gly Thr Ala Asn Met
    130                 135                 140

Phe Ser Asn Pro Arg Phe Val Asn Gly Ala Gly Ser Thr Asn Ser Ala
145                 150                 155                 160

Asp Val Tyr Cys Phe Ala Ala Ala Gln Ile Lys Lys Ala Leu Asp Ile
                165                 170                 175

Thr Val Lys Leu Gly Gly Arg Gly Tyr Val Phe Trp Gly Gly Arg Glu
            180                 185                 190

Gly Tyr Glu Thr Leu Leu Asn Thr Asp Val Lys Phe Glu Gln Glu Asn
        195                 200                 205

Ile Ala Asn Leu Met Lys Met Ala Val Glu Tyr Gly Arg Ser Ile Gly
    210                 215                 220

Phe Lys Gly Asp Phe Tyr Ile Glu Pro Lys Pro Lys Glu Pro Met Lys
225                 230                 235                 240

His Gln Tyr Asp Phe Asp Ala Ala Thr Ala Ile Gly Phe Leu Arg Gln
                245                 250                 255

Tyr Gly Leu Asp Lys Asp Phe Lys Leu Asn Ile Glu Ala Asn His Ala
            260                 265                 270

Thr Leu Ala Gly His Ser Phe Gln His Glu Leu Arg Ile Ser Ser Ile
        275                 280                 285

Asn Gly Met Leu Gly Ser Val Asp Ala Asn Gln Gly Asp Met Leu Leu
    290                 295                 300

Gly Trp Asp Thr Asp Glu Phe Pro Phe Asp Val Tyr Asp Thr Thr Met
305                 310                 315                 320

Cys Met Tyr Glu Val Leu Lys Asn Gly Gly Leu Thr Gly Gly Phe Asn
                325                 330                 335

Phe Asp Ala Lys Asn Arg Arg Pro Ser Tyr Thr Tyr Glu Asp Met Phe

```
            340                 345                 350
Tyr Gly Phe Ile Leu Gly Met Asp Ser Phe Ala Leu Gly Leu Ile Lys
            355                 360                 365

Ala Ala Lys Leu Ile Glu Glu Gly Thr Leu Asp Asn Phe Ile Lys Glu
        370                 375                 380

Arg Tyr Lys Ser Phe Glu Ser Glu Ile Gly Lys Lys Ile Arg Ser Lys
385                 390                 395                 400

Ser Ala Ser Leu Gln Glu Leu Ala Ala Tyr Ala Glu Glu Met Gly Ala
                405                 410                 415

Pro Ala Met Pro Gly Ser Gly Arg Gln Glu Tyr Leu Gln Ala Ala Leu
            420                 425                 430

Asn Gln Asn Leu Phe Gly Glu Val
            435                 440

<210> SEQ ID NO 18
<211> LENGTH: 1323
<212> TYPE: DNA
<213> ORGANISM: Abiotrophia defectiva

<400> SEQUENCE: 18
atgtctgaat tgttccaaaa catcccaaag atcaagtacg aaggtgctaa ctctaagaac      60
ccattggctt tccactacta cgacgctgaa aagatcgttt gggtaagac tatgaaggaa      120 cacttgccat tcgctatggc ttggtggcac aacttgtgtg ctgctggtac tgacatgttc      180
ggtagagaca ctgctgacaa gtctttcggt ttggaaaagg ttctatggaa cacgctaag      240 gctaaggttg acgctggttt cgaattcatg gaaaagttgg gtatcaagta cttctgtttc      300
cacgacgttg acttggttcc agaagcttgt gacatcaagg aaactaactc tagattggac      360
gaaatctctg actacatctt ggaaagatg aagggtactg acatcaagtg tttgtggggt      420
actgctaaca tgttctctaa cccaagattc gttaacggtg ctggttctac taactctgct      480
gacgtttact gtttcgctgc tgctcaaatc aagaaggctt ggacatcac tgttaagttg      540 ggtggtagag gttacgtttt ctggggtggt agagaaggtt acgaaacttt gttgaacact      600
gacgttaagt tcgaacaaga aaacatcgct aacttgatga gatggctgtt gaatacggt      660 agatctatcg gtttcaaggg tgacttctac atcgaaccaa gccaaaggat accaatgaag      720
caccaatacg acttcgacgc tgctactgct atcggtttct tgagacaata cggtttggac      780
aaggacttca gttgaacat cgaagctaac cacgctactt tggctggtca ctcttttccaa      840 cacgaattga gaatctcttc tatcaacggt atgtttgggtt ctgttgacgc taaccaaggt      900
gacatgttgt tgggttggga cactgacgaa ttcccattcg acgtttacga cactactatg      960
tgtatgtacg aagttttgaa gaacggtggt tgactggtg gtttcaactt cgacgctaag     1020
aacagaagac catcttacac ttacgaagac atgttctacg gtttcatctt gggtatggac     1080
tctttcgctt gggtttgat caaggctgct aagttgatcg aagaaggtac tttggacaac     1140
ttcatcaagg aaagatacaa gtctttcgaa tctgaaatcg gtaagaagat cagatctaag     1200
tctgcttctt tgcaagaatt ggctgcttac gctgaagaaa tgggtgctcc agctatgcca     1260
ggttctggta gacaagaata cttgcaagct gcttttgaacc aaaacttgtt cggtgaagtt     1320
tga                                                                  1323

<210> SEQ ID NO 19
<211> LENGTH: 442
<212> TYPE: PRT
<213> ORGANISM: Unknown
```

<220> FEATURE:
<223> OTHER INFORMATION: Description of Unknown:
      Uncultured bacterium XYM2

<400> SEQUENCE: 19

Met Lys Leu Thr Val Gly Asp Lys Glu Tyr Phe Lys Gly Ile Lys Pro
1               5                   10                  15

Ile Lys Phe Glu Gly Lys Asp Ser Asp Asn Pro Leu Ala Phe Lys Tyr
                20                  25                  30

Tyr Asn Pro Ser Gln Lys Val Gly Lys Thr Met Glu Glu His Phe
            35                  40                  45

Arg Phe Ala Ile Ala Tyr Trp His Thr Phe Cys Gly Thr Gly Gly Asp
        50                  55                  60

Pro Phe Gly Pro Gly Thr Lys Thr Phe Pro Trp Leu Gln Asn Ser Asp
65                  70                  75                  80

Ala Val Gln Arg Ala Tyr Asp Lys Met Asp Ala Ala Phe Glu Phe Ile
                85                  90                  95

Thr Lys Ile Gly Ala Pro Phe Tyr Cys Phe His Asp Tyr Asp Leu Val
                100                 105                 110

Asp Glu Gly Pro Thr Leu Lys Glu Ser Glu Ser Arg Leu Gln Lys Val
            115                 120                 125

Val Asp Tyr Ala Lys Lys Lys Gln Lys Ala Ser Gly Val Lys Leu Leu
130                 135                 140

Trp Gly Thr Ala Asn Leu Phe Ser His Pro Arg Tyr Met Asn Gly Ala
145                 150                 155                 160

Ala Thr Asn Pro Asp Phe Asp Val Val Cys Tyr Ala Ala Ser Gln Val
                165                 170                 175

Lys Asn Ala Leu Asp Ala Thr Ile Ala Leu Gly Gly Ala Asn Tyr Val
            180                 185                 190

Phe Trp Gly Gly Arg Glu Gly Tyr Met Ser Leu Leu Asn Thr Asn Met
        195                 200                 205

Lys Arg Glu Gln Glu His Met Ala Lys Phe Leu His Met Ala Lys Asp
210                 215                 220

Tyr Ala Arg Ala Asn Gly Phe Lys Gly Thr Phe Phe Ile Glu Pro Lys
225                 230                 235                 240

Pro Met Glu Pro Ser Lys His Gln Tyr Asp Phe Asp Ser Ala Thr Val
                245                 250                 255

Ile Gly Phe Leu Arg Gln Phe Asp Leu Leu Gly Asp Phe Lys Leu Asn
            260                 265                 270

Ile Glu Val Asn His Ala Thr Leu Ala His His Thr Phe Gln His Glu
        275                 280                 285

Leu Gln Val Ala Ala Asp Ala Gly Ala Leu Gly Ser Ile Asp Ala Asn
290                 295                 300

Arg Gly Asp Tyr Gln Asn Gly Trp Asp Thr Asp Gln Phe Pro Asn Asn
305                 310                 315                 320

Leu Tyr Glu Leu Ala Glu Ser Met Leu Val Ile Leu Glu Ala Gly Gly
                325                 330                 335

Phe Lys Ser Gly Gly Val Asn Phe Asp Ala Lys Thr Arg Arg Asn Ser
            340                 345                 350

Thr Asp Leu Val Asp Ile Phe His Ala His Ile Gly Gly Met Asp Thr
        355                 360                 365

Phe Ala Arg Ser Leu Leu Ile Ala Gln Ala Val Leu Asp Asn Gly Glu
370                 375                 380

Tyr Thr Lys Ile Arg Lys Asp Arg Tyr Ser Ser Phe Asp Ser Gly Lys

```
                385                 390                 395                 400
Gly Lys Gln Phe Asp Gln Gly Lys Leu Ser Leu Glu Asp Leu Arg Asn
                    405                 410                 415
Leu Ala His Lys Ala Gly Glu Pro Lys Gln Leu Ser Gly Lys Gln Glu
                420                 425                 430

Tyr Ile Glu Asn Leu Ile Ser Arg Phe Ile
            435                 440

<210> SEQ ID NO 20
<211> LENGTH: 1329
<212> TYPE: DNA
<213> ORGANISM: Unknown
<220> FEATURE:
<223> OTHER INFORMATION: Description of Unknown:
      Uncultured bacterium XYM2

<400> SEQUENCE: 20
atgaagttga ccgttggtga caaagaatac ttcaagggta ttaagccaat caagttcgaa      60
ggtaaggatt ccgataatcc attggctttc aagtactaca acccatctca aaaggttggt     120
aaaaagacca tggaagaaca tttcagattc gctattgctt actggcatac ttttgtggt     180 actggtggtg atccatttgg tccaggtaca aaaactttc catggttgca aaactccgat     240
gctgttcaaa gagcttacga taagatggat gctgcctttg aattcattac caaaattggt     300
gctccattct actgcttcca tgattacgat ttggttgatg aaggtccaac cttgaaagaa     360
tccgaatcca gattgcaaaa ggtcgttgat tacgctaaga aaagcaaaa agcctccggt     420 gttaagttgt tgtggggtac tgctaatttg ttctcccatc aagatatat gaatggtgct     480 gctacaaacc cagatttcga tgttgtttgt tatgctgcct ctcaagttaa gaatgctttg     540
gatgctacta ttgctttggg tggtgctaat tatgtttttt ggggtggtag agaaggttac     600
atgtctttgt tgaacaccaa catgaagaga gaacaagaac atatggctaa gttcttgcat     660
atggccaagg attatgctag agctaatggt tttaagggta ctttcttcat cgaacctaaa     720
cctatggaac catctaagca ccaatacgat tttgattccg ctaccgttat ggtttcttg     780 agacaatttg atttgttggg tgacttcaag ttgaacatcg aagttaacca tgctaccttg     840
gctcatcata ccttttcaaca tgaattgcaa gttgctgctg atgctggtgc tttaggttct     900
attgatgcta atagaggtga ctaccaaaac ggttgggata ctgatcaatt tccaaacaac     960
ttgtacgaat tggccgaatc catgttggtt attttggaag ctggtggttt taaatccggt    1020
ggtgttaatt tcgatgctaa gaccagaaga aactctaccg atttggtcga tattttccat    1080
gctcatattg gtggtatgga tacctttgct agatccttgt tgattgctca agctgttttg    1140
gataatggtg aatacaccaa gatcagaaag gacagatact cctcttttcga ttctggtaaa    1200 ggtaagcaat tcgatcaagg taaattgtcc ttggaagatt tgagaaactt ggctcacaaa    1260
gctggtgaac ctaagcaatt gtctggtaag caagaatata tcgaaaactt gatctccaga    1320
ttcatttga                                                            1329

<210> SEQ ID NO 21
<211> LENGTH: 442
<212> TYPE: PRT
<213> ORGANISM: Chitinophaga pinensis

<400> SEQUENCE: 21

Met Ser Ile Thr Leu Gly Asn Gln Glu Tyr Phe Lys Gly Ile Gly Lys
1               5                   10                  15
```

-continued

```
Ile Ala Tyr Glu Gly Pro Gln Ser Thr Asn Pro Phe Ala Tyr Lys Trp
            20                  25                  30

Tyr Asp Glu Asn Arg Lys Ile Gly Gly Lys Thr Met Lys Glu Leu Phe
        35                  40                  45

Arg Phe Ala Val Ser Tyr Trp His Thr Phe Cys Gly Thr Gly Gly Asp
    50                  55                  60

Pro Phe Gly Pro Gly Thr Lys Ala Phe Pro Trp Leu Thr Ala Thr Asp
65                  70                  75                  80

Ala Val Gln Ser Ala Lys Asp Lys Met Asp Ala Ala Phe Glu Phe Phe
                85                  90                  95

Thr Lys Leu Gly Val Pro Tyr Tyr Cys Phe His Asp Val Asp Leu Val
            100                 105                 110

Asp Glu Gly Ala Ser Ile Ser Glu Tyr Glu Ser Arg Met Gln Gln Ile
        115                 120                 125

Val Glu Tyr Ala Lys Glu Lys Gln Lys Ala Ser Gly Val Lys Leu Leu
    130                 135                 140

Trp Gly Thr Ala Asn Val Phe Ser Asn Pro Arg Tyr Met Asn Gly Ala
145                 150                 155                 160

Ala Thr Asn Pro Asp Phe Ala Ala Val Ala Tyr Ala Gly Thr Gln Val
                165                 170                 175

Lys Asn Ser Leu Asp Ala Thr Ile Ala Leu Gly Gly Glu Asn Tyr Val
            180                 185                 190

Phe Trp Gly Gly Arg Glu Gly Tyr Met Thr Leu Leu Asn Thr Asp Met
        195                 200                 205

Lys Arg Glu Gln Glu His Leu Ala Arg Phe Leu Thr Met Ala Lys Asp
210                 215                 220

Tyr Ala Arg Lys Gln Gly Phe Thr Gly Thr Phe Phe Ile Glu Pro Lys
225                 230                 235                 240

Pro Cys Glu Pro Thr Lys His Gln Tyr Asp Tyr Asp Ala Ala Thr Val
                245                 250                 255

Ile Gly Phe Leu Arg His Phe Gly Leu Asp Lys Asp Phe Lys Leu Asn
            260                 265                 270

Leu Glu Val Asn His Ala Thr Leu Ala Gly His Thr Phe Gln His Glu
        275                 280                 285

Leu Gln Val Ala Ala Asp Ala Gly Met Leu Gly Ser Ile Asp Ala Asn
    290                 295                 300

Arg Gly Asp Ala Gln Asn Gly Trp Asp Thr Asp Gln Phe Pro Met Asn
305                 310                 315                 320

Leu Asn Asp Met Val Glu Phe Met Leu Val Ile Leu Glu Ala Gly Gly
                325                 330                 335

Phe Ser Gly Gly Gly Val Asn Phe Asp Ala Lys Thr Arg Arg Asn Ser
            340                 345                 350

Thr Asp Leu Glu Asp Ile Phe His Ala His Ile Gly Gly Ile Asp Ser
        355                 360                 365

Phe Ala Arg Ala Ala Val Ile Ala Glu Lys Val Leu Glu Gln Ser Pro
    370                 375                 380

Tyr Lys Gln Phe Arg Lys Asp Arg Tyr Ala Ser Phe Asp Ser Gly Lys
385                 390                 395                 400

Gly Lys Asp Phe Glu Ala Gly Thr Leu Thr Leu Glu Asp Leu Arg Ser
                405                 410                 415

Phe Ala Val Ser Asn Gly Glu Pro Lys His Ile Ser Gly Lys Gln Glu
            420                 425                 430

Trp Leu Glu Asn Ile Ile Asn Gln Tyr Ile
```

<210> SEQ ID NO 22
<211> LENGTH: 1329
<212> TYPE: DNA
<213> ORGANISM: Chitinophaga pinensis

<400> SEQUENCE: 22

```
atgtccatca ccttgggtaa tcaagaatac ttcaagggta ttggtaagat tgcttacgaa      60
ggtccacaat ctactaatcc atttgcttac aagtggtacg acgaaaacag aaaaattggt     120
ggtaagacca tgaaggaatt attcagattc gctgtttcct actggcatac ttttttgtgt     180
actggtggtg atccatttgg tccaggtaca aaagcttttc catggttgac tgctactgat     240
gctgttcaat ctgctaagga taagatggat gctgcttttg aattcttcac caaattgggt     300
gttccttact actgcttcca cgatgttgat ttggttgatg aaggtgcttc catttctgaa     360
tacgaatcca gaatgcaaca aatcgtcgaa tacgccaaag aaaagcaaaa agcttccggt     420
gttaagttgt tgtggggtac tgctaatgtt ttctccaacc caagatatat gaacggtgct     480
gctactaatc cagattttgc tgctgttgct tatgctggta ctcaagttaa gaactctttg     540
gatgctacca ttgctttggg tggtgaaaat tatgttttct ggggtggtag agaaggttac     600
atgactttgt tgaacaccga catgaagaga gaacaagaac atttggctag attcttgacc     660
atggctaaag attacgctag aaagcaaggt ttcaccggta cttttttcat tgaacctaag     720
ccatgcgaac ctaccaaaca tcaatatgat tacgatgctg ccaccgttat tggtttttttg     780
agacatttcg gtttggacaa ggacttcaag ttgaacttgg aagttaacca tgctactttg     840
gctggtcata ctttccaaca cgaattgcaa gttgctgctg atgctggtat gttgggttct     900
attgatgcta atagaggtga tgctcaaaac ggttgggata ctgatcaatt tccaatgaac     960
ttgaacgaca tggtcgaatt catgttggtt attttggaag ctggtggttt ttctggtggt    1020
ggtgttaatt ttgatgccaa gactagaaga aactccaccg atttggaaga tattttccat    1080
gctcatatcg gtggtattga ttcttttgct agagctgctg ttatcgctga aaaggttttg    1140
gaacaatccc catacaagca attcagaaag gatagatacg cttcttttga ttctggtaag    1200
ggtaaggatt ttgaagctgg tacttttgacc ttggaagatt tgagatcttt cgctgtttct    1260
aacggtgaac ctaaacatat ttccggtaag caagaatggt tggaaaacat catcaatcag    1320
tatatctaa                                                            1329
```

<210> SEQ ID NO 23
<211> LENGTH: 439
<212> TYPE: PRT
<213> ORGANISM: Prevotella ruminicola

<400> SEQUENCE: 23

```
Met Ala Lys Glu Tyr Phe Pro Phe Thr Gly Lys Ile Pro Phe Glu Gly
1               5                   10                  15
Lys Asp Ser Lys Asn Val Met Ala Phe His Tyr Tyr Glu Pro Glu Lys
            20                  25                  30
Val Val Met Gly Lys Lys Met Lys Asp Trp Leu Lys Phe Ala Met Ala
        35                  40                  45
Trp Trp His Thr Leu Gly Gly Ala Ser Ala Asp Gln Phe Gly Gly Gln
    50                  55                  60
Thr Arg Ser Tyr Glu Trp Asp Lys Ala Ala Asp Ala Val Gln Arg Ala
65                  70                  75                  80
```

```
          Lys Asp Lys Met Asp Ala Gly Phe Glu Ile Met Asp Lys Leu Gly Ile
                          85                  90                  95

Glu Tyr Phe Cys Phe His Asp Val Asp Leu Val Glu Glu Gly Glu Thr
                      100                 105                 110

Ile Ala Glu Tyr Glu Arg Arg Met Lys Glu Ile Thr Asp Tyr Ala Leu
                      115                 120                 125

Val Lys Met Lys Glu Tyr Pro Asn Ile Lys Leu Leu Trp Gly Thr Ala
                      130                 135                 140

Asn Val Phe Gly Asn Lys Arg Tyr Ala Asn Gly Ala Ser Thr Asn Pro
          145                 150                 155                 160

Asp Phe Asp Val Val Ala Arg Ala Ile Val Gln Ile Lys Asn Ala Ile
                              165                 170                 175

Asp Ala Thr Ile Lys Leu Gly Gly Thr Asn Tyr Val Phe Trp Gly Gly
                          180                 185                 190

Arg Glu Gly Tyr Met Ser Leu Leu Asn Thr Asp Gln Lys Arg Glu Lys
                      195                 200                 205

Glu His Met Ala Thr Met Leu Thr Met Ala Arg Asp Tyr Ala Arg Ala
                      210                 215                 220

Lys Gly Phe Lys Gly Thr Phe Leu Ile Glu Pro Lys Pro Met Glu Pro
          225                 230                 235                 240

Ser Lys His Gln Tyr Asp Val Asp Thr Glu Thr Val Cys Gly Phe Leu
                              245                 250                 255

Arg Ala His Gly Leu Asp Lys Asp Phe Lys Val Asn Ile Glu Val Asn
                          260                 265                 270

His Ala Thr Leu Ala Gly His Thr Phe Glu His Glu Leu Ala Cys Ala
                      275                 280                 285

Val Asp Asn Gly Met Leu Gly Ser Ile Asp Ala Asn Arg Gly Asp Ala
                      290                 295                 300

Gln Asn Gly Trp Asp Thr Asp Gln Phe Pro Ile Asp Asn Phe Glu Leu
          305                 310                 315                 320

Thr Gln Ala Met Leu Glu Ile Ile Arg Asn Gly Gly Leu Gly Asn Gly
                              325                 330                 335

Gly Thr Asn Phe Asp Ala Lys Ile Arg Arg Asn Ser Thr Asp Leu Glu
                          340                 345                 350

Asp Leu Phe Ile Ala His Ile Ser Gly Met Asp Ala Met Ala Arg Ala
                      355                 360                 365

Leu Met Asn Ala Ala Ala Ile Leu Glu Glu Ser Glu Leu Pro Lys Met
                      370                 375                 380

Lys Lys Glu Arg Tyr Ala Ser Phe Asp Asn Gly Ile Gly Lys Asp Phe
          385                 390                 395                 400

Glu Asp Gly Lys Leu Thr Leu Glu Gln Ala Tyr Glu Tyr Gly Lys Lys
                              405                 410                 415

Val Glu Glu Pro Lys Gln Thr Ser Gly Lys Gln Glu Lys Tyr Glu Thr
                          420                 425                 430

Thr Val Ala Leu Tyr Cys Lys
                          435

<210> SEQ ID NO 24
<211> LENGTH: 1320
<212> TYPE: DNA
<213> ORGANISM: Prevotella ruminicola

<400> SEQUENCE: 24
atggctaagg aatacttccc attcactggt aagatcccat tcgaaggtaa ggactctaag      60
```

```
aacgttatgg ctttccacta ctacgaacca gaaaaggttg ttatgggtaa gaagatgaag    120
gactggttga agttcgctat ggcttggtgg cacactttgg gtggtgcttc tgctgaccaa    180
ttcggtggtc aaactagatc ttacgaatgg acaaggctg ctgacgctgt tcaaagagct    240
aaggacaaga tggacgctgg tttcgaaatc atggacaagt tgggtatcga atacttctgt    300
ttccacgacg ttgacttggt tgaagaaggt gaaactatcg ctgaatacga agaagaatg    360
aaggaaatca ctgactacgc tttggttaag atgaaggaat acccaaacat caagttgttg    420
tggggtactg ctaacgtttt cggtaacaag agatacgcta acggtgcttc tactaaccca    480
gacttcgacg ttgttgctag agctatcgtt caaatcaaga cgctatcga cgctactatc    540
aagttgggtg gtactaacta cgttttctgg ggtggtagag aaggttacat gtctttgttg    600
aacactgacc aaaagagaga aaaggaacac atggctacta tgttgactat ggctagagac    660
tacgctagag ctaagggttt caagggtact ttcttgatcg aaccaaagcc aatggaacca    720
tctaagcacc aatacgacgt tgacactgaa actgtttgtg gtttcttgag agctcacggt    780
ttggacaagg acttcaaggt taacatcgaa gttaaccacg ctactttggc tggtcacact    840
ttcgaacacg aattggcttg tgctgttgac aacggtatgt tgggttctat cgacgctaac    900
agaggtgacg ctcaaaacgg ttgggacact gaccaattcc caatcgacaa cttcgaattg    960
actcaagcta tgttggaaat catcagaaac ggtggtttgg gtaacggtgg tactaacttc   1020
gacgctaaga tcagaagaaa ctctactgac ttggaagact tgttcatcgc tcacatctct   1080
ggtatggacg ctatggctag agctttgatg aacgctgctg ctatcttgga agaatctgaa   1140
ttgccaaaga tgaagaagga agatacgct tctttcgaca acggtatcgg taaggacttc   1200
gaagacggta agttgacttt ggaacaagct tacgaatacg gtaagaaggt tgaagaacca   1260
aagcaaactt ctggtaagca agaaaagtac gaaactactg ttgctttgta ctgtaagtga   1320
```

<210> SEQ ID NO 25
<211> LENGTH: 437
<212> TYPE: PRT
<213> ORGANISM: Piromyces equi

<400> SEQUENCE: 25

```
Met Ala Lys Glu Tyr Phe Pro Gln Ile Gln Lys Ile Lys Phe Glu Gly
1               5                  10                  15

Lys Asp Ser Lys Asn Pro Leu Ala Phe His Tyr Tyr Asp Ala Glu Lys
            20                  25                  30

Glu Val Met Gly Lys Lys Met Lys Asp Trp Leu Arg Phe Ala Met Ala
        35                  40                  45

Trp Trp His Thr Leu Cys Ala Glu Gly Ala Asp Gln Phe Gly Gly Gly
    50                  55                  60

Thr Lys Ser Phe Pro Trp Asn Glu Gly Thr Asp Ala Ile Glu Ile Ala
65                  70                  75                  80

Lys Gln Lys Val Asp Ala Gly Phe Glu Ile Met Gln Lys Leu Gly Ile
                85                  90                  95

Pro Tyr Tyr Cys Phe His Asp Val Asp Leu Val Ser Glu Gly Asn Ser
            100                 105                 110

Ile Glu Glu Tyr Glu Ser Asn Leu Lys Ala Val Val Ala Tyr Leu Lys
        115                 120                 125

Glu Lys Gln Lys Glu Thr Gly Ile Lys Leu Leu Trp Ser Thr Ala Asn
    130                 135                 140

Val Phe Gly His Lys Arg Tyr Met Asn Gly Ala Ser Thr Asn Pro Asp
145                 150                 155                 160
```

Phe Asp Val Val Ala Arg Ala Ile Val Gln Ile Lys Asn Ala Ile Asp
            165                 170                 175

Ala Gly Ile Glu Leu Gly Ala Glu Asn Tyr Val Phe Trp Gly Gly Arg
        180                 185                 190

Glu Gly Tyr Met Ser Leu Leu Asn Thr Asp Gln Lys Arg Glu Lys Glu
    195                 200                 205

His Met Ala Thr Met Leu Thr Met Ala Arg Asp Tyr Ala Arg Ser Lys
210                 215                 220

Gly Phe Lys Gly Thr Phe Leu Ile Glu Pro Lys Pro Met Glu Pro Thr
225                 230                 235                 240

Lys His Gln Tyr Asp Val Asp Thr Glu Thr Ala Ile Gly Phe Leu Lys
                245                 250                 255

Ala His Asn Leu Asp Lys Asp Phe Lys Val Asn Ile Glu Val Asn His
            260                 265                 270

Ala Thr Leu Ala Gly His Thr Phe Glu His Glu Leu Ala Cys Ala Val
        275                 280                 285

Asp Ala Gly Met Leu Gly Ser Ile Asp Ala Asn Arg Gly Asp Tyr Gln
    290                 295                 300

Asn Gly Trp Asp Thr Asp Gln Phe Pro Ile Asp Gln Tyr Glu Leu Val
305                 310                 315                 320

Gln Ala Trp Met Glu Ile Ile Arg Gly Gly Phe Val Thr Gly Gly
                325                 330                 335

Thr Asn Phe Asp Ala Lys Thr Arg Arg Asn Ser Thr Asp Leu Glu Asp
            340                 345                 350

Ile Ile Ile Ala His Val Ser Gly Met Asp Ala Met Ala Arg Ala Leu
        355                 360                 365

Glu Asn Ala Ala Lys Leu Leu Gln Glu Ser Pro Tyr Thr Lys Met Lys
    370                 375                 380

Lys Glu Arg Tyr Ala Ser Phe Asp Ser Gly Ile Gly Lys Asp Phe Glu
385                 390                 395                 400

Asp Gly Lys Leu Thr Leu Glu Gln Val Tyr Glu Tyr Gly Lys Lys Asn
                405                 410                 415

Gly Glu Pro Lys Gln Thr Ser Gly Lys Gln Glu Leu Tyr Glu Ala Ile
            420                 425                 430

Val Ala Met Tyr Gln
        435

<210> SEQ ID NO 26
<211> LENGTH: 1314
<212> TYPE: DNA
<213> ORGANISM: Piromyces equi

<400> SEQUENCE: 26
atggccaaag aatacttccc acaaatccaa aagatcaagt tcgaaggtaa ggactctaag      60
aatccattgg ctttccatta ctacgacgcc gaaaagaag ttatgggtaa gaaaatgaag     120
gactggttga gatttgctat ggcttggtgg catactttgt gtgctgaagg tgctgatcaa     180
tttggtggtg gtacaaaatc tttcccatgg aatgaaggta ctgatgccat tgaaattgcc     240
aagcaaaaag ttgatgccgg tttcgaaatt atgcaaaagt tgggtattcc ttactactgc     300
ttccacgatg ttgatttggt ttctgaaggt aactccatcg aagaatacga atctaacttg     360
aaggctgttg tcgcctactt gaaagaaaaa caaaagaaa ccggtattaa gttgttgtgg     420
tctaccgcta atgttttcgg tcacaagaga tatatgaacg gtgcttctac taatccagat     480

```
ttcgatgttg ttgctagagc catcgttcaa atcaagaatg ctattgatgc tggtattgaa      540
ttgggtgccg aaaattatgt tttttggggt ggtagagaag gttacatgtc tttgttgaac      600
accgatcaaa aaagagaaaa agaacacatg gctaccatgt tgactatggc tagagattac      660
gctagatcta agggttttaa gggtactttc ttgatcgaac ctaaacctat ggaacctact      720
aagcaccaat atgatgttga taccgaaacc gctatcggtt ttttgaaggc tcataacttg      780
gataaggact tcaaggttaa catcgaagtc aaccatgcta ctttggctgg tcatactttt      840
gaacatgaat tggcttgtgc tgttgacgca ggtatgttgg gttcaattga tgctaataga      900
ggtgactacc aaaacggttg ggatacagat caattcccaa tcgatcaata cgaattggtt      960
caagcttgga tggaaattat cagaggtggt ggttttgtta ccggtggtac taattttgat     1020
gccaagacta agagaaactc caccgatttg aagatatca ttatcgctca tgtttccggt     1080
atggatgcta tggcaagagc tttggaaaat gctgctaagt tgttacaaga atccccatac     1140
accaagatga gaaagaaag atacgcctct ttcgattccg gtattggtaa ggattttgaa     1200
gatggtaaat tgaccttgga acaagtctac gaatacggta aaaagaacgg tgaacctaag     1260
caaacttctg gtaagcaaga attatacgaa gctatcgttg ccatgtacca atga            1314
```

<210> SEQ ID NO 27
<211> LENGTH: 438
<212> TYPE: PRT
<213> ORGANISM: Clostridium phytofermentans

<400> SEQUENCE: 27

```
Met Lys Asn Tyr Phe Pro Asn Val Pro Glu Val Lys Tyr Glu Gly Pro
1               5                   10                  15

Asn Ser Thr Asn Pro Phe Ala Phe Lys Tyr Tyr Asp Ala Asn Lys Val
            20                  25                  30

Val Ala Gly Lys Thr Met Lys Glu His Cys Arg Phe Ala Leu Ser Trp
        35                  40                  45

Trp His Thr Leu Cys Ala Gly Gly Ala Asp Pro Phe Gly Val Thr Thr
    50                  55                  60

Met Asp Arg Thr Tyr Gly Asn Ile Thr Asp Pro Met Glu Leu Ala Lys
65                  70                  75                  80

Ala Lys Val Asp Ala Gly Phe Glu Leu Met Thr Lys Leu Gly Ile Glu
                85                  90                  95

Phe Phe Cys Phe His Asp Ala Asp Ile Ala Pro Glu Gly Asp Thr Phe
            100                 105                 110

Glu Glu Ser Lys Lys Asn Leu Phe Glu Ile Val Asp Tyr Ile Lys Glu
        115                 120                 125

Lys Met Asp Gln Thr Gly Ile Lys Leu Leu Trp Gly Thr Ala Asn Asn
    130                 135                 140

Phe Ser His Pro Arg Phe Met His Gly Ala Ser Thr Ser Cys Asn Ala
145                 150                 155                 160

Asp Val Phe Ala Tyr Ala Ala Lys Ile Lys Asn Ala Leu Asp Ala
                165                 170                 175

Thr Ile Lys Leu Gly Gly Lys Gly Tyr Val Phe Trp Gly Gly Arg Glu
            180                 185                 190

Gly Tyr Glu Thr Leu Leu Asn Thr Asp Leu Gly Leu Glu Leu Asp Asn
        195                 200                 205

Met Ala Arg Leu Met Lys Met Ala Val Glu Tyr Gly Arg Ala Asn Gly
    210                 215                 220

Phe Asp Gly Asp Phe Tyr Ile Glu Pro Lys Pro Lys Glu Pro Thr Lys
```

```
                    225                 230                 235                 240
His Gln Tyr Asp Phe Asp Thr Ala Thr Val Leu Ala Phe Leu Arg Lys
                245                 250                 255

Tyr Gly Leu Glu Lys Asp Phe Lys Met Asn Ile Glu Ala Asn His Ala
                260                 265                 270

Thr Leu Ala Gly His Thr Phe Glu His Glu Leu Ala Met Ala Arg Val
                275                 280                 285

Asn Gly Ala Phe Gly Ser Val Asp Ala Asn Gln Gly Asp Pro Asn Leu
                290                 295                 300

Gly Trp Asp Thr Asp Gln Phe Pro Thr Asp Val His Ser Ala Thr Leu
305                 310                 315                 320

Ala Met Leu Glu Val Leu Lys Ala Gly Gly Phe Thr Asn Gly Gly Leu
                325                 330                 335

Asn Phe Asp Ala Lys Val Arg Arg Gly Ser Phe Glu Phe Asp Asp Ile
                340                 345                 350

Ala Tyr Gly Tyr Ile Ala Gly Met Asp Thr Phe Ala Leu Gly Leu Ile
                355                 360                 365

Lys Ala Ala Glu Ile Ile Asp Asp Gly Arg Ile Ala Lys Phe Val Asp
                370                 375                 380

Asp Arg Tyr Ala Ser Tyr Lys Thr Gly Ile Gly Lys Ala Ile Val Asp
385                 390                 395                 400

Gly Thr Thr Ser Leu Glu Glu Leu Glu Gln Tyr Val Leu Thr His Ser
                405                 410                 415

Glu Pro Val Met Gln Ser Gly Arg Gln Glu Val Leu Gly Thr Ile Val
                420                 425                 430

Asn Asn Ile Leu Phe Arg
                435

<210> SEQ ID NO 28
<211> LENGTH: 1317
<212> TYPE: DNA
<213> ORGANISM: Clostridium phytofermentans

<400> SEQUENCE: 28
atgaagaact acttcccaaa cgttccagaa gttaagtacg aaggtccaaa ctctactaat    60
ccattcgctt tcaagtacta cgatgccaac aaagttgttg ctggtaagac tatgaaggaa   120
cattgcagat ttgctttgtc ttggtggcat actttgtgtg ctggtggtgc tgatccattt   180
ggtgttacta ctatggatag aacctacggt aacattaccg atccaatgga attggctaaa   240
gctaaagttg atgccggttt tgaattgatg accaagttgg gtattgaatt cttctgcttc   300
catgatgctg atattgctcc agaaggtgat actttcgaag aatccaagaa gaacttgttc   360
gaaatcgtcg actacatcaa agaaagatg gatcaaaccg gtatcaagtt gttgtggggt   420
actgctaaca atttctctca tccaagattc atgcatggtg cttctacatc ttgtaacgct   480 gatgttttg cttatgctgc tgccaagatt aagaatgctt ggatgctac tattaagttg   540 ggtggtaagg gttatgtttt tgggggtggt agagaaggtt acgaaacctt gttgaatact   600
gacttgggtt tggaattgga taacatggct agattgatga gatggcagt tgaatacggt   660 agagctaatg gttttgatgg tgatttctac atcgaaccta gccaaaaga acctactaag   720 caccaatacg attttgatac tgctaccgtt ttggccttct tgagaaagta tggtttggaa   780
aaggacttca agatgaacat cgaagctaac catgctactt tggctggtca tactttgaa   840 catgaattgg caatggctag agttaatggt gcttttggtt ctgttgatgc caatcaaggt   900
```

```
gatcctaatt tgggttggga tactgatcaa tttccaaccg atgttcactc tgctacttta      960
gctatgttgg aagttttgaa ggctggtggt tttactaatg gtggtttgaa tttcgatgcc     1020
aaggttagaa gaggttcctt tgaatttgac gatattgctt acggttacat tgctggtatg     1080 gatactttg ctttgggttt gattaaggcc gccgaaatta ttgatgatgg tagaattgct      1140
aagttcgttg atgatagata cgcctcttac aagactggta ttggtaaagc aatcgttgat     1200
ggtactacct ccttggaaga attgaacaa tatgttttga cccactccga accagttatg      1260
caatctggta gacaagaagt tttggaaacc atcgtcaaca atattttgtt tagatga       1317
```

<210> SEQ ID NO 29
<211> LENGTH: 165
<212> TYPE: PRT
<213> ORGANISM: Saccharomyces cerevisiae

<400> SEQUENCE: 29

```
Met Leu Pro Val Ile Thr Arg Phe Ala Arg Pro Ala Leu Met Ala Ile
1               5                   10                  15

Arg Pro Val Asn Ala Met Gly Val Leu Arg Ala Thr Ser Ile Thr Lys
            20                  25                  30

Arg Leu Tyr His Pro Lys Val Ile Glu His Tyr Thr His Pro Arg Asn
        35                  40                  45

Val Gly Ser Leu Asp Lys Lys Leu Pro Asn Val Gly Thr Gly Leu Val
    50                  55                  60

Gly Ala Pro Ala Cys Gly Asp Val Met Arg Leu Gln Ile Lys Val Asn
65                  70                  75                  80

Asp Ser Thr Gly Val Ile Glu Asp Val Lys Phe Lys Thr Phe Gly Cys
                85                  90                  95

Gly Ser Ala Ile Ala Ser Ser Ser Tyr Met Thr Glu Leu Val Gln Gly
            100                 105                 110

Met Thr Leu Asp Asp Ala Ala Lys Ile Lys Asn Thr Glu Ile Ala Lys
        115                 120                 125

Glu Leu Ser Leu Pro Pro Val Lys Leu His Cys Ser Met Leu Ala Glu
    130                 135                 140

Asp Ala Ile Lys Ala Ala Ile Lys Asp Tyr Lys Ser Lys Arg Asn Thr
145                 150                 155                 160

Pro Thr Met Leu Ser
                165
```

<210> SEQ ID NO 30
<211> LENGTH: 498
<212> TYPE: DNA
<213> ORGANISM: Saccharomyces cerevisiae

<400> SEQUENCE: 30

```
atgcttcctg ttataacgag atttgcaagg cctgctctga tggccatcag acctgtgaat       60
gccatggggg ttttgagagc gaccagcata acgaaaaggc tttatcatcc aaggtcata      120 gagcattata cacatccaag aaacgtcggc tcattagata aaaaattgcc caacgtcggc     180
actggtctag tgggtgcgcc agcgtgcggt gatgtgatga ggttgcagat caaagtcaac     240
gactctactg gcgttattga agatgtcaaa ttcaagactt ttggatgtgg ctccgccatt     300
gcctcctctt catatatgac tgaattggta caggggatga ccttggacga tgcggcaaaa    360
attaagaaca ctgaaattgc taaggagttg agcttgcccc cagtcaagtt gcattgctct    420
atgttagcag aagatgcgat caaggcagct attaaggact acaaatctaa gagaaacact    480
```
ccaaccatgt tatcgtaa                                                498

<210> SEQ ID NO 31
<211> LENGTH: 174
<212> TYPE: PRT
<213> ORGANISM: Saccharomyces cerevisiae

<400> SEQUENCE: 31

Met Ile Lys Arg Ser Leu Ala Ser Leu Val Arg Val Ser Val Met
1               5                   10                  15

Gly Arg Arg Tyr Met Ile Ala Ala Gly Gly Glu Arg Ala Arg Phe
                20                  25                  30

Cys Pro Ala Val Thr Asn Lys Lys Asn His Thr Val Asn Thr Phe Gln
                35                  40                  45

Lys Arg Phe Val Glu Ser Ser Thr Asp Gly Gln Val Val Pro Gln Glu
                50                  55                  60

Val Leu Asn Leu Pro Leu Glu Lys Tyr His Glu Ala Asp Asp Tyr
65                  70                  75                  80

Leu Asp His Leu Leu Asp Ser Leu Glu Glu Leu Ser Glu Ala His Pro
                    85                  90                  95

Asp Cys Ile Pro Asp Val Glu Leu Ser His Gly Val Met Thr Leu Glu
                100                 105                 110

Ile Pro Ala Phe Gly Thr Tyr Val Ile Asn Lys Gln Pro Pro Asn Lys
                115                 120                 125

Gln Ile Trp Leu Ala Ser Pro Leu Ser Gly Pro Asn Arg Phe Asp Leu
130                 135                 140

Leu Asn Gly Glu Trp Val Ser Leu Arg Asn Gly Thr Lys Leu Thr Asp
145                 150                 155                 160

Ile Leu Thr Glu Glu Val Glu Lys Ala Ile Ser Lys Ser Gln
                165                 170

<210> SEQ ID NO 32
<211> LENGTH: 525
<212> TYPE: DNA
<213> ORGANISM: Saccharomyces cerevisiae

<400> SEQUENCE: 32
atgattaagc ggtctctcgc aagtttagtt cgagtcagct ctgtaatggg cagaagatat    60
atgatagcag cggcaggagg agaacgtgcc agatttgtc cagctgtaac aaataaaaag   120
aatcatactg taaatacttt tcagaagaga tttgtagaat cctcgacaga tggtcaagtt   180
gtgcctcaag aagtgttaaa cttaccgctt gaaaaatacc atgaagaggc agatgactac   240
ctagaccatt tactagatag cttagaagaa ctgagtgagg ctcatccgga ctgtatacct   300
gatgtagagc taagccatgg cgtaatgaca ttggaaattc agcttttgg aacgtatgta   360 ataaacaaac agcctccaaa taagcaaatt tggctggcat caccattgtc cgggcctaac   420
agatttgacc ttctcaatgg ggagtgggtt tcgttaagaa atggcacaaa gctaacagat   480
atacttactg aagaagttga aaggccatt tctaaaagcc aataa                   525

<210> SEQ ID NO 33
<211> LENGTH: 497
<212> TYPE: PRT
<213> ORGANISM: Saccharomyces cerevisiae

<400> SEQUENCE: 33

Met Leu Lys Ser Thr Ala Thr Arg Ser Ile Thr Arg Leu Ser Gln Val
1               5                   10                  15

```
Tyr Asn Val Pro Ala Ala Thr Tyr Arg Ala Cys Leu Val Ser Arg Arg
         20                  25                  30

Phe Tyr Ser Pro Pro Ala Ala Gly Val Lys Leu Asp Asp Asn Phe Ser
         35                  40                  45

Leu Glu Thr His Thr Asp Ile Gln Ala Ala Lys Ala Gln Ala Ser
 50                  55                  60

Ala Arg Ala Ser Ala Ser Gly Thr Thr Pro Asp Ala Val Val Ala Ser
 65                  70                  75                  80

Gly Ser Thr Ala Met Ser His Ala Tyr Gln Glu Asn Thr Gly Phe Gly
                 85                  90                  95

Thr Arg Pro Ile Tyr Leu Asp Met Gln Ala Thr Thr Pro Thr Asp Pro
             100                 105                 110

Arg Val Leu Asp Thr Met Leu Lys Phe Tyr Thr Gly Leu Tyr Gly Asn
             115                 120                 125

Pro His Ser Asn Thr His Ser Tyr Gly Trp Glu Thr Asn Thr Ala Val
         130                 135                 140

Glu Asn Ala Arg Ala His Val Ala Lys Met Ile Asn Ala Asp Pro Lys
145                 150                 155                 160

Glu Ile Ile Phe Thr Ser Gly Ala Thr Glu Ser Asn Asn Met Val Leu
                165                 170                 175

Lys Gly Val Pro Arg Phe Tyr Lys Lys Thr Lys Lys His Ile Ile Thr
             180                 185                 190

Thr Arg Thr Glu His Lys Cys Val Leu Glu Ala Ala Arg Ala Met Met
         195                 200                 205

Lys Glu Gly Phe Glu Val Thr Phe Leu Asn Val Asp Asp Gln Gly Leu
210                 215                 220

Ile Asp Leu Lys Glu Leu Glu Asp Ala Ile Arg Pro Asp Thr Cys Leu
225                 230                 235                 240

Val Ser Val Met Ala Val Asn Asn Glu Ile Gly Val Ile Gln Pro Ile
                245                 250                 255

Lys Glu Ile Gly Ala Ile Cys Arg Lys Asn Lys Ile Tyr Phe His Thr
             260                 265                 270

Asp Ala Ala Gln Ala Tyr Gly Lys Ile His Ile Asp Val Asn Glu Met
         275                 280                 285

Asn Ile Asp Leu Leu Ser Ile Ser Ser His Lys Ile Tyr Gly Pro Lys
290                 295                 300

Gly Ile Gly Ala Thr Tyr Val Arg Arg Pro Arg Val Arg Leu Glu
305                 310                 315                 320

Pro Leu Leu Ser Gly Gly Gln Glu Arg Gly Leu Arg Ser Gly Thr
                325                 330                 335

Leu Ala Pro Pro Leu Val Ala Gly Phe Gly Glu Ala Ala Arg Leu Met
             340                 345                 350

Lys Lys Glu Phe Asp Asn Asp Gln Ala His Ile Lys Arg Leu Ser Asp
         355                 360                 365

Lys Leu Val Lys Gly Leu Leu Ser Ala Glu His Thr Thr Leu Asn Gly
370                 375                 380

Ser Pro Asp His Arg Tyr Pro Gly Cys Val Asn Val Ser Phe Ala Tyr
385                 390                 395                 400

Val Glu Gly Glu Ser Leu Leu Met Ala Leu Arg Asp Ile Ala Leu Ser
                405                 410                 415

Ser Gly Ser Ala Cys Thr Ser Ala Ser Leu Glu Pro Ser Tyr Val Leu
             420                 425                 430
```

His Ala Leu Gly Lys Asp Asp Ala Leu Ala His Ser Ser Ile Arg Phe
            435                 440                 445

Gly Ile Gly Arg Phe Ser Thr Glu Glu Glu Val Asp Tyr Val Val Lys
450                 455                 460

Ala Val Ser Asp Arg Val Lys Phe Leu Arg Glu Leu Ser Pro Leu Trp
465                 470                 475                 480

Glu Met Val Gln Glu Gly Ile Asp Leu Asn Ser Ile Lys Trp Ser Gly
                485                 490                 495

His

<210> SEQ ID NO 34
<211> LENGTH: 1494
<212> TYPE: DNA
<213> ORGANISM: Saccharomyces cerevisiae

<400> SEQUENCE: 34

| | | | | |
|---|---|---|---|---|
| atgttgaaat | caactgctac | aagatcgata | acaagattat | ctcaagttta caacgttcca | 60 |
| gcggccacat | atagggcttg | tttggtaagc | aggagattct | attccctcc tgcagcaggc | 120 |
| gtgaagttag | acgacaactt | ctctctggaa | acgcataccg | atattcaggc tgctgcaaag | 180 |
| gcacaggcta | gtgcccgtgc | gagtgcatcc | ggtaccaccc | cagatgctgt agtagcttct | 240 |
| ggtagcactg | caatgagcca | tgcttatcaa | gaaaacacag | gttttggtac tcgtcccata | 300 |
| tatcttgaca | tgcaagccac | tacaccaaca | gaccctaggg | ttttggatac gatgttgaag | 360 |
| ttttatacgg | gactttatgg | taatcctcat | tccaacactc | actcttacgg ttgggaaaca | 420 |
| aatactgctg | tggaaaatgc | tagagctcac | gtagcaaaga | tgatcaatgc cgaccccaag | 480 |
| gaaataatat | tcacttcggg | agcgaccgaa | tctaataata | tggttcttaa gggtgtccca | 540 |
| agattttata | agaagactaa | gaaacacatc | atcaccacta | gaacggaaca caagtgtgtc | 600 |
| ttggaagccg | cacgggccat | gatgaaggag | ggatttgaag | tcactttcct aaatgtggac | 660 |
| gatcaaggtc | ttatcgattt | gaaggaattg | gaagatgcca | ttagaccaga tacctgtctc | 720 |
| gtctctgtga | tggctgtcaa | taatgaaatc | ggtgtcattc | aacctattaa agaaattggt | 780 |
| gcaatttgta | gaaagaataa | gatctacttt | cataccgacg | ccgcacaagc ctatggtaag | 840 |
| attcacattg | atgtcaatga | aatgaacatt | gatttactat | caatttcttc tcacaagatt | 900 |
| tacggtccaa | agggaatagg | tgccacctat | gtaagaagga | gaccaagagt tagattagaa | 960 |
| cctttactat | ccggtggtgg | ccaagagaga | ggattgagat | ctggtacttt ggccccccca | 1020 |
| ttggtagcgg | gatttggtga | agctgcgaga | ttgatgaaga | agaaatttga caacgaccaa | 1080 |
| gctcacatca | aaagactatc | cgataaatta | gtcaaaggtc | tattatccgc tgaacatacc | 1140 |
| acgttgaacg | gatctccaga | tcatcgttat | ccagggtgtg | ttaacgtttc tttcgcctac | 1200 |
| gtggaaggag | aatctttatt | gatggcacta | agggatatcg | cattatcctc gggttcagcc | 1260 |
| tgtacatctg | cttccctaga | accttcttat | gttttacatg | cgctgggtaa ggatgatgca | 1320 |
| ttagcccatt | cttccatcag | atttggtatt | ggtagattta | gtactgaaga ggaggtcgac | 1380 |
| tacgtcgtta | aggccgtttc | tgacagagta | aaattcttga | gggaactttc accattatgg | 1440 |
| gaaatggttc | aagaaggtat | tgacttaaac | tccatcaaat | ggtcaggtca ttga | 1494 |

<210> SEQ ID NO 35
<211> LENGTH: 438
<212> TYPE: PRT
<213> ORGANISM: Artificial Sequence
<220> FEATURE:
<223> OTHER INFORMATION: Description of Artificial Sequence: Synthetic

```
        polypeptide
<220> FEATURE:
<223> OTHER INFORMATION: CX386 chimeric xylose isomerase

<400> SEQUENCE: 35

Met Ala Lys Glu Tyr Phe Pro Phe Thr Gly Lys Ile Pro Phe Glu Gly
1               5                   10                  15

Lys Asp Ser Lys Asn Val Met Ala Phe His Tyr Tyr Glu Pro Glu Lys
            20                  25                  30

Val Val Met Gly Lys Lys Met Lys Asp Trp Leu Lys Phe Ala Met Ala
        35                  40                  45

Trp Trp His Thr Leu Gly Gly Ala Ser Ala Asp Gln Phe Gly Gly Gln
    50                  55                  60

Thr Arg Ser Tyr Glu Trp Asp Lys Ala Ala Asp Ala Val Gln Arg Ala
65                  70                  75                  80

Lys Asp Lys Met Asp Ala Gly Phe Glu Ile Met Asp Lys Leu Gly Ile
                85                  90                  95

Glu Tyr Phe Cys Phe His Asp Val Asp Leu Val Glu Glu Gly Glu Thr
            100                 105                 110

Ile Ala Glu Tyr Glu Arg Arg Met Lys Glu Ile Thr Asp Tyr Ala Leu
        115                 120                 125

Val Lys Met Lys Glu Tyr Pro Asn Ile Lys Leu Leu Trp Gly Thr Ala
    130                 135                 140

Asn Val Phe Ser Asn Pro Arg Tyr Met Asn Gly Ala Ala Thr Asn Pro
145                 150                 155                 160

Asp Phe Ala Ala Val Ala Tyr Ala Gly Thr Gln Val Lys Asn Ser Leu
                165                 170                 175

Asp Ala Thr Ile Ala Leu Gly Gly Glu Asn Tyr Val Phe Trp Gly Gly
            180                 185                 190

Arg Glu Gly Tyr Met Ser Leu Leu Asn Thr Asn Met Lys Arg Glu Lys
        195                 200                 205

Asp His Leu Ala Met Met Leu Thr Met Ala Arg Asp Tyr Gly Arg Lys
    210                 215                 220

Asn Gly Phe Lys Gly Thr Phe Leu Ile Glu Pro Lys Pro Met Glu Pro
225                 230                 235                 240

Thr Lys His Gln Tyr Asp Val Asp Ser Glu Thr Val Ile Gly Phe Leu
                245                 250                 255

Arg His Tyr Gly Leu Asp Lys Asp Phe Ala Leu Asn Ile Glu Val Asn
            260                 265                 270

His Ala Thr Leu Ala Gly His Thr Phe Glu His Glu Leu Gln Ala Ala
        275                 280                 285

Ala Asp Ala Gly Met Leu Cys Ser Ile Asp Ala Asn Arg Gly Asp Tyr
    290                 295                 300

Gln Asn Gly Trp Asp Thr Asp Gln Phe Pro Met Asp Ile Tyr Glu Leu
305                 310                 315                 320

Ala Gln Ala Trp Leu Val Ile Leu Glu Gly Gly Leu Thr Thr Gly
                325                 330                 335

Gly Thr Asn Phe Asp Ala Lys Thr Arg Arg Asn Ser Thr Asp Leu Glu
            340                 345                 350

Asp Ile Phe Ile Ala His Ile Gly Gly Met Asp Ala Phe Ala Arg Ala
        355                 360                 365

Leu Met Ile Ala Ala Asp Ile Leu Glu Asn Ser Asp Tyr Arg Lys Met
    370                 375                 380

Arg Ala Glu Arg Tyr Ala Ser Phe Asp Ala Gly Glu Gly Lys Ala Phe
```

```
                385                 390                 395                 400
Glu Asp Gly Lys Leu Thr Leu Glu Asp Leu Arg Thr Ile Ala Leu Arg
                    405                 410                 415

Asp Gly Glu Pro Lys Gln Ile Ser Gly Lys Gln Glu Leu Tyr Glu Met
                420                 425                 430

Ile Val Asn Leu His Ile
                435

<210> SEQ ID NO 36
<211> LENGTH: 1317
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CX386 chimeric xylose isomerase

<400> SEQUENCE: 36
atggctaagg aatacttccc attcactggt aagatcccat cgaaggtaa ggactctaag      60 aacgttatgg ctttccacta ctacgaacca gaaaaggttg ttatgggtaa gaagatgaag    120
gactggttga gttcgctat ggcttggtgg cacactttgg gtggtgcttc tgctgaccaa    180
ttcggtggtc aaactagatc ttacgaatgg gacaaggctg ctgacgctgt caaagagct    240 aaggacaaga tggacgctgg tttcgaaatc atggacaagt gggtatcga atacttctgt   300 ttccacgacg ttgacttggt tgaagaaggt gaaactatcg ctgaatacga agaagaatg    360 aaggaaatca ctgactacgc tttggttaag atgaaggaat acccaaacat caagttgttg    420
tggggtactg ctaatgtttt ctccaaccca agatatatga acggtgctgc tactaatcca    480
gattttgctg ctgttgctta tgctggtact caagttaaga actctttgga tgctaccatt    540
gctttgggtg gtgaaaatta tgttttctgg ggtggtagag aaggttacat gtctttgttg    600
aacaccaaca tgaagagaga aaaggatcat ttggccatga tgttgactat ggctagagat    660
tacggtagaa agaatggttt caagggtact ttcttgatcg aacctaaacc tatggaacct    720
actaagcacc aatacgatgt tgattccgaa accgttatcg gtttcttgag acattacggt    780
ttggataagg atttcgcctt gaacatcgaa gttaaccatg ctactttggc tggtcatact    840
ttcgaacatg aattgcaagc tgctgctgat gctggtatgt tgtgttctat tgatgctaac    900
agaggtgact accaaaatgg ttgggatact gatcaattcc caatggatat ctacgaattg    960
gctcaagctt ggttggttat tttggaaggt ggtggtttga ctactggtgg tactaatttt   1020
gatgccaaga ccagaagaaa ctccactgat ttggaagaca tcttcattgc ccatatcggt    1080
ggtatggatg cttttgctag agctttgatg attgctgccg atattttgga aaactccgac    1140
tacagaaaga tgagagctga agatacgct tcttttgatg ctggtgaagg taaggctttc   1200
gaagatggta aattgacctt ggaagatttg agaaccattg ctttgagaga tggtgaacct    1260
aagcaaattt ccggtaagca agaattatac gaaatgatcg tcaacttgca catctaa      1317

<210> SEQ ID NO 37
<211> LENGTH: 438
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CX1224 chimeric xylose isomerase
```

<400> SEQUENCE: 37

```
Met Thr Lys Glu Tyr Phe Pro Phe Thr Gly Lys Ile Pro Tyr Glu Gly
1               5                   10                  15
Lys Asp Ser Asn Asn Val Met Ala Phe His Tyr Tyr Glu Pro Glu Lys
            20                  25                  30
Val Val Met Gly Lys Lys Met Lys Asp Trp Leu Lys Phe Ala Met Ala
        35                  40                  45
Trp Trp His Thr Leu Gly Gly Ala Ser Ala Asp Gln Phe Gly Gly Gln
    50                  55                  60
Thr Arg Ser Tyr Glu Trp Asp Lys Ala Ala Asp Ala Val Gln Arg Ala
65                  70                  75                  80
Lys Asp Lys Met Asp Ala Gly Phe Glu Ile Met Asp Lys Leu Gly Ile
                85                  90                  95
Glu Tyr Phe Cys Phe His Asp Val Asp Leu Val Glu Glu Gly Glu Thr
            100                 105                 110
Ile Ala Glu Tyr Glu Arg Arg Met Lys Glu Ile Thr Asp Tyr Ala Leu
        115                 120                 125
Val Lys Met Lys Glu Tyr Pro Asn Ile Lys Leu Leu Trp Gly Thr Ala
    130                 135                 140
Asn Val Phe Ser Asn Pro Arg Tyr Met Asn Gly Ala Ala Thr Asn Pro
145                 150                 155                 160
Asp Phe Ala Ala Val Ala Tyr Ala Gly Thr Gln Val Lys Asn Ser Leu
                165                 170                 175
Asp Ala Thr Ile Ala Leu Gly Gly Glu Asn Tyr Val Phe Trp Gly Gly
            180                 185                 190
Arg Glu Gly Tyr Met Ser Leu Leu Asn Thr Asn Met Lys Arg Glu Lys
        195                 200                 205
Asp His Leu Ala Met Met Leu Thr Met Ala Arg Asp Tyr Gly Arg Lys
    210                 215                 220
Asn Gly Phe Lys Gly Thr Phe Leu Ile Glu Pro Lys Pro Met Glu Pro
225                 230                 235                 240
Thr Lys His Gln Tyr Asp Val Asp Ser Glu Thr Val Ile Gly Phe Leu
                245                 250                 255
Arg His Tyr Gly Leu Asp Lys Asp Phe Ala Leu Asn Ile Glu Val Asn
            260                 265                 270
His Ala Thr Leu Ala Gly His Thr Phe Glu His Glu Leu Gln Ala Ala
        275                 280                 285
Ala Asp Ala Gly Met Leu Cys Ser Ile Asp Ala Asn Arg Gly Asp Tyr
    290                 295                 300
Gln Asn Gly Trp Asp Thr Asp Gln Phe Pro Met Asp Ile Tyr Glu Leu
305                 310                 315                 320
Ala Gln Ala Trp Leu Val Ile Leu Glu Asn Gly Gly Leu Thr Thr Gly
                325                 330                 335
Gly Thr Asn Phe Asp Ala Lys Thr Arg Arg Asn Ser Thr Asp Leu Glu
            340                 345                 350
Asp Ile Phe Ile Ala His Ile Gly Gly Met Asp Ala Phe Ala Arg Ala
        355                 360                 365
Leu Met Ile Ala Ala Asp Ile Leu Glu Asn Ser Asp Tyr Arg Lys Met
    370                 375                 380
Arg Ala Glu Arg Tyr Gly Thr Phe Asp Ala Gly Glu Gly Lys Ala Phe
385                 390                 395                 400
Glu Glu Gly Gln Leu Thr Leu Glu Asp Leu Arg Thr Ile Ala Leu Arg
                405                 410                 415
```

Asp Gly Asp Pro Lys Lys Ile Ser Gly Lys Gln Glu Leu Tyr Glu Met
            420                 425                 430

Ile Val Asn Leu His Ile
        435

<210> SEQ ID NO 38
<211> LENGTH: 1317
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CX1224 chimeric xylose isomerase

<400> SEQUENCE: 38

```
atgactaagg aatacttccc attcactggt aagatcccat acgaaggtaa ggactctaat     60
aacgttatgg ctttccacta ctacgaacca gaaaaggttg ttatgggtaa gaagatgaag    120
gactggttga agttcgctat ggcttggtgg cacactttgg gtggtgcttc tgctgaccaa    180
ttcggtggtc aaactagatc ttacgaatgg acaaggctg ctgacgctgt tcaaagagct    240
aaggacaaga tggacgctgg tttcgaaatc atggacaagt gggtatcga atacttctgt    300
ttccacgacg ttgacttggt tgaagaaggt gaaactatcg ctgaatacga agaagaatg    360
aaggaaatca ctgactacgc tttggttaag atgaaggaat acccaaacat caagttgttg    420
tggggtactg ctaatgtttt ctccaaccca agatatatga acggtgctgc tactaatcca    480
gattttgctg ctgttgctta tgctggtact caagttaaga actctttgga tgctaccatt    540
gctttgggtg gtgaaaatta tgttttctgg ggtggtagag aaggttacat gtctttgttg    600
aacaccaaca tgaagagaga aaaggatcat ttggccatga tgttgactat ggctagagat    660
tacggtagaa agaatggttt caagggtact ttcttgatcg aacctaaacc tatggaacct    720
actaagcacc aatacgatgt tgattccgaa accgttatcg gtttcttgag acattacggt    780
ttggataagg atttcgcctt gaacatcgaa gttaaccatg ctactttggc tggtcatact    840
ttcgaacatg aattgcaagc tgctgctgat gctggtatgt gtgttctat tgatgctaac    900
agaggtgact accaaaatgg ttgggatact gatcaattcc caatggatat ctacgaattg    960
gctcaagctt ggttggttat tttggaaaac ggtggtttga ctactggtgg tactaatttt   1020
gatgccaaga ccagaagaaa ctccactgat ttggaagaca tcttcattgc ccatatcggt   1080
ggtatggatg cttttgctag agctttgatg attgctgccg atattttgga aaactccgac   1140
tacagaaaga tgagagctga agatacggt acttttgatg ctggtgaagg taaggctttc   1200
gaagaaggtc aattgacctt ggaagatttg agaaccattg ctttgagaga tggtgatcct   1260
aagaagattt ccggtaagca agaattatac gaaatgatcg tcaacttgca catctaa     1317
```

<210> SEQ ID NO 39
<211> LENGTH: 457
<212> TYPE: PRT
<213> ORGANISM: Lachnoanaerobaculum saburreum

<400> SEQUENCE: 39

Met Lys Thr Lys Asn Asn Ile Ile Cys Thr Ile Ala Leu Lys Gly Asp
1               5                   10                  15

Ile Phe Met Lys Glu Phe Phe Pro Gly Ile Ser Pro Val Lys Phe Glu
            20                  25                  30

Gly Arg Asp Ser Lys Asn Pro Leu Ser Phe Lys Tyr Tyr Asp Ala Lys

```
                35                  40                  45
Arg Val Ile Met Gly Lys Thr Met Glu Glu His Leu Ser Phe Ala Met
 50                  55                  60
Ala Trp Trp His Asn Leu Cys Ala Cys Gly Val Asp Met Phe Gly Gln
 65                  70                  75                  80
Gly Thr Val Asp Lys Ser Phe Gly Glu Ser Ser Gly Thr Met Glu His
                 85                  90                  95
Ala Arg Ala Lys Val Asp Ala Gly Ile Glu Phe Met Lys Lys Leu Gly
                100                 105                 110
Ile Lys Tyr Tyr Cys Phe His Asp Thr Asp Ile Val Pro Glu Asp Gln
                115                 120                 125
Glu Asp Ile Asn Val Thr Asn Ala Arg Leu Asp Glu Ile Thr Asp Tyr
                130                 135                 140
Ile Leu Glu Lys Thr Lys Asp Thr Asp Ile Lys Cys Leu Trp Thr Thr
145                 150                 155                 160
Cys Asn Met Phe Ser Asn Pro Arg Phe Met Asn Gly Ala Gly Ser Ser
                165                 170                 175
Asn Ser Ala Asp Val Phe Cys Phe Ala Ala Gln Ala Lys Lys Gly
                180                 185                 190
Leu Glu Asn Ala Val Lys Leu Gly Ala Lys Gly Phe Val Phe Trp Gly
                195                 200                 205
Gly Arg Glu Gly Tyr Glu Thr Leu Leu Asn Thr Asp Met Lys Leu Glu
                210                 215                 220
Glu Glu Asn Ile Ala Thr Leu Phe Thr Met Cys Arg Asp Tyr Gly Arg
225                 230                 235                 240
Ser Ile Gly Phe Met Gly Asp Phe Tyr Ile Glu Pro Lys Pro Lys Glu
                245                 250                 255
Pro Met Lys His Gln Tyr Asp Phe Asp Ala Ala Thr Ala Ile Gly Phe
                260                 265                 270
Leu Arg Lys Tyr Gly Leu Asp Lys Asp Phe Lys Leu Asn Ile Glu Ala
                275                 280                 285
Asn His Ala Thr Leu Ala Gly His Thr Phe Gln His Glu Leu Arg Val
                290                 295                 300
Cys Ala Val Asn Gly Met Met Gly Ser Val Asp Ala Asn Gln Gly Asp
305                 310                 315                 320
Thr Leu Leu Gly Trp Asp Thr Asp Gln Phe Pro Thr Asn Val Tyr Asp
                325                 330                 335
Thr Thr Leu Ala Met Tyr Glu Ile Leu Lys Ala Gly Gly Leu Arg Gly
                340                 345                 350
Gly Leu Asn Phe Asp Ser Lys Asn Arg Arg Pro Ser Asn Thr Ala Asp
                355                 360                 365
Asp Met Phe Tyr Gly Phe Ile Ala Gly Met Asp Thr Phe Ala Leu Gly
                370                 375                 380
Leu Ile Lys Ala Ala Glu Ile Ile Glu Asp Gly Arg Ile Asp Asp Phe
385                 390                 395                 400
Val Lys Glu Arg Tyr Ala Ser Tyr Asn Ser Gly Ile Gly Lys Ile
                405                 410                 415
Arg Asn Arg Lys Val Thr Leu Ile Glu Cys Ala Glu Tyr Ala Ala Lys
                420                 425                 430
Leu Lys Lys Pro Glu Leu Pro Glu Ser Gly Arg Gln Glu Tyr Leu Glu
                435                 440                 445
Ser Val Val Asn Asn Ile Leu Phe Gly
450                 455
```

<210> SEQ ID NO 40
<211> LENGTH: 1374
<212> TYPE: DNA
<213> ORGANISM: Lachnoanaerobaculum saburreum

<400> SEQUENCE: 40

```
atgaagacta agaacaacat catctgtact atcgctttga agggtgacat cttcatgaag      60
gaattcttcc caggtatctc tccagttaag ttcgaaggta gagactctaa gaacccattg     120
tctttcaagt actacgacgc taagagagtt atcatgggta agactatgga agaacacttg     180
tctttcgcta tggcttggtg gcacaacttg tgtgcttgtg tgttgacat gttcggtcaa      240
ggtactgttg acaagtcttt cggtgaatct tctggtacta tggaacacgc tagagctaag     300
gttgacgctg gtatcgaatt catgaagaag ttgggtatca agtactactg tttccacgac     360
actgacatcg ttccagaaga ccaagaagac atcaacgtta ctaacgctag attggacgaa     420
atcactgact acatcttgga aaagactaag gacactgaca tcaagtgttt gtggactact     480
tgtaacatgt tctctaaccc aagattcatg aacggtgctg gttcttctaa ctctgctgac     540
gttttctgtt tcgctgctgc tcaagctaag aagggtttgg aaaacgctgt taagttgggt     600
gctaagggtt tcgttttctg gggtggtaga gaaggttacg aaactttgtt gaacactgac     660
atgaagttgg aagaagaaaa catcgctact ttgttcacta tgtgtagaga ctacggtaga     720
tctatcggtt tcatgggtga cttctacatc gaaccaaagc caaggaacc aatgaagcac     780
caatacgact cgacgctgc tactgctatc ggtttcttga aaagtacgg tttggacaag     840
gacttcaagt tgaacatcga agctaaccac gctactttgg ctggtcacac tttccaacac     900
gaattgagag tttgtgctgt taacggtatg atgggttctg ttgacgctaa ccaaggtgac     960
actttgttgg gttgggacac tgaccaattc ccaactaacg tttacgacac tactttggct    1020
atgtacgaaa tcttgaaggc tggtggtttg agaggtggtt tgaacttcga ctctaagaac    1080
agaagaccat ctaacactgc tgacgacatg ttctacggtt tcatcgctgg tatggacact    1140
ttcgctttgg gtttgatcaa ggctgctgaa atcatcgaag acggtagaat cgacgacttc    1200
gttaaggaaa gatacgcttc ttacaactct ggtatcggta gaagatcag aaacagaaag    1260
gttactttga tcgaatgtgc tgaatacgct gctaagttga agaagccaga attgccagaa    1320
tctggtagac aagaatactt ggaatctgtt gttaacaaca tcttgttcgg ttga          1374
```

<210> SEQ ID NO 41
<211> LENGTH: 439
<212> TYPE: PRT
<213> ORGANISM: Lactobacillus xylosus

<400> SEQUENCE: 41

```
Met Ala Tyr Phe Asn Asp Ile Ala Pro Ile Lys Tyr Glu Gly Thr Lys
1               5                   10                  15

Thr Lys Asn Met Phe Ala Phe Arg His Tyr Asn Pro Glu Glu Val Val
            20                  25                  30

Ala Gly Lys Thr Met Glu Glu Gln Leu His Phe Ala Leu Ala Phe Trp
        35                  40                  45

His Thr Ile Thr Met Asp Gly Ser Asp Pro Phe Gly Gly Ala Thr Met
    50                  55                  60

Glu Arg Pro Trp Asp Leu Glu Gly Gly Ser Glu Leu Asp Arg Ala His
65                  70                  75                  80

Arg Arg Val Asp Ala Phe Phe Glu Ile Ala Glu Lys Leu Gly Val Lys
```

|  |  |  |  | 85 |  |  |  |  | 90 |  |  |  |  | 95 |  |  |
|---|---|---|---|---|---|---|---|---|---|---|---|---|---|---|---|---|

Tyr Tyr Cys Phe His Asp Ile Asp Ile Ala Pro Thr Gly Asn Ser Leu
                100                 105                 110

Lys Glu Phe Tyr Ala Asn Leu Asp Glu Ile Thr Asp His Leu Leu Glu
        115                 120                 125

Lys Gln Lys Ala Thr Gly Ile Lys Leu Leu Trp Asn Thr Ala Asn Met
130                 135                 140

Phe Ser Asn Pro Arg Tyr Met Asn Gly Val Ser Thr Ser Asn Arg Ala
145                 150                 155                 160

Glu Val Phe Ala Tyr Gly Ala Ala Gln Val Lys Lys Gly Leu Glu Leu
                165                 170                 175

Ser Lys Lys Leu Gly Gly Glu Asn Tyr Val Phe Trp Gly Gly Arg Glu
            180                 185                 190

Gly Tyr Glu Ser Leu Leu Asn Thr Asp Met Gly Leu Glu Met Asp His
        195                 200                 205

Met Ala Lys Phe Phe His Leu Ala Ile Asp Tyr Ala Lys Ser Ile Asn
    210                 215                 220

His Leu Pro Ile Phe Leu Ile Glu Pro Lys Pro Lys Glu Pro Met Thr
225                 230                 235                 240

His Gln Tyr Asp Phe Asp Ser Ala Thr Ala Leu Ala Phe Leu Gln Lys
                245                 250                 255

Tyr Asp Leu Asp Lys Tyr Phe Lys Leu Asn Leu Glu Thr Asn His Ala
            260                 265                 270

Trp Leu Ala Gly His Thr Phe Glu His Glu Leu Asn Thr Ala Arg Thr
        275                 280                 285

Phe Asn Ala Leu Gly Ser Ile Asp Ala Asn Gln Gly Asn Tyr Leu Leu
    290                 295                 300

Gly Trp Asp Thr Asp Glu Phe Pro Thr Leu Val Ile Asp Ile Thr Leu
305                 310                 315                 320

Ala Met His Gln Ile Leu Leu Asn Gly Gly Leu Gly Lys Gly Gly Ile
                325                 330                 335

Asn Phe Asp Ala Lys Val Arg Arg Thr Ser Phe Lys Ala Glu Asp Leu
            340                 345                 350

Ile Leu Ala His Ile Ala Gly Met Asp Thr Tyr Ala Arg Ala Leu Lys
        355                 360                 365

Gly Ala Ala Ile Ile Glu Asp Lys Phe Leu Ser Asp Ile Val Asp
    370                 375                 380

Glu Arg Tyr Ser Ser Tyr Arg Asn Thr Glu Val Gly Gln Ser Ile Glu
385                 390                 395                 400

Asn Gly Thr Ala Thr Phe Glu Ser Leu Ala Ala Phe Ala Leu Glu Tyr
                405                 410                 415

Gly Asp Asp Ile Glu Leu Asp Ser Asn His Leu Glu Tyr Ile Lys Ser
            420                 425                 430

Val Leu Asn Asp Tyr Leu Val
        435

<210> SEQ ID NO 42
<211> LENGTH: 1320
<212> TYPE: DNA
<213> ORGANISM: Lactobacillus xylosus

<400> SEQUENCE: 42
atggcttact tcaacgacat cgctccaatc aagtacgaag gtactaagac taagaacatg    60
ttcgctttca gacactacaa cccagaagaa gttgttgctg gtaagactat ggaagaacaa   120

```
ttgcacttcg ctttggcttt ctggcacact atcactatgg acggttctga cccattcggt    180
ggtgctacta tggaaagacc atgggacttg gaaggtggtt ctgaattgga cagagctcac    240
agaagagttg acgctttctt cgaaatcgct gaaaagttgg gtgttaagta ctactgtttc    300
cacgacatcg acatcgctcc aactggtaac tctttgaagg aattctacgc taacttggac    360
gaaatcactg accacttgtt ggaaaagcaa aaggctactg gtatcaagtt gttgtggaac    420
actgctaaca tgttctctaa cccaagatac atgaacggtg tttctacttc taacagagct    480
gaagttttcg cttacggtgc tgctcaagtt aagaagggtt tggaattgtc taagaagttg    540
ggtggtgaaa actacgtttt ctggggtggt agagaaggtt acgaatcttt gttgaacact    600
gacatgggtt tggaaatgga ccacatggct aagttcttcc acttggctat cgactacgct    660
aagtctatca accacttgcc aatcttcttg atcgaaccaa agccaaagga accaatgact    720
caccaatacg acttcgactc tgctactgct ttggctttct tgcaaaagta cgacttggac    780
aagtacttca agttgaactt ggaaactaac cacgcttggt tggctggtca cactttcgaa    840
cacgaattga acactgctag aactttcaac gctttgggtt ctatcgacgc taaccaaggt    900
aactacttgt tggggttggga cactgacgaa ttcccaactt tggttatcga catcactttg    960
gctatgcacc aaatcttgtt gaacggtggt ttgggtaagg gtggtatcaa cttcgacgct   1020
aaggttagaa gaacttcttt caaggctgaa gacttgatct tggctcacat cgctggtatg   1080
gacacttacg ctagagcttt gaagggtgct gctgctatca tcgaagacaa gttcttgtct   1140
gacatcgttg acgaaagata ctcttcttac agaaacactg aagttggtca atctatcgaa   1200
aacggtactg ctactttcga atctttggct gctttcgctt tggaatacgg tgacgacatc   1260
gaattggact ctaaccactt ggaatacatc aagtctgttt tgaacgacta cttggtttga   1320
```

MUTATIONS IN IRON-SULFUR CLUSTER PROTEINS THAT IMPROVE XYLOSE UTILIZATION

CROSS-REFERENCE TO RELATED APPLICATIONS

This application is a continuation of U.S. patent application Ser. No. 14/821,955 filed on Aug. 10, 2015, which claims priority from U.S. patent application Ser. No. 62/035,748 filed on Aug. 11, 2014, which are incorporated by reference in their entirety.

FEDERALLY SPONSORED RESEARCH OR DEVELOPMENT

This invention was funded, in part, by the United States government under a grant with the Department of Energy, Office of Energy Efficiency and Renewable Energy, Bioenergy Technologies Office, Award No. DE-FC36-08G018103 to Mascoma and FWP#CEEB007 to Oak Ridge National Laboratory. This invention was also funded, in part, by the Bioenergy Science Center, Oak Ridge National Laboratory, a U.S. Department of Energy Bioenergy Research Center supported by the Office of Biological and Environmental Research, under contract DE-P502-06ER64304. The government has certain rights in the invention.

REFERENCE TO SEQUENCE LISTING SUBMITTED ELECTRONICALLY VIA EFS-WEB

The content of the electronically submitted sequence listing (Name: 115235-153CorrectedSeqList: Size: 114,676 bytes; Date of Creation: May 7, 2018) is in accordance with 37 C.F.R. § 1.821-1.825, and is incorporated by reference in its entirety.

FIELD OF THE INVENTION

The field of the invention generally relates to engineered host cells comprising (a) one or more mutations in one or more endogenous genes encoding a protein associated with iron metabolism; and (b) at least one gene encoding a polypeptide having xylose isomerase activity; and methods of fermenting cellulosic biomass to produce biofuels, including ethanol.

BACKGROUND OF THE INVENTION

*Saccharomyces cerevisiae* is the primary biocatalyst used in the commercial production of "first generation" fuel ethanol from sugar based substrates such as corn, sugarcane, and sugarbeet. Second generation ethanol production, also known as cellulosic ethanol production, extends the carbohydrate source to more complex polysaccharides, such as cellulose and hemicellulose, which make up a significant portion of most plant cell walls and therefore most plant material.

Feedstocks commercially considered for second generation ethanol production include wood, agriculture residues such as corn stover and wheat straw, sugarcane bagasse and purpose grown materials such as switchgrass. The cellulose and hemicellose must be hydrolyzed to monomeric sugars before fermentation using either mechanical/chemical means and/or enzymatic hydrolysis. The liberated monomeric sugars include glucose, xylose, galactose, mannose, and arabinose with glucose and xylose constituting more than 75% of the monomeric sugars in most feedstocks. For cellulosic ethanol production to be economically viable and compete with first generation ethanol, the biocatalyst must be able to convert the majority, if not all, of the available sugars into ethanol.

*S. cerevisiae* is the preferred organism for first generation ethanol production due to its robustness, high yield, and many years of safe use. However, naturally occurring *S. cerevisiae* is unable to ferment xylose into ethanol. For *S. cerevisiae* to be a viable biocatalyst for second generation ethanol production, it must be able to ferment xylose.

There are two metabolic pathways of xylose fermentation that have been demonstrated in *S. cerevisiae*. The pathways differ primarily in the conversion of xylose to xylulose. In the first pathway, the XR-XDH pathway, a xylose reductase (XR) converts xylose to xylitol, which is subsequently converted to xylulose by a xylitol dehydrogenase (XDH). The XR and XDH enzyme pairs tested to date differ in required cofactor, NADH and NADPH, leading to difficulties achieving redox balance. The second commonly tried pathway converts xylose directly to xylulose using a xylose isomerase (XI) with no redox cofactor requirements. XIs from both bacterial and fungal systems have been successfully utilized in *S. cerevisiae*. Both pathways utilize the same downstream metabolic engineering: up regulation of the native xylulose kinase (XKS1) and four genes of the pentose phosphate pathway, specifically ribulose-phosphate 3-epimerase (RPE1), ribose-5-phosphate ketol-isomerase (RKI1), transaldolase (TAL1), and transketolase (TKL1) (FIG. 1). Use of the XI pathway also commonly entails deletion of the native aldose reductase gene (GRE3) to eliminate product lost to xylitol formation.

Xylose isomerases are known to have several metal ion binding sites, which allows XIs to bind metal ions such as manganese, cobalt, and magnesium. See, e.g., Chang et al., "Crystal Structures of Thermostable Xylose Isomerases from *Thermus caldophilus* and *Thermus thermophilus*: Possible Structural Determinants of Thermostability," *J. Mol. Biol* 288:623-34 (1999). There is some indication that XIs may also bind iron cations (Fe+), but Fe+ is usually not the preferred or optimal divalent cation. However, intracellular iron regulation and metabolism is known to be a critical function for eukaryotic cells due to iron's role as a redox-active protein cofactor. See, e.g., Outten and Albetel, "Iron sensing and regulation in *Saccharomyces cerevisiae*: Ironing out the mechanistic details," *Curr. Op. Microbiol.* 16:662-68 (2013). Intracellular iron levels are primarily controlled by the iron-sensing transcriptional activators Aft1 and Aft2 in *S. cerevisiae*. Iron-sulfur (Fe/S) clusters are essential for transcriptional control by Aft1/2 and Yap5 during iron sufficiency. Under sufficient iron levels, Fe/S clusters are synthesized in the mitochondria through the integration of iron, sulfur, and redox control pathways. The Fe/S clusters interact with Grx3, Grx4, Fra1, and Fra2 to inactivate Aft1/2, leading to down regulation of Aft1/2 target genes. Fe/S clusters also are known to activate the expression of Yap5 target genes, including CCC1. Ccc1 stimulates the import of iron and its sequestration in the vacuole.

BRIEF SUMMARY OF THE INVENTION

Aspects of the invention are directed to engineered host cells comprising (a) one or more mutations in one or more endogenous genes encoding a protein associated with iron metabolism; and (b) at least one gene encoding a polypeptide having xylose isomerase activity, and methods of their use are described herein.

In some embodiments, the host cell heterologously expresses one or more polypeptides capable of converting xylose to xylulose. In some embodiments, the one or more heterologously expressed polypeptide is a xylose isomerase. In some embodiments, the heterologously expressed polypeptide is a naturally occurring polypeptide. In some embodiments, the heterologously expressed polypeptide is recombinant. In some embodiments, the heterologously expressed polypeptide is a chimeric polypeptide. In some embodiments, the chimeric polypeptide is as described in the related provisional application U.S. 62/035,752 filed on Aug. 11, 2014, which application is hereby incorporated by reference in its entirety.

In some embodiments of the present invention, the heterologously expressed polypeptide has at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with any one of SEQ ID NOs: 1, 3, 5, 7, 9, 11, 13, 15, 17, 19, 21, 23, 25, and/or 27. In some embodiments, the heterologously expressed polypeptide has an amino acid sequence of SEQ ID NOs: 1, 3, 5, 7, 9, 11, 13, 15, 17, 19, 21, 23, 25, or 27. In some embodiments of the present invention, the heterologously expressed polypeptide has at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with any one of SEQ ID NOs: 1, 3, 5, 7, 9, 11, 13, 15, 17, 19, 21, 23, 25, 27, 35, 37, 39, and/or 41. In some embodiments, the heterologously expressed polypeptide has an amino acid sequence of SEQ ID NOs: 1, 3, 5, 7, 9, 11, 13, 15, 17, 19, 21, 23, 25, 27, 35, 37, 39, or 41.

In some embodiments, the heterologously expressed polypeptide is encoded by a polynucleotide sequence having at least 50%, at least 55%, at least 60%, at least 65%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with any one of SEQ ID NOs: 2, 4, 6, 8, 10, 12, 14, 16, 18, 20, 22, 24, 26, and/or 28. In some embodiments, the heterologously expressed polypeptide is encoded by a polynucleotide sequence of SEQ ID NOs: 2, 4, 6, 8, 10, 12, 14, 16, 18, 20, 22, 24, 26, or 28. In some embodiments, the heterologously expressed polypeptide is encoded by a polynucleotide sequence having at least 50%, at least 55%, at least 60%, at least 65%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with any one of SEQ ID NOs: 2, 4, 6, 8, 10, 12, 14, 16, 18, 20, 22, 24, 26, 28, 36, 38, 40, and/or 42. In some embodiments, the heterologously expressed polypeptide is encoded by a polynucleotide sequence of SEQ ID NOs: 2, 4, 6, 8, 10, 12, 14, 16, 18, 20, 22, 24, 26, 28, 36, 38, 40, or 42. In some embodiments, the polynucleotide sequence is contained in a vector.

In some embodiments, a host cell is engineered to express one or more of the chimeric polypeptides. In some embodiments, the host cell is a yeast cell, e.g. a S. cerevisiae cell. In some embodiments the host cell is further modified to have mutations affecting at least one gene encoding a protein involved in the pentose phosphate pathway. In some embodiments, the host cell has at least one mutation that increases the expression or causes the up-regulation of XKS1, RKI1, RPE1, TKL1, and/or TAL1. In some embodiments, the host cell has a modification of one or more aldose reductase genes. In some embodiments, the aldose reductase gene is GRE3. In some embodiments, the host cell has a deletion or disruption of all or part of the endogenous GRE3 gene. In some embodiments, the aldose reductase gene is YPR1. In some embodiments, the host cell has a deletion or disruption of all or part of the endogenous YPR1 gene. In some embodiments, the host cell has a deletion or disruption of all or part of both the endogenous GRE3 gene and the endogenous YPR1 gene. In some embodiments, the host cell has a modification of PGM1 (phosphoglucomutase 1) and/or PGM2. In some embodiments, the host cell overexpresses PGM1 and/or PGM2. In some embodiments, the host cell has increased levels of Pgm1 and/or Pgm2 polypeptide and/or mRNA relative to a comparable host cell lacking a modification of PGM1 and/or PGM2.

In some embodiments, the host cell comprises a deletion or disruption of one or more endogenous enzymes that function to produce glycerol and/or regulate glycerol synthesis. In some embodiments, the host cell produces less glycerol than a control recombinant microorganism without deletion or disruption of said one or more endogenous enzymes that function to produce glycerol and/or regulate glycerol synthesis. In some embodiments, the one or more endogenous enzymes that function to produce glycerol are encoded by a GPD1 polynucleotide, a GPD2 polynucleotide, or both a GPD1 polynucleotide and a GPD2 polynucleotide. In some embodiments, one or both of the endogenous GPD1 and/or GPD2 genes are modified by mutation or deletion. In some embodiments, the host cell comprises a heterologous ADHE sequence. In some embodiments, the heterologous ADHE is from *Bifidobacterium adolescentis*. In some embodiments the native STL1 gene is upregulated by either modifying the promoter of the native copies or by introducing additional copies of STL1. In some embodiments the host cell comprises an ortholog of the native STL1. In some embodiments the native ACS2 gene is upregulated by either modifying the promoter of the native copies or by introducing additional copies of ACS2. In some embodiments the host cell comprises an ortholog of the native ACS2 or ACS1 gene.

In some embodiments, the host cell comprises one or more mutations in one or more endogenous genes encoding a protein associated with iron metabolism. In some embodiments, the host cell comprises one or more mutations in one or more endogenous genes encoding an iron uptake protein, iron utilization protein, and/or an iron/sulfur (Fe/S) cluster biosynthesis protein. In some embodiments, the host cell comprises one or more mutations in one or more endogenous genes encoding a polypeptide affecting iron metabolism or Fe/S cluster biosynthesis. In some embodiments, the host cell is a recombinant yeast cell. In some embodiments, the recombinant yeast cell comprises one or more mutations in one or more of an endogenous gene selected from the group ISU1, YFH1, NFS1, AFT1, AFT2, YAP5, FRA1, FRA2, GREX3, GREX4, CCC1, and combinations thereof. In some embodiments, the recombinant yeast cell comprises one or more mutations in one or more of an endogenous gene which is homologous to one or more of an *S. cerevisiae* gene selected from the group ISU1, YFH1, NFS1, AFT1, AFT2, YAP5, FRA1, FRA2, GREX3, GREX4, and CCC1. In some embodiments, the recombinant yeast cell comprises a mutation in the endogenous AFT1 or AFT2 gene that results in iron-independent activation of the iron regulon such as the AFT1-1$^{up}$ or AFT2-1$^{up}$ alleles (Rutherford et al., "Aft1p and Aft2p mediate iron-responsive gene expression in yeast through related promoter elements," JBC 278(30): 27636-43 (2003)). In some embodiments, the recombinant yeast cell comprises a deletion or disruption of YAP5 and/or CCC1. In some embodiments, the recombinant yeast cell comprises a deletion or disruption of YAP5 and/or CCC1 and/or a mutation in the endogenous AFT1 or AFT2 gene that results in iron-independent activation of the iron regulon such as the AFT1-1$^{up}$ or AFT2-1$^{up}$ alleles.

In some embodiments, the host cell comprises one or more mutations in the endogenous ISU1 gene that results in a polypeptide comprising at least one amino acid substitution selected from the group consisting of D71N, D71G, and S98F, wherein the position of the substitution is relative to the amino acid positions of SEQ ID NO:29. In some embodiments, the host cell comprises one or more mutations in the endogenous YFH1 gene that results in a polypeptide comprising a T163P substitution, wherein the position of the substitution is relative to the amino acid positions of SEQ ID NO:31. In some embodiments, the host cell comprises one or more mutations in the endogenous NFS1 gene that results in a polypeptide comprising at least one amino acid substitution selected from the group consisting of L115W and E458D, wherein the position of the substitution is relative to the amino acid positions of SEQ ID NO:33.

In some embodiments, the host cell has a modification of PGM1 (phosphoglucomutase 1) and/or PGM2, as described in the related provisional application filed on Aug. 11, 2014, which application is incorporated by reference in its entirety. In some embodiments, the host cell overexpresses PGM1 and/or PGM2. In some embodiments, the host cell has increased levels of Pgm1 and/or Pgm2 polypeptide and/or mRNA relative to a comparable host cell lacking a modification of PGM1 and/or PGM2.

In some embodiments, the host cell expresses one or more heterologous genes encoding a protein that is associated with iron metabolism. In some embodiments, the heterologous gene confers on the recombinant yeast cell an increased ability to utilize xylose as compared to a similar yeast cell lacking the heterologous gene. In some embodiments, the heterologous gene is AFT1, AFT2, and/or an orthologue thereof. In some embodiments, the heterologous gene encodes a polypeptide having iron transport activity. In some embodiments, the heterologous gene encodes a protein that increases the activity and/or expression of Aft1 and/or Aft2. In some embodiments, the heterologous gene is a target of Aft1 and/or Aft2. In some embodiments, the heterologous gene is constitutively expressed. In some embodiments, the heterologous gene is overexpressed. In some embodiments, the heterologous gene encodes a protein that suppresses a gene or protein that suppresses Aft1 and/or Aft2 activity and/or expression. In some embodiments, the heterologous gene encodes a protein that suppresses a gene or protein that suppresses the activity and/or expression of one or more downstream targets of Aft1 and/or Aft2.

In some embodiments, a yeast strain is used as the host cell. In some embodiments, the background of the yeast strain is an industrial yeast strain. One having ordinary skill in the art would be aware of many potential known yeast strains that can be modified according to the present invention, and this invention contemplates all such potential background yeast strains.

In some embodiments of the invention, the recombinant host cell is used to produce a fermentation product from a cellulosic or lignocellulosic material. In some embodiments, the fermentation product is ethanol, lactic acid, 3-hydroxypropionic acid, hydrogen, butyric acid, acrylic acid, acetic acid, succinic acid, citric acid, malic acid, fumaric acid, an amino acid, 1,3-propane-diol, ethylene, glycerol, acetone, isopropyl alcohol, butanol, a β-lactam, an antibiotic, a cephalosporin, or a combination thereof. In some embodiments, the cellulosic or lignocellulosic material is insoluble cellulose, crystalline cellulose, pretreated hardwood, paper sludge, pretreated corn stover, pretreated sugar cane bagasse, pretreated corn cobs, pretreated switchgrass, pretreated municipal solid waste, pretreated distiller's dried grains, pretreated wheat straw, corn fiber, agave, or a combination thereof.

One aspect of the invention is directed to a composition comprising a lignocellulosic material and a recombinant yeast host cell comprising one or more mutations in one or more endogenous genes encoding a protein associated with iron metabolism and at least one gene encoding a polypeptide having xylose isomerase activity. Another aspect of the invention is directed to a media supernatant generated by incubating a recombinant yeast host comprising one or more mutations in one or more endogenous genes encoding a protein associated with iron metabolism and at least one gene encoding a polypeptide having xylose isomerase activity with a medium containing xylose as the only carbon source. In some embodiments, the medium comprises a cellulosic or lignocellulosic material. In some embodiments, the cellulosic or lignocellulosic material is insoluble cellulose, crystalline cellulose, pretreated hardwood, paper sludge, saw mill or paper mill discards, pretreated corn stover, pretreated sugar cane bagasse, pretreated corn cobs, pretreated switchgrass, pretreated municipal solid waste, pretreated distiller's dried grains, pretreated wheat straw, corn fiber, agave, or a combination thereof.

BRIEF DESCRIPTION OF THE DRAWINGS/FIGURES

FIG. 1 depicts a schematic representation of xylose fermentation in genetically engineered *S. cerevisiae*.

Figure 2:
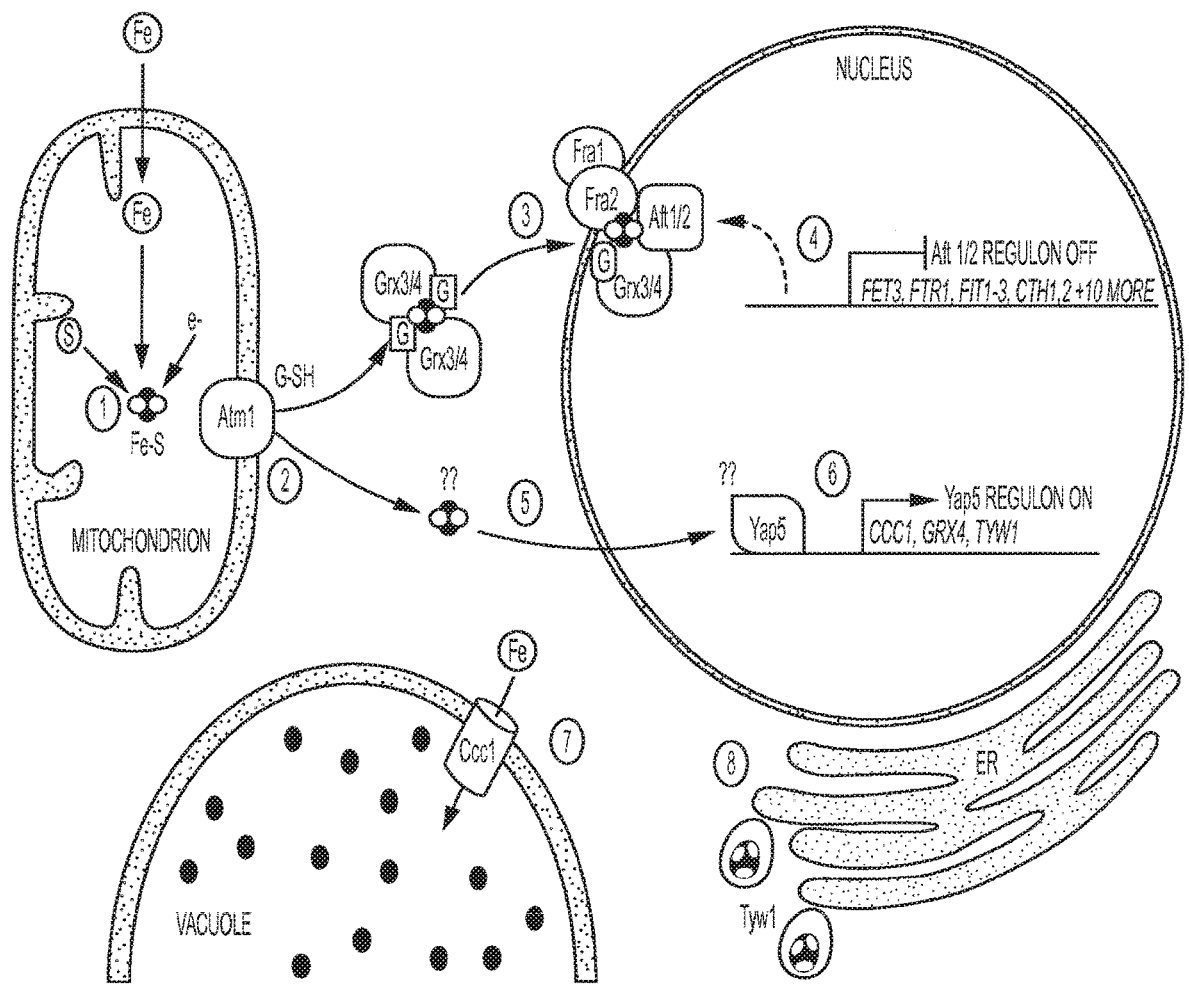

FIG. 2 depicts a schematic representation of the role of Fe/S clusters in intracellular iron metabolism. See Outten and Albetel, "Iron sensing and regulation in *Saccharomyces cerevisiae*: Ironing out the mechanistic details," *Curr. Op. Microbiol.* 16:662-68 (2013).

Figure 3A:
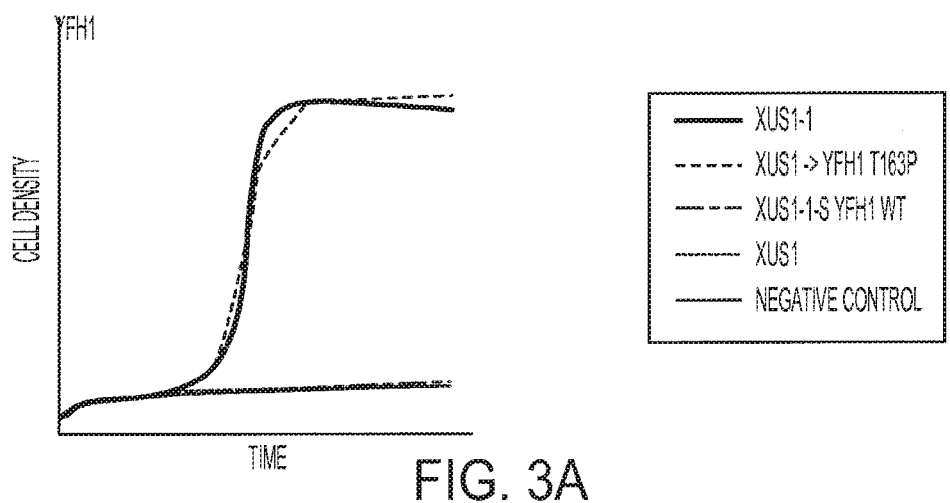
Figure 3B:
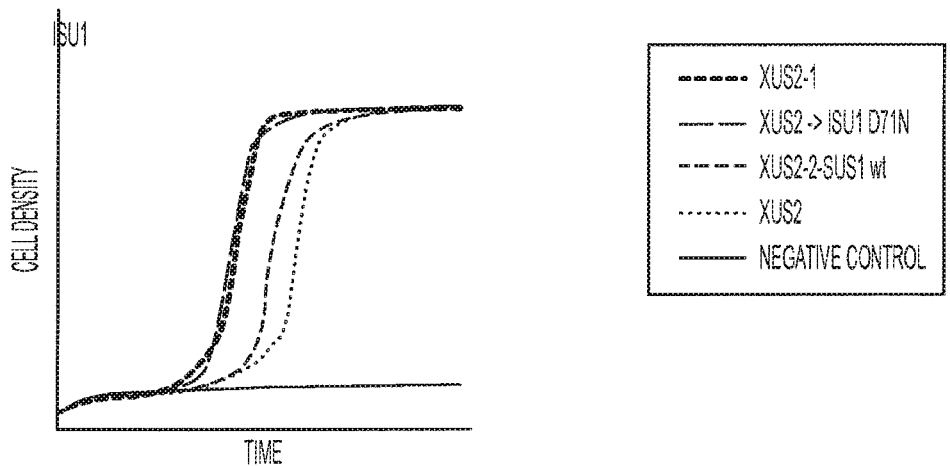
Figure 3C:
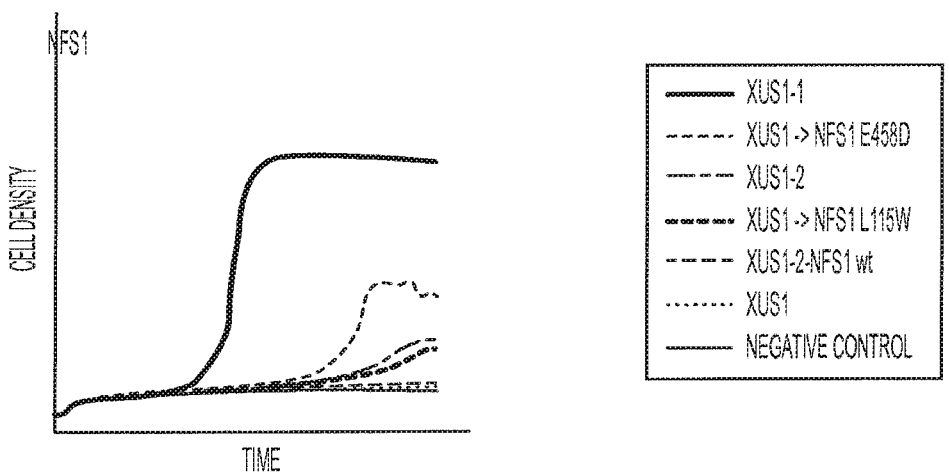

FIGS. 3A-3C provide examples of the relative growth of xylose utilizing yeast strains (XUS) with various mutations in genes encoding proteins associated with intracellular iron metabolism, specifically YFH1 (FIG. 3A), ISU1 (FIG. 3B), and NFS1 (FIG. 3C).

Figure 4A:
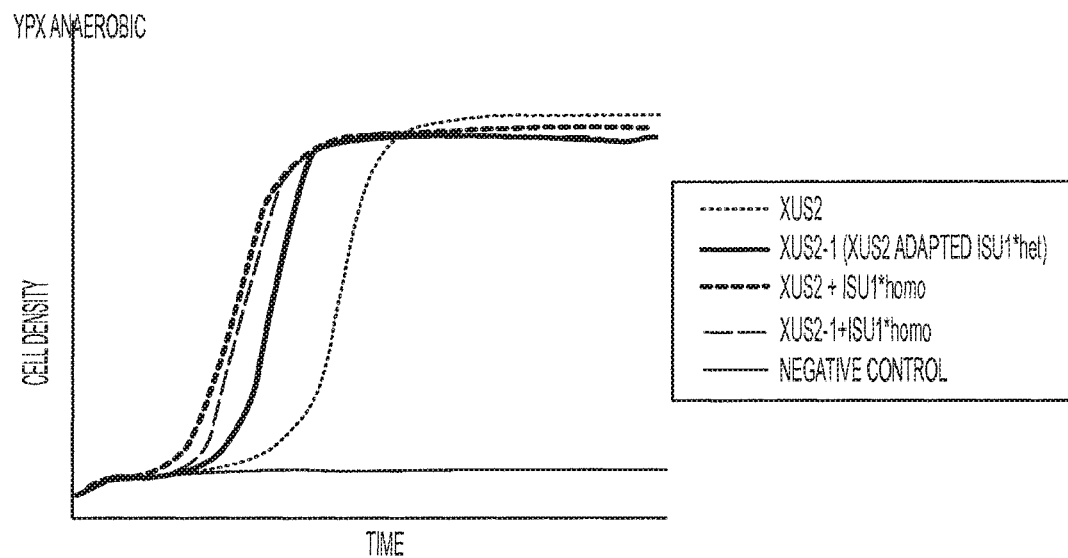
Figure 4B:
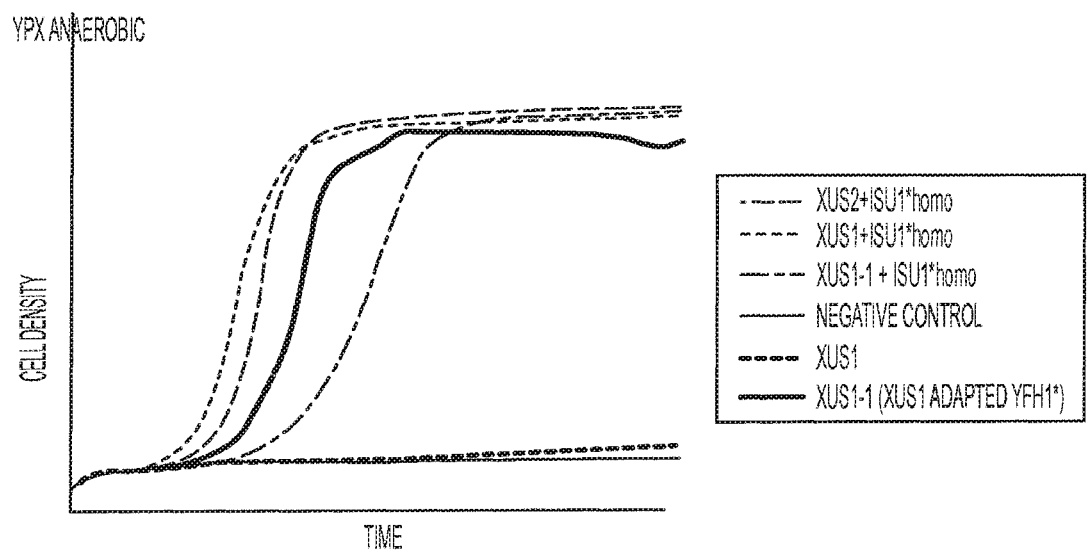

FIGS. 4A-4B provide examples of the relative growth of xylose utilizing yeast strains (XUS) with heterozygous and homozygous mutations in genes encoding proteins associated with intracellular iron metabolism, specifically ISU1 (FIG. 4A) and ISU1 and YFH1 (FIG. 4B), in two XUS strains.

FIG. 5 provides examples of the relative growth of xylose utilizing yeast strains heterologously expressing selected xylose isomerase genes, including those from *B. thetaiotaomicron* (BtXI), *Piromyces* (PiXI), *C. aberensis* (CaXI), *P. ruminicola* (PrXI), *P. distasonis* (PdXI), XYM2, *A. defectiva* (AdXI), *Lachnoanaerobaculum saburreum* (LsXI), *Clostridium phytofermentans* (CpXI), and *Lactobacillus xylosus* (LxXI). The growth levels for of each xylose utilizing yeast strain are show with (hashed bars) and without (solid bars) the T163P mutation of YFH1.

FIGS. 6A-6B provide examples of the relative growth of yeast cells heterologously expressing selected xylose isomerases (chromosomally integrated) including those from CX355=chimeric xylose isomerase 355, CX1224=chimeric xylose isomerase 1224, Ad=Abiotrophia defectiva, Bt=Bacteriodes thetaioatomicron, Pe=Piromyces, Ls=*Lachnoanaerobaculum saburreum* with and without a mutation in YFH1. The growth levels for of each xylose utilizing yeast strain are show with (FIG. 6A) and without (FIG. 6B) the T163P mutation of YFH1.

Figure 7:
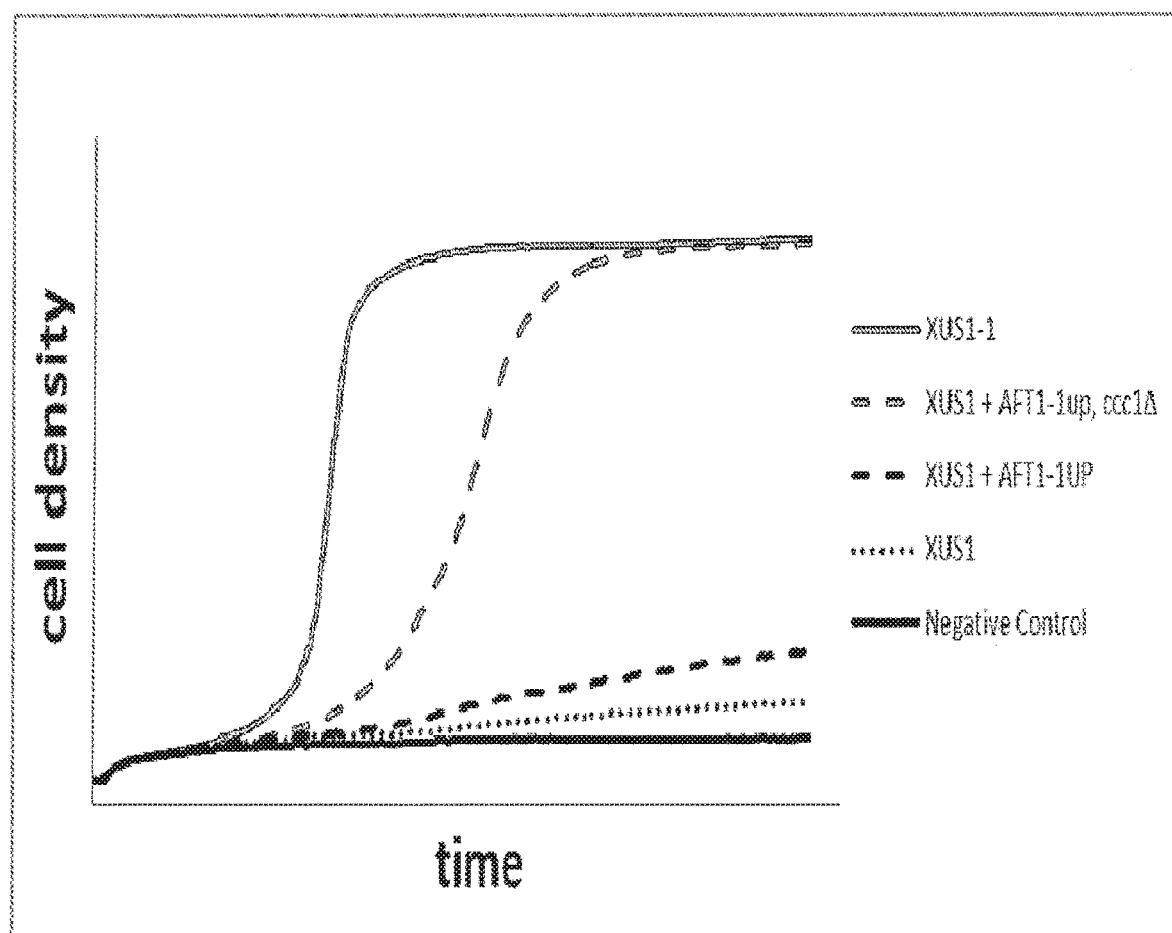

FIG. 7 provides examples of the relative growth of xylose utilizing yeast strains (XUS) with various mutations in genes encoding proteins associated with intracellular iron metabolism, specifically AFT1, and ccc1.

Figure 8:
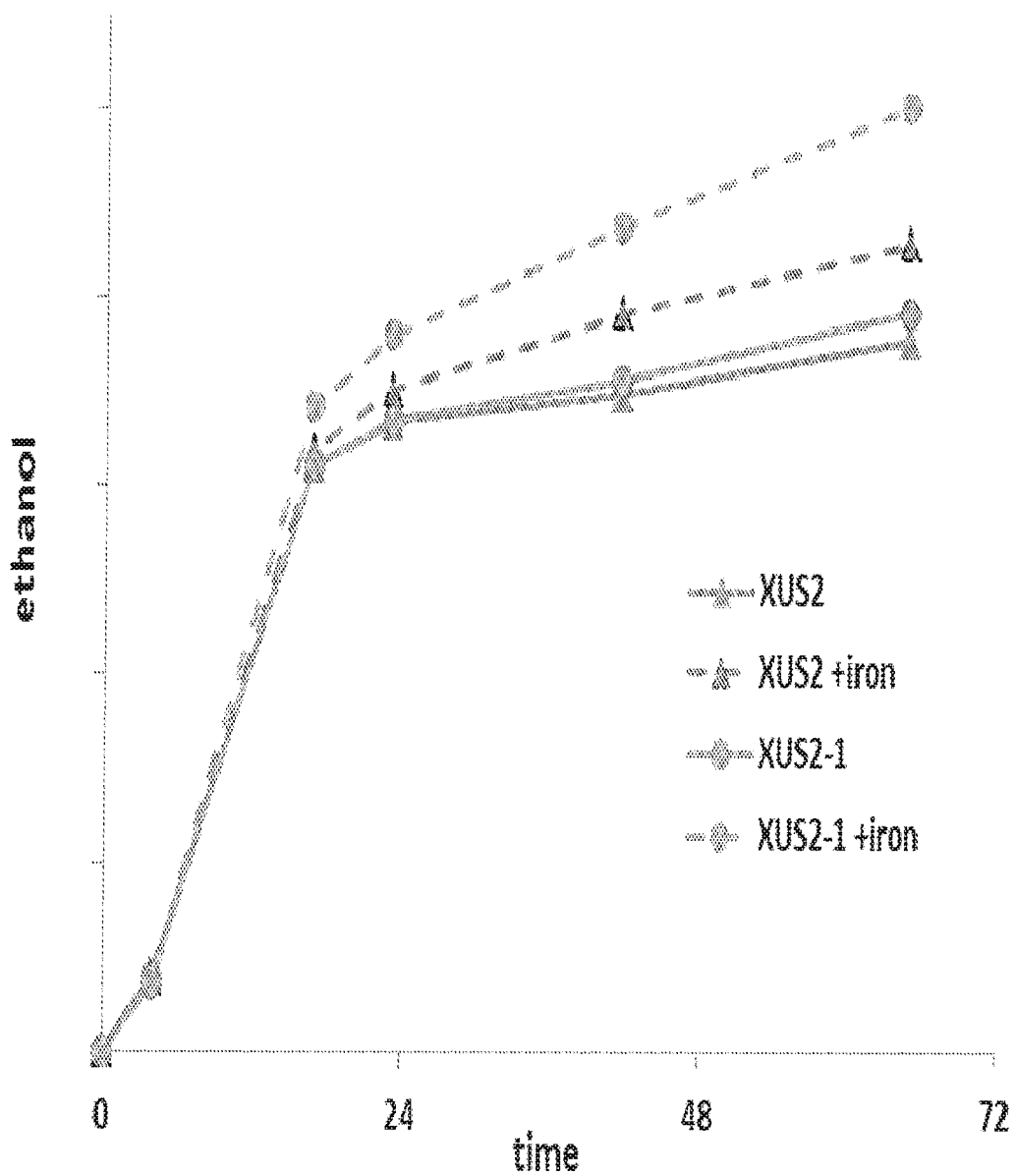
Figure 9:
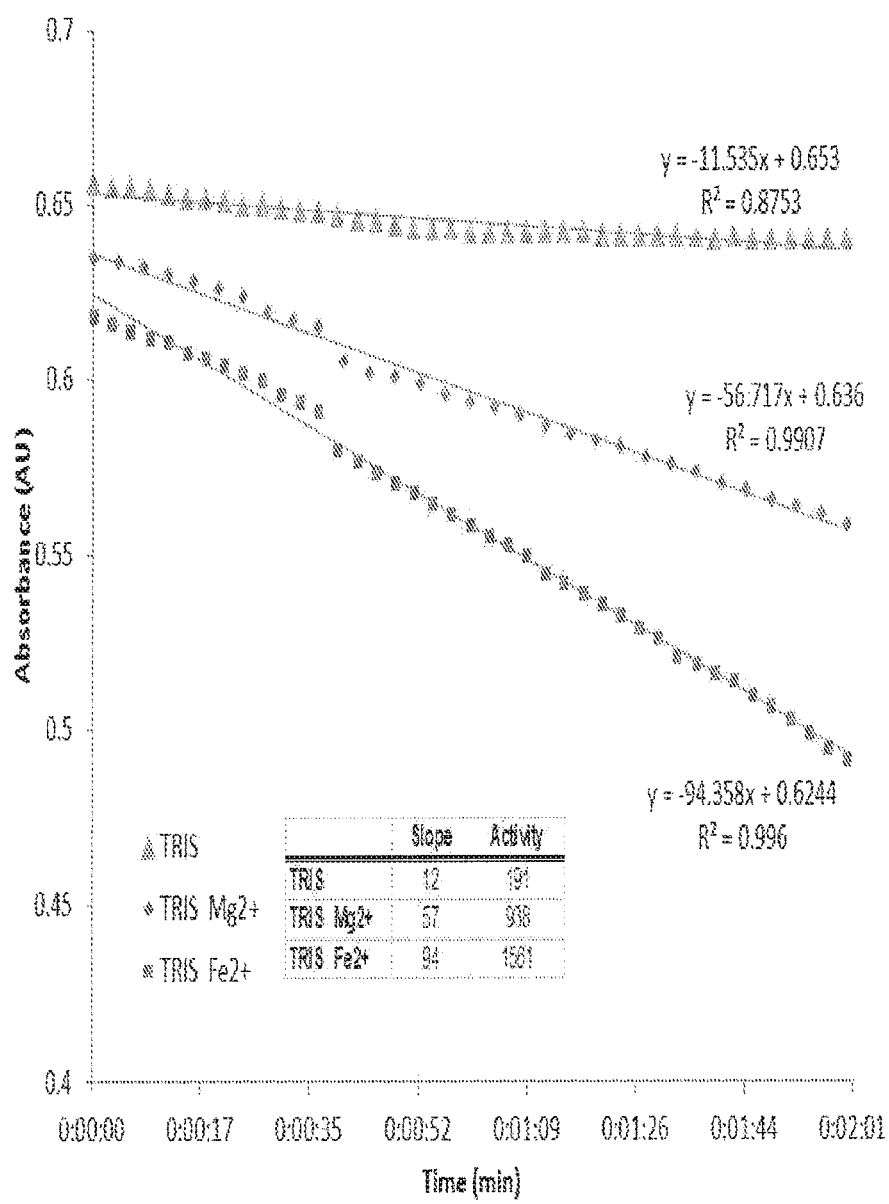

FIG. 8 provides examples of the relative ethanol production of xylose utilizing yeast strains (XUS) grown in glucose/xylose media with and without iron addition FIG. 9 provides examples of in vitro xylose isomerase activity assay of xylose utilizing yeast strains (XUS).

DETAILED DESCRIPTION OF THE INVENTION

I. Definitions

Unless defined otherwise, all technical and scientific terms used herein have the same meaning as commonly understood to one of ordinary skill in the art of microbial metabolic engineering. Although methods and materials similar or equivalent to those described herein can be used in the practice of the disclosed methods and compositions, exemplary methods, devices and materials are described herein.

The embodiment(s) described, and references in the specification to "one embodiment", "an embodiment", "an example embodiment", etc., indicate that the embodiment(s) described can include a particular feature, structure, or characteristic, but every embodiment does not necessarily include the particular feature, structure, or characteristic. Moreover, such phrases are not necessarily referring to the same embodiment. Further, when a particular feature, structure, or characteristic is described in connection with an embodiment, it is understood that it is within the knowledge of one skilled in the art to effect such feature, structure, or characteristic in connection with other embodiments whether or not explicitly described.

The description of "a" or "an" item herein refers to a single item or multiple items. It is understood that wherever embodiments are described herein with the language "comprising," otherwise analogous embodiments described in terms of "consisting of" and/or "consisting essentially of" are also provided. Thus, for example, reference to "a polynucleotide" includes a plurality of such polynucleotides and reference to "the microorganism" includes reference to one or more microorganisms, and so forth.

A "fragment" refers to any portion of a nucleic or amino acid sequence that is less than the entire sequence. A fragment of a nucleotide or an amino acid sequence can be any length of nucleotides or amino acids that is less than the entire length of the cited sequence and more than two nucleotides or amino acids in length. In some embodiments, the fragment can be from a donor sequence.

A "vector," e.g., a "plasmid" or "YAC" (yeast artificial chromosome) refers to an extrachromosomal element often carrying one or more genes that are not part of the central metabolism of the cell, and can be in the form of a linear or circular double-stranded DNA molecule. Vectors and plasmids can be autonomously replicating sequences, genome integrating sequences, phage or nucleotide sequences, linear, circular, or supercoiled, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

An "expression vector" is a vector that is capable of directing the expression of genes to which it is operably associated.

The term "integrated" as used herein refers to genetic elements that are placed, through molecular biology techniques, into the genome of a host cell. For example, genetic elements can be placed into the chromosomes of the host cell as opposed to in a plasmid carried by the host cell. Methods for integrating genetic elements into the genome of a host cell are well known in the art and include homologous recombination. In some embodiments, more than one copy of the genetic elements are placed into the genome of a host cell. In some embodiments, 2, 3, 4, 5, 6, 7, 8, 9, 10, or more copies of the genetic elements are placed into the genome of a host cell.

The term "heterologous" when used in reference to a polynucleotide, a gene, a polypeptide, or an enzyme refers to a polynucleotide, gene, polypeptide, or an enzyme not normally found in the host organism. "Heterologous" also includes a native coding region, or portion thereof, that is removed from the source organism and subsequently reintroduced into the source organism in a form that is different from the corresponding native gene, e.g., not in its natural location in the organism's genome. The heterologous polynucleotide or gene can be introduced into the host organism by, e.g., gene transfer. A heterologous gene can include a native coding region that is a portion of a chimeric gene including non-native regulatory regions that is reintroduced into the native host. Foreign genes can comprise native genes inserted into a non-native organism, or chimeric genes. A heterologous polynucleotide, gene, polypeptide, or an enzyme can be derived from any source, e.g., eukaryotes, prokaryotes, viruses, or synthetic polynucleotide fragments. The term "heterologous" as used herein also refers to an element of a vector, plasmid or host cell that is derived from a source other than the endogenous source. Thus, for example, a heterologous sequence could be a sequence that is derived from a different gene or plasmid from the same host, from a different strain of host cell, or from an organism of a different taxonomic group (e.g., different kingdom, phylum, class, order, family, genus, or species, or any subgroup within one of these classifications). The term "heterologous" is also used synonymously herein with the term "exogenous." The term "heterologous expression" refers to the expression of a heterologous polynucleotide or gene by a host.

The term "domain" as used herein refers to a part of a molecule or structure that shares common physical or chemical features, for example hydrophobic, polar, globular, helical domains or properties, e.g., a DNA binding domain or an ATP binding domain. Domains can be identified by their homology to conserved structural or functional motifs. Examples of cellobiohydrolase (CBH) domains include the catalytic domain (CD) and the cellulose binding domain (CBD).

A "nucleic acid," "polynucleotide," or "nucleic acid molecule" is a polymeric compound comprised of covalently linked subunits called nucleotides. Nucleic acid includes polyribonucleic acid (RNA) and polydeoxyribonucleic acid (DNA), both of which can be single-stranded or double-stranded. DNA includes cDNA, genomic DNA, synthetic DNA, and semi-synthetic DNA.

An "isolated nucleic acid molecule" or "isolated nucleic acid fragment" refers to the phosphate ester polymeric form of ribonucleosides (adenosine, guanosine, uridine, or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences are described herein according to the normal convention of giving only the sequence in the 5' to 3' direction along the non-transcribed strand of DNA (i.e., the strand having a sequence homologous to the mRNA).

A "gene" refers to an assembly of nucleotides that encode a polypeptide, and includes cDNA and genomic DNA nucleic acids. "Gene" also refers to a nucleic acid fragment that expresses a specific protein, including intervening sequences (introns) between individual coding segments (exons), as well as regulatory sequences preceding (5' non-coding sequences) and following (3' non-coding sequences) the coding sequence. "Native gene" refers to a gene as found in nature with its own regulatory sequences. The terms "gene(s)" or "polynucleotide" or "nucleic acid" or "polynucleotide sequence(s)" are intended to include nucleic acid molecules, e.g., polynucleotides which include an open reading frame encoding a polypeptide, and can further include non-coding regulatory sequences, and introns. In addition, the terms are intended to include one or more genes that map to a functional locus. Also, the terms are intended to include a specific gene for a selected purpose. The gene can be endogenous to the host cell or can be recombinantly introduced into the host cell, e.g., as a plasmid maintained episomally or a plasmid (or fragment thereof) that is stably integrated into the genome. In addition to the plasmid form, a gene can, for example, be in the form of linear DNA or RNA. The term "gene" is also intended to refer to multiple copies of a particular gene, e.g., all of the DNA sequences in a cell encoding a particular gene product.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength. Hybridization and washing conditions are well known and exemplified, e.g., in Sambrook, J., Fritsch, E. F. and Maniatis, T. MOLECULAR CLONING: A LABORATORY MANUAL, Second Edition, Cold Spring Harbor Laboratory Press, Cold Spring Harbor (1989), particularly Chapter 11 and Table 11.1 therein (hereinafter "Maniatis", entirely incorporated herein by reference). The conditions of temperature and ionic strength determine the "stringency" of the hybridization. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. For more stringent conditions, washes are performed at higher temperatures in which the washes are identical to those above except for the temperature of the final two 30 min washes in 0.2×SSC, 0.5% SDS are increased to 60° C. Another set of highly stringent conditions uses two final washes in 0.1×SSC, 0.1% SDS at 65° C. An additional set of highly stringent conditions are defined by hybridization at 0.1×SSC, 0.1% SDS, 65° C. and washed with 2×SSC, 0.1% SDS followed by 0.1×SSC, 0.1% SDS.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see, e.g., Maniatis at 9.50-9.51). For hybridizations with shorter nucleic acids, i.e., oligonucleotides, the position of mismatches becomes more important, and the length of the oligonucleotide determines its specificity (see, e.g., Maniatis, at 11.7-11.8). In one embodiment the length for a hybridizable nucleic acid is at least about 10 nucleotides. Preferably a minimum length for a hybridizable nucleic acid is at least about 15 nucleotides; more preferably at least about 20 nucleotides; and most preferably the length is at least 30 nucleotides. Furthermore, the skilled artisan will recognize that the temperature and wash solution salt concentration can be adjusted as necessary according to factors such as length of the probe.

As used herein the term "codon-optimized" means that a nucleic acid coding region has been adapted for expression in the cells of a given organism by replacing one, or more than one, or a significant number, of codons with one or more codons that are more frequently used in the genes of that organism.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case can be, as determined by the match between strings of such sequences.

As known in the art, "similarity" between two polypeptides is determined by comparing the amino acid sequence and conserved amino acid substitutes thereto of the polypeptide to the sequence of a second polypeptide. Similarity can be between two full sequences, or between a fragment of one sequence and a fragment of a second sequence wherein the fragments are of comparable length or size, or between a fragment of one sequence and the entirety of a second sequence.

"Identity" and "similarity" can be readily calculated by known methods, including but not limited to those described in: Computational Molecular Biology (Lesk, A. M, ed.) Oxford University Press, N.Y. (1988); Biocomputing: Informatics and Genome Projects (Smith, D. W., ed.) Academic Press, N.Y. (1993); Computer Analysis of Sequence Data, Part I (Griffin, A. M., and Griffin, H. G., eds.) Humana Press, NJ (1994); Sequence Analysis in Molecular Biology (von Heinje, G., ed.) Academic Press (1987); and Sequence Analysis Primer (Gribskov, M. and Devereux, J., eds.) Stockton Press, N.Y. (1991). Preferred methods to determine identity are designed to give the best match between the sequences tested. Methods to determine identity and similarity are codified in publicly available computer programs. Sequence alignments and percent identity calculations can be performed using the Megalign program of the LASERGENE bioinformatics computing suite (DNASTAR Inc., Madison, Wis.). Multiple alignments of the sequences disclosed herein were performed using the Clustal method of alignment (Higgins and Sharp (1989) CABIOS. 5:151-153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

Suitable nucleic acid sequences or fragments thereof (isolated polynucleotides of the present invention) encode polypeptides that are at least about 70% to about 75% identical to the amino acid sequences reported herein, at least about 80%, at least about 85%, at least about 86%, at least about 87%, at least about 88%, at least about 89%, or at least about 90% identical to the amino acid sequences reported herein, at least about 91%, at least about 92%, at least about 93%, at least about 94%, or at least about 95% identical to the amino acid sequences reported herein, or at least about 96%, at least about 97%, at least about 98%, at least about 99%, or about 100% identical to the amino acid sequences reported herein. Suitable nucleic acid fragments are at least about 50%, at least about 55%, at least about 60%, at least about 65%, at least about 70%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or about 100% identical to the nucleic acid sequences reported herein. Suitable nucleic acid fragments not only have the above identities/similarities but typically encode a polypeptide having at least 50 amino acids, at least 100 amino acids, at least 150 amino acids, at least 200 amino acids, or at least 250 amino acids.

A DNA or RNA "coding region" is a DNA or RNA molecule which is transcribed and/or translated into a polypeptide in a cell in vitro or in vivo when placed under the control of appropriate regulatory sequences. "Suitable regulatory regions" refer to nucleic acid regions located upstream (5' non-coding sequences), within, or downstream (3' non-coding sequences) of a coding region, and which influence the transcription, RNA processing or stability, or translation of the associated coding region. Regulatory regions include promoters, translation leader sequences, RNA processing site, effector binding site and stem-loop structure. The boundaries of the coding region are determined by a start codon at the 5' (amino) terminus and a translation stop codon at the 3' (carboxyl) terminus. A coding region can include, but is not limited to, prokaryotic regions, cDNA from mRNA, genomic DNA molecules, synthetic DNA molecules, or RNA molecules. If the coding region is intended for expression in a eukaryotic cell, a polyadenylation signal and transcription termination sequence will usually be located 3' to the coding region.

An "isoform" is a protein that has the same function as another protein but which is encoded by a different gene and can have small differences in its sequence.

A "paralogue" is a protein encoded by a gene related by duplication within a genome.

An "orthologue" is gene from a different species that has evolved from a common ancestral gene by speciation. Normally, orthologues retain the same function in the course of evolution as the ancestral gene.

"Open reading frame" is abbreviated ORF and means a length of nucleic acid, either DNA, cDNA or RNA, that comprises a translation start signal or initiation codon, such as an ATG or AUG, and a termination codon and can be potentially translated into a polypeptide sequence.

"Promoter" refers to a DNA fragment capable of controlling the expression of a coding sequence or functional RNA. In general, a coding region is located 3' to a promoter. Promoters can be isolated in their entirety from a native gene, or be composed of different elements derived from different promoters found in nature, or even comprise synthetic DNA segments. It is understood by those skilled in the art that different promoters can direct the expression of a gene in different tissues or cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths can have identical promoter activity. A promoter is generally bounded at its 3' terminus by the transcription initiation site and extends upstream (5' direction) to include the minimum number of bases or elements necessary to initiate transcription at levels detectable above background. Within the promoter will be found a transcription initiation site (conveniently defined for example, by mapping with nuclease SI), as well as protein binding domains (consensus sequences) responsible for the binding of RNA polymerase. Several promoters are specifically identified by the present invention, however, one having ordinary skill in the art would understand that any number of additional promoters capable of driving the expression in yeast would be included in the present invention.

The term "linker" as used herein refers to a series of nucleotides or amino acids that connect one section of the chimeric polynucleotide or polypeptide to another section of the chimeric polynucleotide of polypeptide. In some embodiments, the linker serves a structural function.

A coding region is "under the control" of transcriptional and translational control elements in a cell when RNA polymerase transcribes the coding region into mRNA, which is then trans-RNA spliced (if the coding region contains introns) and translated into the protein encoded by the coding region.

"Transcriptional and translational control regions" are DNA regulatory regions, such as promoters, enhancers, terminators, and the like, that provide for the expression of a coding region in a host cell. In eukaryotic cells, polyadenylation signals are control regions.

As used herein the term "N-terminal region" refers to the portion of the amino acid sequence consisting of the most N-terminal amino acid residue up to the amino acid residue at position n/2, wherein n is the total number of residues in the sequence. As used herein the term "C-terminal region" refers to the portion of the amino acid sequence consisting of the most C-terminal amino acid residue up to the amino acid residue at position n/2, wherein n is the total number of residues in the sequence.

The term "operably associated" refers to the association of nucleic acid sequences on a single nucleic acid fragment so that the function of one is affected by the other. For example, a promoter is operably associated with a coding region when it is capable of affecting the expression of that coding region (i.e., that the coding region is under the transcriptional control of the promoter). Coding regions can be operably associated to regulatory regions in sense or antisense orientation.

The term "expression," as used herein, refers to the transcription and stable accumulation of sense (mRNA) or antisense RNA derived from the nucleic acid fragment of the invention. Expression can also refer to translation of mRNA into a polypeptide.

The term "lignocellulose" refers to material that is comprised of lignin and cellulose. Examples of lignocelluloses are provided herein and are known in the art. Examples of lignocellulosic materials include but are not limited to corn stover, straw, bagasse, switchgrass, paper, and wood.

The "pentose phosphate pathway" or "PPP" refers to a biochemical pathway that creates NADPH from glucose-6-P. The PPP has both an oxidative phase and a non-oxidative phase. There are several enzymes that have been identified to play a role in the PPP, including but not limited to glucose-6-P dehydrogenase, gluconolactonase, 6-phosphogluconate dehydrogenase, ribulose-5-phosphate isomerase, ribose-5-phosphate ketol-isomerase (RKI1), ribulose-5-phosphate 3-epimerase (RPE1), transketolase (TKL1), and transaldolase (TAL1).

As used herein "xylose isomerase activity" refers to the ability of an enzyme to directly convert xylose to xylulose. A "xylose isomerase" or "XI" as used herein refers to a protein having xylose isomerase activity (EC 5.3.1.5).

The term "chimeric" or "chimera" refers to a polynucleotide or polypeptide having a nucleotide or polypeptide sequence derived from two or more distinct parent sequences. A "parent sequence" or "donor sequence" is a nucleotide or amino acid sequence used as a source sequence to create the chimeric polynucleotide or polypeptide.

As used herein the term "XYM1" or "XYM2" refers to a xylose isomerase coding sequence or polypeptide isolated from an uncultured bacterium as described by Parachin and Gorwa-Grauslund, "Isolation of xylose isomerase by sequence- and function-based screening from a soil metagenome library," *Biotechnology Biofuels* 4(1:)9 (2011).

As used herein, the term "anaerobic" refers to an organism, biochemical reaction, or process that is active or occurs under conditions of an absence of gaseous $O_2$.

"Anaerobic conditions" are defined as conditions under which the oxygen concentration in the fermentation medium is too low for the microorganism to use it as a terminal electron acceptor. Anaerobic conditions can be achieved by sparging a fermentation medium with an inert gas such as nitrogen until oxygen is no longer available to the microorganism as a terminal electron acceptor. Alternatively, anaerobic conditions can be achieved by the microorganism consuming the available oxygen of fermentation until oxygen is unavailable to the microorganism as a terminal electron acceptor.

"Aerobic metabolism" refers to a biochemical process in which oxygen is used as a terminal electron acceptor to convert energy, typically in the form of ATP, from carbohydrates. Aerobic metabolism typically occurs, for example, via the electron transport chain in mitochondria in eukaryotes, wherein a single glucose molecule is metabolized completely into carbon dioxide in the presence of oxygen.

In contrast, "anaerobic metabolism" refers to a biochemical process in which oxygen is not the final acceptor of electrons generated. Anaerobic metabolism can be divided into anaerobic respiration, in which compounds other than oxygen serve as the terminal electron acceptor, and substrate level phosphorylation, in which no exogenous electron acceptor is used and products of an intermediate oxidation state are generated via a "fermentative pathway."

In "fermentative pathways", the amount of NAD(P)H generated by glycolysis is balanced by the consumption of the same amount of NAD(P)H in subsequent steps. For example, in one of the fermentative pathways of certain yeast strains, NAD(P)H generated through glycolysis donates its electrons to acetaldehyde, yielding ethanol. Fermentative pathways are usually active under anaerobic conditions but can also occur under aerobic conditions, under conditions where NADH is not fully oxidized via the respiratory chain.

As used herein, the term "end-product" refers to a chemical compound that is not or cannot be used by a cell, and so is excreted or allowed to diffuse into the extracellular environment. Common examples of end-products from anaerobic fermentation include, but are not limited to, ethanol, acetic acid, formic acid, lactic acid, hydrogen, and carbon dioxide.

As used herein, "cofactors" are compounds involved in biochemical reactions that are recycled within the cells and remain at approximately steady state levels. Common examples of cofactors involved in anaerobic fermentation include, but are not limited to, $NAD^+$ and $NADP^+$. In metabolism, a cofactor can act in oxidation-reduction reactions to accept or donate electrons. When organic compounds are broken down by oxidation in metabolism, their energy can be transferred to $NAD^+$ by its reduction to NADH, to $NADP^+$ by its reduction to NADPH, or to another cofactor, $FAD^+$, by its reduction to $FADH_2$. The reduced cofactors can then be used as a substrate for a reductase.

As used herein, a "pathway" is a group of biochemical reactions that together can convert one compound into another compound in a step-wise process. A product of the first step in a pathway can be a substrate for the second step, and a product of the second step can be a substrate for the third, and so on. Pathways of the present invention include, but are not limited to, the pentose phosphate pathway, the xylose utilization pathway, the ethanol production pathway, and the glycerol production pathway. The term "recombination" or "recombinant" refers to the physical exchange of DNA between two identical (homologous), or nearly identical, DNA molecules. Recombination can be used for targeted gene deletion or to modify the sequence of a gene. The terms "recombinant microorganism" and "recombinant host cell" are used interchangeably herein and refer to microorganisms that have been genetically modified to express or over-express endogenous polynucleotides, or to express heterologous polynucleotides, such as those included in a vector, or which have a modification in expression of an endogenous gene.

By "expression modification" it is meant that the expression of the gene, or level of a RNA molecule or equivalent RNA molecules encoding one or more polypeptides or polypeptide subunits, or activity of one or more polypeptides or polypeptide subunits is up regulated or down-regulated, such that expression, level, or activity, is greater than or less than that observed in the absence of the modification.

The term "iron metabolism" refers to the process by which a cell regulates the intracellular level of iron. The term "protein associated with iron metabolism" refers to a protein involved in the regulation of intracellular iron, including, e.g., a protein that imports, exports, binds, and/or sequesters iron or a protein that controls the expression of a gene that encodes for a protein that imports, exports, binds, and/or sequesters iron. The term "Fe/S cluster biosynthesis" refers to the biosynthesis of Fe/S clusters, including, e.g., the assembly and loading of Fe/S clusters. The term "Fe/S cluster biosynthesis genes", "Fe/S cluster biosynthesis proteins" or "Fe/S cluster biosynthesis pathway" refers to those polynucleotides and/or genes that are involved in the biosynthesis of Fe/S clusters, including, e.g., the assembly and loading of Fe/S clusters.

In one aspect of the invention, genes or particular polynucleotide sequences are partially, substantially, or completely deleted, silenced, inactivated, or down-regulated in order to inactivate the enzymatic activity they encode. Complete deletions provide maximum stability because there is no opportunity for a reverse mutation to restore function. Alternatively, genes can be partially, substantially, or completely deleted, silenced, inactivated, or down-regulated by insertion, deletion, removal, or substitution of nucleic acid sequences that disrupt the function and/or expression of the gene.

II. Xylose Isomerase Polypeptides

The present invention provides host cells comprising (a) one or more mutations in one or more endogenous genes encoding a protein associated with iron metabolism and (b) at least one gene encoding a polypeptide having xylose isomerase activity the use thereof. In some embodiments, the host cell heterologously expresses the polypeptide. In some embodiments, the heterologously expressed polypeptide is a naturally occurring polypeptide. In some embodiments, the heterologously expressed polypeptide is recombinant. In some embodiments, the heterologously expressed polypeptide is a chimeric polypeptide.

In some embodiments, the polypeptide has an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with any one of SEQ ID NOs: 1, 3, 5, 7, 9, 11, 13, 15, 17, 19, 21, 23, 25, and/or 27. In some embodiments, the polypeptide has an amino acid sequence of SEQ ID NOs: 1, 3, 5, 7, 9, 11, 13, 15, 17, 19, 21, 23, 25, or 27. In some embodiments, the polypeptide is encoded by a polynucleotide sequence having at least 50%, at least 55%, at least 60%, at least 65%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with any one of SEQ ID NOs: 2, 4, 6, 8, 10, 12, 14, 16, 18, 20, 22, 24, 26, and/or 28.

In some embodiments, the polypeptide is encoded by a polynucleotide sequence of SEQ ID NOs: 2, 4, 6, 8, 10, 12, 14, 16, 18, 20, 22, 24, 26, or 28. In some embodiments, the polypeptide has an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with any one of SEQ ID NOs: 1, 3, 5, 7, 9, 11, 13, 15, 17, 19, 21, 23, 25, 27, 35, 37, 39, and/or 41. In some embodiments, the polypeptide has an amino acid sequence of SEQ ID NOs: 1, 3, 5, 7, 9, 11, 13, 15, 17, 19, 21, 23, 25, 27, 35, 37, 39, or 41. In some embodiments, the polypeptide is encoded by a polynucleotide sequence having at least 50%, at least 55%, at least 60%, at least 65%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with any one of SEQ ID NOs: 2, 4, 6, 8, 10, 12, 14, 16, 18, 20, 22, 24, 26, 28, 36, 38, 40, and/or 42. In some embodiments, the polypeptide is encoded by a polynucleotide sequence of SEQ ID NOs: 2, 4, 6, 8, 10, 12, 14, 16, 18, 20, 22, 24, 26, 28, 36, 38, 40, or 42.

In some embodiments, the polypeptide has an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with the amino acid sequence of SEQ ID NO: 1. In some embodiments, the polypeptide has an amino acid sequence having 100% sequence identity with the amino acid sequence of SEQ ID NO: 1.

In some embodiments, the polypeptide has an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with the amino acid sequence of SEQ ID NO: 3. In some embodiments, the polypeptide has an amino acid sequence having 100% sequence identity with the amino acid sequence of SEQ ID NO: 3.

In some embodiments, the polypeptide has an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with the amino acid sequence of SEQ ID NO: 5. In some embodiments, the polypeptide has an amino acid sequence having 100% sequence identity with the amino acid sequence of SEQ ID NO: 5.

In some embodiments, the polypeptide has an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with the amino acid sequence of SEQ ID NO: 7. In some embodiments, the polypeptide has an amino acid sequence having 100% sequence identity with the amino acid sequence of SEQ ID NO: 7.

In some embodiments, the polypeptide has an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with the amino acid sequence of SEQ ID NO: 9. In some embodiments, the polypeptide has an amino acid sequence having 100% sequence identity with the amino acid sequence of SEQ ID NO: 9.

In some embodiments, the polypeptide has an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with the amino acid sequence of SEQ ID NO: 11. In some embodiments, the polypeptide has an amino acid sequence having 100% sequence identity with the amino acid sequence of SEQ ID NO: 11.

In some embodiments, the polypeptide has an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with the amino acid sequence of SEQ ID NO: 13. In some embodiments, the polypeptide has an amino acid sequence having 100% sequence identity with the amino acid sequence of SEQ ID NO: 13.

In some embodiments, the polypeptide has an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with the amino acid sequence of SEQ ID NO: 15. In some embodiments, the polypeptide has an amino acid sequence having 100% sequence identity with the amino acid sequence of SEQ ID NO: 15.

In some embodiments, the polypeptide has an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with the amino acid sequence of SEQ ID NO: 17. In some embodiments, the polypeptide has an amino acid sequence having 100% sequence identity with the amino acid sequence of SEQ ID NO: 17.

In some embodiments, the polypeptide has an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with the amino acid sequence of SEQ ID NO: 19. In some embodiments, the polypeptide has an amino acid sequence having 100% sequence identity with the amino acid sequence of SEQ ID NO: 19.

In some embodiments, the polypeptide has an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with the amino acid sequence of SEQ ID NO: 21. In some embodiments, the polypeptide has an amino acid sequence having 100% sequence identity with the amino acid sequence of SEQ ID NO: 21.

In some embodiments, the polypeptide has an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with the amino acid sequence of SEQ ID NO: 23. In some embodiments, the polypeptide has an amino acid sequence having 100% sequence identity with the amino acid sequence of SEQ ID NO: 23.

In some embodiments, the polypeptide has an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with the amino acid sequence of SEQ ID NO: 25. In some embodiments, the polypeptide has an amino acid sequence having 100% sequence identity with the amino acid sequence of SEQ ID NO: 25.

In some embodiments, the polypeptide has an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with the amino acid sequence of SEQ ID NO: 27. In some embodiments, the polypeptide has an amino acid sequence having 100% sequence identity with the amino acid sequence of SEQ ID NO: 27.

In some embodiments, the polypeptide has an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with the amino acid sequence of SEQ ID NO: 35. In some embodiments, the polypeptide has an amino acid sequence having 100% sequence identity with the amino acid sequence of SEQ ID NO: 35.

In some embodiments, the polypeptide has an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with the amino acid sequence of SEQ ID NO: 37. In some embodiments, the polypeptide has an amino acid sequence having 100% sequence identity with the amino acid sequence of SEQ ID NO: 37.

In some embodiments, the polypeptide has an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with the amino acid sequence of SEQ ID NO: 39. In some embodiments, the polypeptide has an amino acid sequence having 100% sequence identity with the amino acid sequence of SEQ ID NO: 39.

In some embodiments, the polypeptide has an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with the amino acid sequence of SEQ ID NO: 41. In some embodiments, the polypeptide has an amino acid sequence having 100% sequence identity with the amino acid sequence of SEQ ID NO: 41.

In some embodiments, the polypeptide is encoded by a polynucleotide sequence having at least 50%, at least 55%, at least 60%, at least 65%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with the nucleotide sequence of SEQ ID NO: 2. In some embodiments, the polypeptide is encoded by a polynucleotide sequence of SEQ ID NO: 2.

In some embodiments, the polypeptide is encoded by a polynucleotide sequence having at least 50%, at least 55%, at least 60%, at least 65%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with the nucleotide sequence of SEQ ID NO: 4.

In some embodiments, the polypeptide is encoded by a polynucleotide sequence having at least 50%, at least 55%, at least 60%, at least 65%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with the nucleotide sequence of SEQ ID NO: 6. In some embodiments, the polypeptide is encoded by a polynucleotide sequence of SEQ ID NO: 6.

In some embodiments, the polypeptide is encoded by a polynucleotide sequence having at least 50%, at least 55%, at least 60%, at least 65%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with the nucleotide sequence of SEQ ID NO: 8. In some embodiments, the polypeptide is encoded by a polynucleotide sequence of SEQ ID NO: 8.

In some embodiments, the polypeptide is encoded by a polynucleotide sequence having at least 50%, at least 55%, at least 60%, at least 65%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with the nucleotide sequence of SEQ ID NO: 10. In some embodiments, the polypeptide is encoded by a polynucleotide sequence of SEQ ID NO: 10.

In some embodiments, the polypeptide is encoded by a polynucleotide sequence having at least 50%, at least 55%, at least 60%, at least 65%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with the nucleotide sequence of SEQ ID NO: 12. In some embodiments, the polypeptide is encoded by a polynucleotide sequence of SEQ ID NO: 12.

In some embodiments, the polypeptide is encoded by a polynucleotide sequence having at least 50%, at least 55%, at least 60%, at least 65%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with the nucleotide sequence of SEQ ID NO: 14. In some embodiments, the polypeptide is encoded by a polynucleotide sequence of SEQ ID NO: 14.

In some embodiments, the polypeptide is encoded by a polynucleotide sequence having at least 50%, at least 55%, at least 60%, at least 65%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with the nucleotide sequence of SEQ ID NO: 16. In some embodiments, the polypeptide is encoded by a polynucleotide sequence of SEQ ID NO: 16.

In some embodiments, the polypeptide is encoded by a polynucleotide sequence having at least 50%, at least 55%, at least 60%, at least 65%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with the nucleotide sequence of SEQ ID NO: 18. In some embodiments, the polypeptide is encoded by a polynucleotide sequence of SEQ ID NO: 18.

In some embodiments, the polypeptide is encoded by a polynucleotide sequence having at least 50%, at least 55%, at least 60%, at least 65%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with the nucleotide sequence of SEQ ID NO: 20. In some embodiments, the polypeptide is encoded by a polynucleotide sequence of SEQ ID NO: 20.

In some embodiments, the polypeptide is encoded by a polynucleotide sequence having at least 50%, at least 55%, at least 60%, at least 65%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with the nucleotide sequence of SEQ ID NO: 22. In some embodiments, the polypeptide is encoded by a polynucleotide sequence of SEQ ID NO: 22.

In some embodiments, the polypeptide is encoded by a polynucleotide sequence having at least 50%, at least 55%, at least 60%, at least 65%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with the nucleotide sequence of SEQ ID NO: 24. In some embodiments, the polypeptide is encoded by a polynucleotide sequence of SEQ ID NO: 24.

In some embodiments, the polypeptide is encoded by a polynucleotide sequence having at least 50%, at least 55%, at least 60%, at least 65%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with the nucleotide sequence of SEQ ID NO: 26. In some embodiments, the polypeptide is encoded by a polynucleotide sequence of SEQ ID NO: 26.

In some embodiments, the polypeptide is encoded by a polynucleotide sequence having at least 50%, at least 55%, at least 60%, at least 65%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with the nucleotide sequence of SEQ ID NO: 28. In some embodiments, the polypeptide is encoded by a polynucleotide sequence of SEQ ID NO: 28.

In some embodiments, the polypeptide is encoded by a polynucleotide sequence having at least 50%, at least 55%, at least 60%, at least 65%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with the nucleotide sequence of SEQ ID NO: 36. In some embodiments, the polypeptide is encoded by a polynucleotide sequence of SEQ ID NO: 36.

In some embodiments, the polypeptide is encoded by a polynucleotide sequence having at least 50%, at least 55%, at least 60%, at least 65%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with the nucleotide sequence of SEQ ID NO: 38. In some embodiments, the polypeptide is encoded by a polynucleotide sequence of SEQ ID NO: 38.

In some embodiments, the polypeptide is encoded by a polynucleotide sequence having at least 50%, at least 55%, at least 60%, at least 65%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with the nucleotide sequence of SEQ ID NO: 40. In some embodiments, the polypeptide is encoded by a polynucleotide sequence of SEQ ID NO: 40.

In some embodiments, the polypeptide is encoded by a polynucleotide sequence having at least 50%, at least 55%, at least 60%, at least 65%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with the nucleotide sequence of SEQ ID NO: 42. In some embodiments, the polypeptide is encoded by a polynucleotide sequence of SEQ ID NO: 42.

The present invention involves the heterologous expression of one or more polypeptides having xylose isomerase activity. It is understood by one of ordinary skill in the art that any polypeptide having xylose isomerase activity or any polynucleotide encoding such a polypeptide may be used according to the present invention. Accordingly, this invention is not limited to the list of example xylose isomerase polypeptides provided. It is understood that nucleotide sequences encoding any of the polypeptides defined above are expressly included in the present invention. Further, any nucleotide sequence that comprises one or more amino acid substitutions, insertions and/or deletions, but that are within the ranges of identity or similarity as defined herein are expressly included in the invention. However, the polypeptides having xylose isomerase activity share certain conserved motifs. In one embodiment, the nucleotide sequence of the invention encodes a xylose isomerase amino acid sequence comprising a xylose isomerase signature sequence as defined, e.g., by Meaden et al. (1994, Gene, 141: 97-101): VXW[GP]GREG[YSTA] (present at positions 188-196, relative to SEQ ID NO: 11) and [LIVM]EPKPX[EQ]P (present at positions 233-240, relative to SEQ ID NO: 11), wherein "X" can be any amino acid and wherein amino acids in brackets indicates that one of the bracketed amino acids can be present at that position in the signature sequence. A xylose isomerase amino acid sequence of the invention can further comprise the conserved amino acid residues His-103, Asp-106, and Asp-341, which constitute a triad directly involved in catalysis, Lys-236 plays a structural as well as a functional catalytic role, and Glu-234 (relative to SEQ ID NO: 11), which is involved in magnesium binding (Vangrysperre et al., "Localization of the essential histidine and carboxylate group in D-xylose isomerases," *Biochem. J.* 265: 699-705(1990); Henrick et al., "Structures of D-xylose isomerase from *Arthrobacter* strain *B*3728 containing the inhibitors xylitol and D-sorbitol at 2.5 A and 2.3 A resolution, respectively," *J. Mol. Biol.* 208: 129-157 (1989); Bhosale et al., "Molecular and industrial aspects of glucose isomerase," *Microbiol. Rev.* 60: 280-300 (1996)). Amino acid positions of the above signature sequences and conserved residues refer to positions in the reference amino acid sequence of the *B. thetaiotaomicron* xylose isomerase of SEQ ID NO: 11. In amino acid sequences of the invention other than SEQ ID NO: 11, the amino acid positions of one or more of the above signature sequences and conserved residues are present in amino acid positions corresponding to the positions of the signature sequences and conserved residues in SEQ ID NO: 11, for example in a ClustalW (1.83 or 1.81) sequence alignment using default settings. The skilled person will know how to identify corresponding amino acid positions in xylose isomerase amino acid sequences other than SEQ ID NO: 11 using amino acid sequence alignment algorithms as defined hereinabove. These regions and positions will tolerate no or only conservative amino acid substitutions. One having ordinary skill in the art would understand that even conserved motifs can remain functional with conservative amino acid substitutions, and such substitutions are envisioned by the present invention. Amino acid substitutions outside of these regions and positions are unlikely to greatly affect xylose isomerase activity.

Additional structural features common to XIs have been described, e.g., by Chang et al., "Crystal Structures of Thermostable Xylose Isomerases from *Thermus caldophilus* and *Thermus thermophiles*: Possible Structural Determinants of Thermostability," *J. Mol. Biol.* 288:623-34 (1999), which is incorporated by reference in its entirety, and RCSB Protein Data Bank, "Xylose Isomerase From *Thermotoga neapolitana*," http://www.rcsb.org/pdb/explore/explore.do?structureId=1A0E, last accessed Jun. 29, 2014, at 5:15 pm. There are several known metal binding sites in the XI sequence, including at residues Glu-234, Glu-270, His-273, Asp-298, Asp-309, Asp-311, and Asp-341. One having ordinary skill in the art would understand that any deletions or non-conservative substitutions at any one or more of these residues may lead to a decreased functionability of the resulting XI.

In some embodiments, a host cell is engineered to express one or more of the xylose isomerase polypeptides. In some embodiments, the host cell is a fungal cell, e.g. a yeast cell, e.g. a *S. cerevisiae* cell. In some embodiments the host cell is modified to have mutations affecting at least one gene encoding a protein of the pentose phosphate pathway. In some embodiments, the host cell has at least one mutation affecting the expression of at least one of XKS1, RKI1, RPE1, TKL1, TAL1, or a combination thereof. In some embodiments, the host cell has one or more mutations that correlate with an increase in the expression or an up-regulation of one or more of XKS1, RKI1, RPE1, TKL1, and/or TAL1. In some embodiments the host cell can be modified through the heterologous expression of one or more polynucleotides encoding XKS1, RKI1, RPE1, TKL1, and/or TAL1. In some embodiments, the host cell has one or more mutations that correlate with a decrease in the expression or down-regulation of one or more of XKS1, RKI1, RPE1, TKL1, and/or TAL1. In some embodiments, the host cell has a modification of an endogenous aldose reductase. In some embodiments, the aldose reductase is GRE3. In some embodiments, the host cell has a deletion or disruption of all or part of the endogenous GRE3 gene. In some embodiments, the aldose reductase gene is YPR1. In some embodiments, the host cell has a deletion or disruption of all or part of the endogenous YPR1 gene. In some embodiments, the host cell has a deletion or disruption of all or part of both the endogenous GRE3 gene and the endogenous YPR1 gene. In some embodiments, the host cell has a modification of PGM1 and/or PGM2. In some embodiments, the host cell overexpresses PGM1 and/or PGM2. In some embodiments, the host cell has increased levels of Pgm1 and/or Pgm2 polypeptide and/or mRNA relative to a comparable host cell lacking a modification of PGM1 and/or PGM2. In some embodiments, the host cell is a modified industrial yeast strain.

In some embodiments, the host cell comprises a deletion or disruption of one or more native enzymes that function to produce glycerol and/or regulate glycerol synthesis as described in, e.g., U.S. Patent Application Publication No. 2014/0186930, which is incorporated by reference herein in its entirety. In some embodiments, the host cell produces less glycerol than a control recombinant microorganism without deletion or disruption of said one or more endogenous enzymes that function to produce glycerol and/or regulate glycerol synthesis. In some embodiments, the one or more endogenous enzymes that function to produce glycerol are encoded by a GPD1 polynucleotide, a GPD2 polynucleotide, or both a GPD1 polynucleotide and a GPD2 polynucleotide. In some embodiments, one or both of the endogenous GPD1 and/or GPD2 genes are modified by mutation or deletion. In some embodiments, the host cell comprises a heterologous ADHE sequence. In some embodiments, the heterologous ADHE is from *Bifidobacterium adolescentis*. In some embodiments the native STL1 gene is upregulated by either modifying the promoter of the native copies or by introducing additional copies of STL1. In some embodiments the host cell comprises an ortholog of the native STL1. In some embodiments the native ACS2 gene is upregulated by either modifying the promoter of the native copies or by introducing additional copies of ACS2. In some embodiments the host cell comprises an ortholog of the native ACS2 or ACS1 gene.

In some embodiments, the host cell comprises one or more mutations in one or more endogenous genes encoding a protein associated with iron metabolism. In some embodiments, the host cell comprises one or more mutations in one or more endogenous genes encoding an iron uptake protein, iron utilization protein, and/or an iron/sulfur (Fe/S) cluster biosynthesis protein. In some embodiments, the host cell comprises one or more mutations in one or more endogenous genes encoding a polypeptide affecting iron metabolism or Fe/S cluster biosynthesis. In some embodiments, the host cell is a recombinant yeast cell. In some embodiments, the recombinant yeast cell comprises one or more mutations in one or more of an endogenous gene selected from the group ISU1, YFH1, NFS1, AFT1, AFT2, YAP5, FRA1, FRA2, GREX3, GREX4, CCC1, and combinations thereof. In some embodiments, the recombinant yeast cell comprises one or more mutations in one or more of an endogenous gene which is homologous to one or more of an *S. cerevisiae* gene selected from the group ISU1, YFH1, NFS1, AFT1, AFT2, YAP5, FRA1, FRA2, GREX3, and GREX4. and CCC1. In some embodiments, the recombinant yeast cell comprises a mutation in the endogenous AFT1 gene that results in iron-independent activation of the iron regulon such as the AFT1-1$^{up}$ or AFT2-1$^{up}$ alleles (Rutherford et al., 2003). In some embodiments, the recombinant yeast cell comprises a deletion or disruption of YAP5 and/or CCC1 and/or a mutation in the endogenous AFT1 or AFT2 gene that results in iron-independent activation of the iron regulon such as the AFT1-1$^{up}$ or AFT2-1$^{up}$ alleles. In some embodiments, the host cell comprises one or more mutations in one or more endogenous genes selected from FRA1, FRA2, GREX3, and GREX4, wherein the one or more mutations results in increased Aft1 and/or Aft2 activity. In some embodiments, the increased Aft1 and/or Aft2 activity results in the increased expression of Aft1 and/or Aft2 target genes. In some embodiments, the one or more mutations in AFT1, AFT2, FRA1, FRA2, GREX3, and/or GREX4 prevent or limit AFT1 and/or AFT2 from forming a complex with Grx3, Grx4, Fra1, and/or Fra2.

In some embodiments, the host cell expresses one or more heterologous genes encoding a protein that is associated with iron metabolism. In some embodiments, the heterologous gene confers on the recombinant yeast cell an increased ability to utilize xylose as compared to a similar yeast cell lacking the heterologous gene. In some embodiments, the heterologous gene is AFT1, AFT2, and/or an orthologue thereof. In some embodiments, the heterologous gene encodes a polypeptide having iron transport activity. In some embodiments, the heterologous gene encodes a protein that increases the activity and/or expression of Aft1 and/or Aft2. In some embodiments, the heterologous gene is a target of Aft1 and/or Aft2. In some embodiments, the heterologous gene is constitutively expressed. In some embodiments, the heterologous gene is overexpressed. In some embodiments, the heterologous gene encodes a protein that suppresses a gene or protein that suppresses Aft1 and/or Aft2 activity and/or expression. In some embodiments, the heterologous gene encodes a protein that suppresses a gene or protein that suppresses the activity and/or expression of one or more downstream targets of Aft1 and/or Aft2.

In some embodiments, the host cell comprises one or more mutations in the endogenous ISU1 gene that results in a polypeptide comprising at least one amino acid substitution selected from the group consisting of D71N, D71G, and S98F, wherein the position of the substitution is relative to the amino acid positions of SEQ ID NO:29. In some embodiments, the host cell comprises one or more mutations in the endogenous YFH1 gene that results in a polypeptide comprising a T163P substitution, wherein the position of the substitution is relative to the amino acid positions of SEQ ID NO:31. In some embodiments, the host cell comprises one or more mutations in the endogenous NFS1 gene that results in a polypeptide comprising at least one amino acid substitution selected from the group consisting of L115W and E458D, wherein the position of the substitution is relative to the amino acid positions of SEQ ID NO:33. In some embodiments, the host cell comprises a mutation in the endogenous ISU1 gene that results in a polypeptide comprising the amino acid substitution D71N, wherein the position of the substitution is relative to the amino acid positions of SEQ ID NO:29; and a mutation in the endogenous YFH1 gene that results in a polypeptide comprising the amino acid substitution T163P, wherein the position of the substitution is relative to the amino acid positions of SEQ ID NO:31. In some embodiments, the mutation is homozygous. In some embodiments, the mutation is heterozygous.

In some embodiments, the host cell comprises (a) one or more mutations in one or more endogenous genes encoding a protein associated with iron metabolism, iron uptake, iron utilization, and/or an iron/sulfur (Fe/S) cluster biosynthesis; and (b) at least one heterologous gene encoding a polypeptide having xylose isomerase activity. In some embodiments, at least one heterologous polypeptide having xylose isomerase activity is a xylose isomerase. One having skill in the art would understand that any number of known xylose isomerase sequences could be expressed in the host cell of the present invention. In some embodiments the xylose isomerase is a naturally occurring xylose isomerase. In some embodiments, the xylose isomerase is a recombinant polypeptide. In some embodiments, the xylose isomerase is a chimeric polypeptide. In some embodiments, the xylose isomerase is encoded by a nucleotide sequence that has at least 80% sequence identity with a nucleotide sequence selected from SEQ ID NOs: 2, 4, 6, 8, 10, 12, 14, 16, 18, 20, 22, 24, 26, and 28. In some embodiments, the xylose isomerase is encoded by a nucleotide sequence that has at least 83% sequence identity with a nucleotide sequence selected from SEQ ID NOs: 2, 4, 6, 8, 10, 12, 14, 16, 18, 20, 22, 24, 26, and 28. In some embodiments, the xylose isomerase is encoded by a nucleotide sequence that has at least 85% sequence identity with a nucleotide sequence selected from SEQ ID NOs: 2, 4, 6, 8, 10, 12, 14, 16, 18, 20, 22, 24, 26, and 28. In some embodiments, the xylose isomerase is encoded by a nucleotide sequence that has at least 87% sequence identity with a nucleotide sequence selected from SEQ ID NOs: 2, 4, 6, 8, 10, 12, 14, 16, 18, 20, 22, 24, 26, and 28. In some embodiments, the xylose isomerase is encoded by a nucleotide sequence that has at least 90% sequence identity with a nucleotide sequence selected from SEQ ID NOs: 2, 4, 6, 8, 10, 12, 14, 16, 18, 20, 22, 24, 26, and 28. In some embodiments, the xylose isomerase is encoded by a nucleotide sequence that has at least 91% sequence identity with a nucleotide sequence selected from SEQ ID NOs: 2, 4, 6, 8, 10, 12, 14, 16, 18, 20, 22, 24, 26, and 28. In some embodiments, the xylose isomerase is encoded by a nucleotide sequence that has at least 92% sequence identity with a nucleotide sequence selected from SEQ ID NOs: 2, 4, 6, 8, 10, 12, 14, 16, 18, 20, 22, 24, 26, and 28. In some embodiments, the xylose isomerase is encoded by a nucleotide sequence that has at least 93% sequence identity with a nucleotide sequence selected from SEQ ID NOs: 2, 4, 6, 8, 10, 12, 14, 16, 18, 20, 22, 24, 26, and 28. In some embodiments, the xylose isomerase is encoded by a nucleotide sequence that has at least 94% sequence identity with a nucleotide sequence selected from SEQ ID NOs: 2, 4, 6, 8, 10, 12, 14, 16, 18, 20, 22, 24, 26, and 28. In some embodiments, the xylose isomerase is encoded by a nucleotide sequence that has at least 95% sequence identity with a nucleotide sequence selected from SEQ ID NOs: 2, 4, 6, 8, 10, 12, 14, 16, 18, 20, 22, 24, 26, and 28. In some embodiments, the xylose isomerase is encoded by a nucleotide sequence that has at least 96% sequence identity with a nucleotide sequence selected from SEQ ID NOs: 2, 4, 6, 8, 10, 12, 14, 16, 18, 20, 22, 24, 26, and 28. In some embodiments, the xylose isomerase is encoded by a nucleotide sequence that has at least 97% sequence identity with a nucleotide sequence selected from SEQ ID NOs: 2, 4, 6, 8, 10, 12, 14, 16, 18, 20, 22, 24, 26, and 28. In some embodiments, the xylose isomerase is encoded by a nucleotide sequence that has at least 98% sequence identity with a nucleotide sequence selected from SEQ ID NOs: 2, 4, 6, 8, 10, 12, 14, 16, 18, 20, 22, 24, 26, and 28. In some embodiments, the xylose isomerase is encoded by a nucleotide sequence that has at least 99% sequence identity with a nucleotide sequence selected from SEQ ID NOs: 2, 4, 6, 8, 10, 12, 14, 16, 18, 20, 22, 24, 26, and 28. In some embodiments, the xylose isomerase is encoded by a nucleotide sequence that has at least 100% sequence identity with a nucleotide sequence selected from SEQ ID NOs: 2, 4, 6, 8, 10, 12, 14, 16, 18, 20, 22, 24, 26, and 28.

In some embodiments, the xylose isomerase is encoded by a nucleotide sequence that has at least 80% sequence identity with a nucleotide sequence selected from SEQ ID NOs: 2, 4, 6, 8, 10, 12, 14, 16, 18, 20, 22, 24, 26, 28, 36, 38, 40, and 42. In some embodiments, the xylose isomerase is encoded by a nucleotide sequence that has at least 83% sequence identity with a nucleotide sequence selected from SEQ ID NOs: 2, 4, 6, 8, 10, 12, 14, 16, 18, 20, 22, 24, 26, 28, 36, 38, 40, and 42. In some embodiments, the xylose isomerase is encoded by a nucleotide sequence that has at least 85% sequence identity with a nucleotide sequence selected from SEQ ID NOs: 2, 4, 6, 8, 10, 12, 14, 16, 18, 20, 22, 24, 26, 28, 36, 38, 40, and 42. In some embodiments, the xylose isomerase is encoded by a nucleotide sequence that has at least 87% sequence identity with a nucleotide sequence selected from SEQ ID NOs: 2, 4, 6, 8, 10, 12, 14, 16, 18, 20, 22, 24, 26, 28, 36, 38, 40, and 42. In some embodiments, the xylose isomerase is encoded by a nucleotide sequence that has at least 90% sequence identity with a nucleotide sequence selected from SEQ ID NOs: 2, 4, 6, 8, 10, 12, 14, 16, 18, 20, 22, 24, 26, 28, 36, 38, 40, and 42. In some embodiments, the xylose isomerase is encoded by a nucleotide sequence that has at least 91% sequence identity with a nucleotide sequence selected from SEQ ID NOs: 2, 4, 6, 8, 10, 12, 14, 16, 18, 20, 22, 24, 26, 28, 36, 38, 40, and 42. In some embodiments, the xylose isomerase is encoded by a nucleotide sequence that has at least 92% sequence identity with a nucleotide sequence selected from SEQ ID NOs: 2, 4, 6, 8, 10, 12, 14, 16, 18, 20, 22, 24, 26, 28, 36, 38, 40, and 42. In some embodiments, the xylose isomerase is encoded by a nucleotide sequence that has at least 93% sequence identity with a nucleotide sequence selected from SEQ ID NOs: 2, 4, 6, 8, 10, 12, 14, 16, 18, 20, 22, 24, 26, 28, 36, 38, 40, and 42. In some embodiments, the xylose isomerase is encoded by a nucleotide sequence that has at least 94% sequence identity with a nucleotide sequence selected from SEQ ID NOs: 2, 4, 6, 8, 10, 12, 14, 16, 18, 20, 22, 24, 26, 28, 36, 38, 40, and 42. In some embodiments, the xylose isomerase is encoded by a nucleotide sequence that has at least 95% sequence identity with a nucleotide sequence selected from SEQ ID NOs: 2, 4, 6, 8, 10, 12, 14, 16, 18, 20, 22, 24, 26, 28, 36, 38, 40, and 42. In some embodiments, the xylose isomerase is encoded by a nucleotide sequence that has at least 96% sequence identity with a nucleotide sequence selected from SEQ ID NOs: 2, 4, 6, 8, 10, 12, 14, 16, 18, 20, 22, 24, 26, 28, 36, 38, 40, and 42. In some embodiments, the xylose isomerase is encoded by a nucleotide sequence that has at least 97% sequence identity with a nucleotide sequence selected from SEQ ID NOs: 2, 4, 6, 8, 10, 12, 14, 16, 18, 20, 22, 24, 26, 28, 36, 38, 40, and 42. In some embodiments, the xylose isomerase is encoded by a nucleotide sequence that has at least 98% sequence identity with a nucleotide sequence selected from SEQ ID NOs: 2, 4, 6, 8, 10, 12, 14, 16, 18, 20, 22, 24, 26, 28, 36, 38, 40, and 42. In some embodiments, the xylose isomerase is encoded by a nucleotide sequence that has at least 99% sequence identity with a nucleotide sequence selected from SEQ ID NOs: 2, 4, 6, 8, 10, 12, 14, 16, 18, 20, 22, 24, 26, 28, 36, 38, 40, and 42. In some embodiments, the xylose isomerase is encoded by a nucleotide sequence that has at least 100% sequence identity with a nucleotide sequence selected from SEQ ID NOs: 2, 4, 6, 8, 10, 12, 14, 16, 18, 20, 22, 24, 26, 28, 36, 38, 40, and 42.

In some embodiments, the xylose isomerase has an amino acid sequence that has at least 80% sequence identity with an amino acid sequence selected from SEQ ID NOs: 1, 3, 5, 7, 9, 11, 13, 15, 17, 19, 21, 23, 25, and 27. In some embodiments, the xylose isomerase has an amino acid sequence that has at least 83% sequence identity with an amino acid sequence selected from SEQ ID NOs: 1, 3, 5, 7, 9, 11, 13, 15, 17, 19, 21, 23, 25, and 27. In some embodiments, the xylose isomerase has an amino acid sequence that has at least 85% sequence identity with an amino acid sequence selected from SEQ ID NOs: 1, 3, 5, 7, 9, 11, 13, 15, 17, 19, 21, 23, 25, and 27. In some embodiments, the xylose isomerase has an amino acid sequence that has at least 87% sequence identity with an amino acid sequence selected from SEQ ID NOs: 1, 3, 5, 7, 9, 11, 13, 15, 17, 19, 21, 23, 25, and 27. In some embodiments, the xylose isomerase has an amino acid sequence that has at least 90% sequence identity with an amino acid sequence selected from SEQ ID NOs: 1, 3, 5, 7, 9, 11, 13, 15, 17, 19, 21, 23, 25, and 27. In some embodiments, the xylose isomerase has an amino acid sequence that has at least 91% sequence identity with an amino acid sequence selected from SEQ ID NOs: 1, 3, 5, 7, 9, 11, 13, 15, 17, 19, 21, 23, 25, and 27. In some embodiments, the xylose isomerase has an amino acid sequence that has at least 92% sequence identity with an amino acid sequence selected from SEQ ID NOs: 1, 3, 5, 7, 9, 11, 13, 15, 17, 19, 21, 23, 25, and 27. In some embodiments, the xylose isomerase has an amino acid sequence that has at least 93% sequence identity with an amino acid sequence selected from SEQ ID NOs: 1, 3, 5, 7, 9, 11, 13, 15, 17, 19, 21, 23, 25, and 27. In some embodiments, the xylose isomerase has an amino acid sequence that has at least 94% sequence identity with an amino acid sequence selected from SEQ ID NOs: 1, 3, 5, 7, 9, 11, 13, 15, 17, 19, 21, 23, 25, and 27. In some embodiments, the xylose isomerase has an amino acid sequence that has at least 95% sequence identity with an amino acid sequence selected from SEQ ID NOs: 1, 3, 5, 7, 9, 11, 13, 15, 17, 19, 21, 23, 25, and 27. In some embodiments, the xylose isomerase has an amino acid sequence that has at least 96% sequence identity with an amino acid sequence selected from SEQ ID NOs: 1, 3, 5, 7, 9, 11, 13, 15, 17, 19, 21, 23, 25, and 27. In some embodiments, the xylose isomerase has an amino acid sequence that has at least 97% sequence identity with an amino acid sequence selected from SEQ ID NOs: 1, 3, 5, 7, 9, 11, 13, 15, 17, 19, 21, 23, 25, and 27. In some embodiments, the xylose isomerase has an amino acid sequence that has at least 98% sequence identity with an amino acid sequence selected from SEQ ID NOs: 1, 3, 5, 7, 9, 11, 13, 15, 17, 19, 21, 23, 25, and 27. In some embodiments, the xylose isomerase has an amino acid sequence that has at least 99% sequence identity with an amino acid sequence selected from SEQ ID NOs: 1, 3, 5, 7, 9, 11, 13, 15, 17, 19, 21, 23, 25, and 27. In some embodiments, the xylose isomerase has an amino acid sequence that has at least 10% sequence identity with an amino acid sequence selected from SEQ ID NOs: 1, 3, 5, 7, 9, 11, 13, 15, 17, 19, 21, 23, 25, and 27.

In some embodiments, the xylose isomerase has an amino acid sequence that has at least 80% sequence identity with an amino acid sequence selected from SEQ ID NOs: 1, 3, 5, 7, 9, 11, 13, 15, 17, 19, 21, 23, 25, 27, 35, 37, 39, and 41. In some embodiments, the xylose isomerase has an amino acid sequence that has at least 83% sequence identity with an amino acid sequence selected from SEQ ID NOs: 1, 3, 5, 7, 9, 11, 13, 15, 17, 19, 21, 23, 25, 27, 35, 37, 39, and 41. In some embodiments, the xylose isomerase has an amino acid sequence that has at least 85% sequence identity with an amino acid sequence selected from SEQ ID NOs: 1, 3, 5, 7, 9, 11, 13, 15, 17, 19, 21, 23, 25, 27, 35, 37, 39, and 41. In some embodiments, the xylose isomerase has an amino acid sequence that has at least 87% sequence identity with an amino acid sequence selected from SEQ ID NOs: 1, 3, 5, 7, 9, 11, 13, 15, 17, 19, 21, 23, 25, 27, 35, 37, 39, and 41. In some embodiments, the xylose isomerase has an amino acid sequence that has at least 90% sequence identity with an amino acid sequence selected from SEQ ID NOs: 1, 3, 5, 7, 9, 11, 13, 15, 17, 19, 21, 23, 25, 27, 35, 37, 39, and 41. In some embodiments, the xylose isomerase has an amino acid sequence that has at least 91% sequence identity with an amino acid sequence selected from SEQ ID NOs: 1, 3, 5, 7, 9, 11, 13, 15, 17, 19, 21, 23, 25, 27, 35, 37, 39, and 41 43. In some embodiments, the xylose isomerase has an amino acid sequence that has at least 92% sequence identity with an amino acid sequence selected from SEQ ID NOs: 1, 3, 5, 7, 9, 11, 13, 15, 17, 19, 21, 23, 25, 27, 35, 37, 39, and 41. In some embodiments, the xylose isomerase has an amino acid sequence that has at least 93% sequence identity with an amino acid sequence selected from SEQ ID NOs: 1, 3, 5, 7, 9, 11, 13, 15, 17, 19, 21, 23, 25, 27, 35, 37, 39, and 41. In some embodiments, the xylose isomerase has an amino acid sequence that has at least 94% sequence identity with an amino acid sequence selected from SEQ ID NOs: 1, 3, 5, 7, 9, 11, 13, 15, 17, 19, 21, 23, 25, 27, 35, 37, 39, and 41. In some embodiments, the xylose isomerase has an amino acid sequence that has at least 95% sequence identity with an amino acid sequence selected from SEQ ID NOs: 1, 3, 5, 7, 9, 11, 13, 15, 17, 19, 21, 23, 25, 27, 35, 37, 39, and 41. In some embodiments, the xylose isomerase has an amino acid sequence that has at least 96% sequence identity with an amino acid sequence selected from SEQ ID NOs: 1, 3, 5, 7, 9, 11, 13, 15, 17, 19, 21, 23, 25, 27, 35, 37, 39, and 41. In some embodiments, the xylose isomerase has an amino acid sequence that has at least 97% sequence identity with an amino acid sequence selected from SEQ ID NOs: 1, 3, 5, 7, 9, 11, 13, 15, 17, 19, 21, 23, 25, 27, 35, 37, 39, and 41. In some embodiments, the xylose isomerase has an amino acid sequence that has at least 98% sequence identity with an amino acid sequence selected from SEQ ID NOs: 1, 3, 5, 7, 9, 11, 13, 15, 17, 19, 21, 23, 25, 27, 35, 37, 39, and 41 43. In some embodiments, the xylose isomerase has an amino acid sequence that has at least 99% sequence identity with an amino acid sequence selected from SEQ ID NOs: 1, 3, 5, 7, 9, 11, 13, 15, 17, 19, 21, 23, 25, 27, 35, 37, 39, and 41. In some embodiments, the xylose isomerase has an amino acid sequence that has at least 10% sequence identity with an amino acid sequence selected from SEQ ID NOs: 1, 3, 5, 7, 9, 11, 13, 15, 17, 19, 21, 23, 25, 27, 35, 37, 39, and 41.

In some embodiments, the host cell comprises (a) one or mutation in the endogenous YFH1 gene that results in a polypeptide comprising a T163P substitution; and (b) at least one heterologous gene encoding a polypeptide having xylose isomerase activity, wherein the polypeptide has an amino acid sequence at least about 80%, at least about 83%, at least about 85%, at least about 87%, at least about 90%, at least about 91%, at least about 92%, at least about 93%, at least about 94%, at least about 95%, at least about 96%, at least about 97%, at about least 98%, at about least 99%, or about 100% identical to the amino acid sequence of SEQ ID NO:1. In some embodiments, the host cell comprises (a) a deletion or disruption of GRE3 and/or YPR1; (b) one or more mutations that correlate with an increase in the expression or up-regulation of one or more of XKS1, RKI1, RPE1, TKL1, TAL1, PGM1 and/or PGM2; (c) one or mutation in the endogenous YFH1 gene that results in a polypeptide comprising a T163P substitution; and (d) at least one heterologous gene encoding a polypeptide having xylose isomerase activity, wherein the polypeptide has an amino acid sequence at least about 80%, at least about 83%, at least about 85%, at least about 87%, at least about 90%, at least about 91%, at least about 92%, at least about 93%, at least about 94%, at least about 95%, at least about 96%, at least about 97%, at about least 98%, at about least 99%, or about 100% identical to the amino acid sequence of SEQ ID NO:1. In some embodiments, the host cell can be cultured in a medium supplemented with iron. In some embodiments, the host cell can be cultured under conditions that facilitate and/or stimulate the uptake of iron by the host cell. In some embodiments, the host cell can be cultured under conditions that hinder, prevent, block, and/or decrease the export of iron from the host cell.

In some embodiments, the host cell comprises more than one copy of the polynucleotide encoding the polypeptide having xylose isomerase activity. In some embodiments, the host cell comprises two copies, three copies, four copies, five copies, six copies, seven copies, eight copies, nine copies, ten copies, eleven copies, at least twelve copies, at least fifteen copies, or at least twenty copies of the polynucleotide encoding the polypeptide having xylose isomerase activity.

In some embodiments, the polynucleotide can be present in a vector. In some embodiments, the host cell can comprise the polynucleotide within a vector. In some embodiments, the vector is a plasmid. In some embodiments, the host cell can express the polynucleotide from the vector. In some embodiments, the polynucleotide can be incorporated into the genome of the host cell. In some embodiments, the host cell is a fungal cell. In some embodiments, the host cell is a yeast cell. In some embodiments, the host cell is a *S. cerevisiae* cell.

Certain embodiments of the present invention describe methods for producing a fermentation product. In certain embodiments, the recombinant host cell comprising the polynucleotide or the polypeptide and a mutation in one or more genes encoding a protein associated with iron metabolism is contacted with a carbon source. In some embodiments, the host cell comprises a mutation in one or more genes encoding a protein associated with iron metabolism, and the host cell is contacted with a carbon source and an exogenous source of a polypeptide having xylose isomerase activity. In certain embodiments, the carbon source comprises xylose. In certain embodiments, xylose is the sole source of carbon in the carbon source. In certain embodiments, a fermentation product is produced by contacting the host cell with the carbon source. In certain embodiments, the fermentation product is recovered. In certain embodiments, the fermentation product is selected from the group consisting of ethanol, lactic acid, 3-hydroxy-propionic acid, hydrogen, butyric acid, acrylic acid, acetic acid, succinic acid, citric acid, malic acid, fumaric acid, an amino acid, 1,3-propane-diol, ethylene, glycerol, acetone, isopropyl alcohol, butanol, a β-lactam, an antibiotic, cephalosporin, or a combination thereof. In certain embodiments, the fermentation product is ethanol.

IV. Codon-Optimization

In some embodiments, the nucleotide sequence of the one or more polynucleotides disclosed in the present invention are codon-optimized for expression in a fungal host cell. In some embodiments, the nucleotide sequence of the polynucleotide is codon-optimized for expression in a yeast host cell. In some embodiments the nucleotide sequence of the polynucleotide is codon-optimized for expression in *S. cerevisiae*. Codon-optimized polynucleotides can have a codon adaptation index (CAI) of about 0.8 to 1.0, about 0.9 to 1.0, or about 0.95 to 1.0.

In general, highly expressed genes in an organism are biased towards codons that are recognized by the most abundant tRNA species in that organism. One measure of this bias is the "codon adaptation index" or "CAI," which measures the extent to which the codons used to encode each amino acid in a particular gene are those which occur most frequently in a reference set of highly expressed genes from an organism. The Codon Adaptation Index is described in more detail in Sharp and Li, *Nucleic Acids Research* 15:1281-1295 (1987), which is incorporated by reference herein in its entirety.

The CAI of codon-optimized sequences used in the present invention corresponds to from about 0.6 to about 1.0, from about 0.7 to about 1.0, from about 0.8 to about 1.0, from about 0.9 to about 1.0, from about 9.5 to about 1.0, or about 1.0. A codon-optimized sequence can be further modified for expression in a particular organism, depending on that organism's biological constraints. For example, large runs of "As" or "Ts" (e.g., runs greater than 4, 5, 6, 7, 8, 9, or 10 consecutive bases) can be removed from the sequences if these are known to effect transcription negatively. Furthermore, specific restriction enzyme sites can be removed for molecular cloning purposes. Examples of such restriction enzyme sites include Pad, Ascl, BamHI, BgIII, EcoRJ and Xhol. Additionally, the DNA sequence can be checked for direct repeats, inverted repeats and mirror repeats with lengths of ten bases or longer, which can be modified manually by replacing codons with "second best" codons, i.e., codons that occur at the second highest frequency within the particular organism for which the sequence is being optimized.

Deviations in the nucleotide sequence that comprise the codons encoding the amino acids of any polypeptide chain allow for variations in the sequence coding for the gene. Since each codon consists of three nucleotides, and the nucleotides comprising DNA are restricted to four specific bases, there are 64 possible combinations of nucleotides, 61 of which encode amino acids (the remaining three codons encode signals ending translation). The "genetic code" which shows which codons encode which amino acids is well known to one of skill in the art. As a result, many amino acids are designated by more than one codon. For example, the amino acids alanine and proline are coded for by four triplets, serine and arginine by six, whereas tryptophan and methionine are coded by just one triplet. This degeneracy allows for DNA base composition to vary over a wide range without altering the amino acid sequence of the proteins encoded by the DNA.

Many organisms display a bias for use of particular codons to code for insertion of a particular amino acid in a growing peptide chain. Codon preference or codon bias, differences in codon usage between organisms, is afforded by degeneracy of the genetic code, and is well documented among many organisms. Codon bias often correlates with the efficiency of translation of messenger RNA (mRNA), which is in turn believed to be dependent on, inter alia, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization.

Given the large number of gene sequences available for a wide variety of animal, plant and microbial species, it is possible to calculate the relative frequencies of codon usage. Codon usage tables and codon-optimizing programs are readily available, for example, at http://www.kazusa.or.jp/codon/ (visited Jul. 15, 2014), and these tables can be adapted in a number of ways. See, e.g., Nakamura, Y., et al. "Codon usage tabulated from the international DNA sequence databases: status for the year 2000," Nucl. Acids Res. 28:292 (2000).

By utilizing one or more available tables, one of ordinary skill in the art can apply the frequencies to any given polypeptide sequence, and produce a nucleic acid fragment of a codon-optimized coding region which encodes the polypeptide, but which uses codons optimal for a given species. Codon-optimized coding regions can be designed by various different methods known to one having ordinary skill in the art.

In certain embodiments, an entire polypeptide sequence, or fragment, variant, or derivative thereof is codon-optimized by any method known in the art. Various desired fragments, variants or derivatives are designed, and each is then codon-optimized individually. In addition, partially codon-optimized coding regions of the present invention can be designed and constructed. For example, the invention includes a nucleic acid fragment of a codon-optimized coding region encoding a polypeptide in which at least about 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, or 100% of the codon positions have been codon-optimized for a given species. That is, they contain a codon that is preferentially used in the genes of a desired species, e.g., a yeast species such as S. cerevisiae, in place of a codon that is normally used in the native nucleic acid sequence.

In additional embodiments, a full-length polypeptide sequence is codon-optimized for a given species resulting in a codon-optimized coding region encoding the entire polypeptide, and then nucleic acid fragments of the codon-optimized coding region, which encode fragments, variants, and derivatives of the polypeptide are made from the original codon-optimized coding region. As would be well understood by those of ordinary skill in the art, if codons have been randomly assigned to the full-length coding region based on their frequency of use in a given species, nucleic acid fragments encoding fragments, variants, and derivatives would not necessarily be fully codon-optimized for the given species. However, such sequences are still much closer to the codon usage of the desired species than the native codon usage. The advantage of this approach is that synthesizing codon-optimized nucleic acid fragments encoding each fragment, variant, and derivative of a given polypeptide, although routine, would be time consuming and would result in significant expense.

In some embodiments, one or more of the donor parent polynucleotide sequences are codon-optimized for expression in yeast. In some embodiments, the chimeric polynucleotide is codon-optimized for expression in yeast.

V. Methods of Producing Ethanol

Certain aspects of the present invention are directed to methods of producing a fermentation product. In some embodiments of the invention, the recombinant host cell is used to produce a fermentation product from a cellulosic or lignocellulosic material. In some embodiments, the fermentation product is ethanol, lactic acid, 3-hydroxy-propionic acid, hydrogen, butyric acid, acrylic acid, acetic acid, succinic acid, citric acid, malic acid, fumaric acid, an amino acid, 1,3-propane-diol, ethylene, glycerol, acetone, isopropyl alcohol, butanol, a β-lactam, an antibiotic, a cephalosporin, or a combination thereof. In some embodiments, the cellulosic or lignocellulosic material is insoluble cellulose, crystalline cellulose, pretreated hardwood, paper sludge, pretreated corn stover, pretreated sugar cane bagasse, pretreated corn cobs, pretreated switchgrass, pretreated municipal solid waste, pretreated distiller's dried grains, pretreated wheat straw, corn fiber, agave, or a combination thereof.

One aspect of the invention is directed to a composition comprising a lignocellulosic material and a recombinant yeast host cell comprising at least one polypeptide having xylose isomerase activity and comprising a mutation in a gene encoding a protein associated with iron metabolism. Another aspect of the invention is directed to a media supernatant generated by incubating a recombinant yeast host comprising as least one polypeptide having xylose isomerase activity and comprising a mutation in a gene encoding a protein associated with iron metabolism with a medium containing xylose as the only carbon source. In some embodiments, the medium comprises a cellulosic or lignocellulosic material. In some embodiments, the cellulosic or lignocellulosic material is insoluble cellulose, crystalline cellulose, pretreated hardwood, paper sludge, saw mill or paper mill discards, pretreated corn stover, pretreated sugar cane bagasse, pretreated corn cobs, pretreated switchgrass, pretreated municipal solid waste, pretreated distiller's dried grains, pretreated wheat straw, corn fiber, agave, or a combination thereof.

In some embodiments, a fermentation product is produced by a method comprising contacting a recombinant host cell of the present invention with a carbon source, wherein the carbon source comprises xylose. In some embodiments, the fermentation product is selected from the group consisting of ethanol, lactic acid, 3-hydroxy-propionic acid, hydrogen, butyric acid, acrylic acid, acetic acid, succinic acid, citric acid, malic acid, fumaric acid, an amino acid, 1,3-propanediol, ethylene, glycerol, acetone, isopropyl alcohol, butanol, a β-lactam, an antibiotic, and a cephalosporin. In some embodiments, the fermentation product is ethanol. In some embodiments, the fermentation product is recovered.

Certain aspects of the present invention are directed to a method of producing ethanol comprising contacting a source material comprising xylose with a host cell of the present invention. In some embodiments the host cell heterologously expresses a polypeptide having xylose isomerase activity. In some embodiments the host cell further comprises a mutation in one or more genes encoding a polypeptide that is associated with iron metabolism.

In some embodiments, the source material is a cellulosic biomass. In some embodiments, the source material is a lignocellulosic biomass. In some embodiments, the source material is selected from the group consisting of insoluble cellulose, crystalline cellulose, pretreated hardwood, softwood, paper sludge, newspaper, sweet sorghum, pretreated corn stover, pretreated sugar cane bagasse, pretreated corn cobs, pretreated switchgrass, pretreated municipal solid waste, pretreated distiller's dried grains, pretreated wheat straw, rice straw, nut shells, banana waste, sponge gourd fibers, corn fiber, agave, trees, corn stover, wheat straw, sugar cane bagasse, switchgrass, and combinations thereof. In some embodiments, the source material is corn stover.

EXAMPLES

The invention now being generally described, it will be more readily understood by reference to the following examples, which are included merely for purposes of illustration of certain aspect and embodiments of the present invention, and are not intended to limit the invention.

Example 1—S. cerevisiae Background Strain

A strain of S. cerevisiae was created that was suitable for the testing of functional xylose isomerases. The GRE3 locus of an industrial yeast strain was replaced with expression cassettes for the pentose phosphate pathway genes RPE1, RKI1, TKL1, and TAL1 as well as the native S. cerevisiae xyulokinase XKS1 (FIG. 1).

Example 2—Identification of Iron Metabolism Related Genes Mutated in Xylose Utilizing Strains Specific mutations in three native S. cerevisiae genes (ISU1, YFH1, and NFS1) were identified that significantly improve performance of XI xylose engineered strains. The mutations were identified by reverse engineering several strains adapted for improved growth rate on xylose media. The adapted strains were derived from strains engineered to express an exogenous XI and to overexpress the native genes XKS, RKI1, RPE1, TAL1, and TKL1. Two strains were adapted that differed in the native GRE3+ locus, with one strain having a deletion of the endogenous GRE3. The mutations can be directly engineered into a strain providing the performance improvements usually obtained via adaptation. The directed engineering of these mutations saves the time and uncertainty associated with strain adaptations. These mutations can benefit strains engineered with various XIs (see FIGS. 5 and 6).

Example 3—Mutations in YFH1, ISU1, and NFS1 Improve Growth on Xylose

Strains were grown on YPX media (yeast extract, peptone, and xylose) under anaerobic conditions in a Biotek plate reader. OD600 measurements were used to determine changes in cell density over time (~48 hrs) (FIG. 3). Xylose Utilizing Strains (XUS) 1 and 2 are strains engineered to utilize xylose but without mutations in YFH1, ISU1, or NFS1. XUS1-1 and XUS1-2 strains were adapted for improved growth on xylose originating from strain XUS1. Strain XUS2-1 was adapted for improved growth on xylose originating from strain XUS2. Genome sequencing revealed mutations in iron-sulfur cluster related genes in the adapted strains XUS1-1 (YFH1), XUS1-2 (NFS1) and XUS2-1 (ISU1). Direct genetic engineering to revert the mutations to the wild type alleles (XUS1-1→YFH1 wt, XUS2-1→ISU1 wt, XUS1-2→NFS1 wt) decreased xylose growth, matching the original parent strains. Direct genetic engineering of the iron-sulfur mutations into the parent strains (XUS1→YFH1 T163P, XUS2→ISU1 D71N, XUS1→NFS1 L115W) resulted in improved xylose growth matching the adapted strains with the same parent and mutation. The ISU1 D71N mutation was direct engineered as a heterozygote to match the mutation found in the adapted strain XUS2-1.

Example 4—Homozygousing the ISU1$^{D71N}$ Mutation Improves Growth on Xylose

Strains were grown on YPX media (yeast extract, peptone, and xylose) under anaerobic conditions in a Biotek plate reader. OD600 measurements were used to determine changes in cell density over time (~48 hrs) (FIG. 4A). The negative control is a strain that is unable to grow on xylose. Adapted strain XUS2-1 is heterozygous at the ISU1 locus. XUS2-1 genetically engineered with two mutant alleles of ISU1$^{D71N}$ (XUS2-1+ISU1* homo) exhibits improved growth on xylose relative to the original heterozygote XUS2-1. Engineering the original parent strain with two mutant alleles of ISU1$^{D71N}$(XUS2+ISU1* homo) results in improved xylose growth equivalent to the XUS2-1 ISU1$^{D71N}$ homozygote.

Example 5—The Homozygous ISU1$^{D71N}$ Mutation Improves Growth of the XUS1 GRE3$^+$ Parent Strain Strains were grown on YPX media (yeast extract, peptone, and xylose) under anaerobic conditions in a Biotek plate reader. OD600 measurements were used to determine changes in cell density over time (~48 hrs) (FIG. 4B). The negative control is a strain that is unable to grow on xylose. The ISU1$^{D71N}$ mutation was identified as a heterozygous mutation in an adapted xylose—utilizing strain with GRE3 deleted (XUS2-1). Direct engineering of the ISU1$^{D71N}$ heterozygous mutation into the GRE3$^+$ xylose strain XUS1 did not improve xylose growth (data not shown). Engineering XUS1 strain with two mutant alleles of ISU1$^{D71N}$(XUS1+ISU1* homo) results in significantly improved xylose growth equivalent to the XUS2 directly engineered ISU1$^{D71N}$homozygote (XUS2+ISU1* homo). Strain XUS1-1 is an adapted version of XUS1 containing a homozygous mutation in YFH1. XUS1-1 directly engineered homozygous ISU1$^{D71N}$ exhibits decreased performance.

Example 6—The YFH1$^{T163P}$ Mutation Improves Growth of the Yeast Strains Heterologously Expressing Various XIs Strains were grown on YNBX minimal media, and the OD600 was measured following 48 hours of aerobic growth at 35° C. (FIG. 5). Various XIs were expressed on plasmids within the industrial host strain used for the chimeric XI library (black bars) or the host strain plus the YFH1 T163P Fe/Su cluster mutation (hashed bars). Eight colonies from each transformation were inoculated into YNBX media. Nearly all of the XIs that generated growth above the negative control, which lacked an XI, showed a benefit from the presence of the YFH1 mutant allele.

Figure 6:
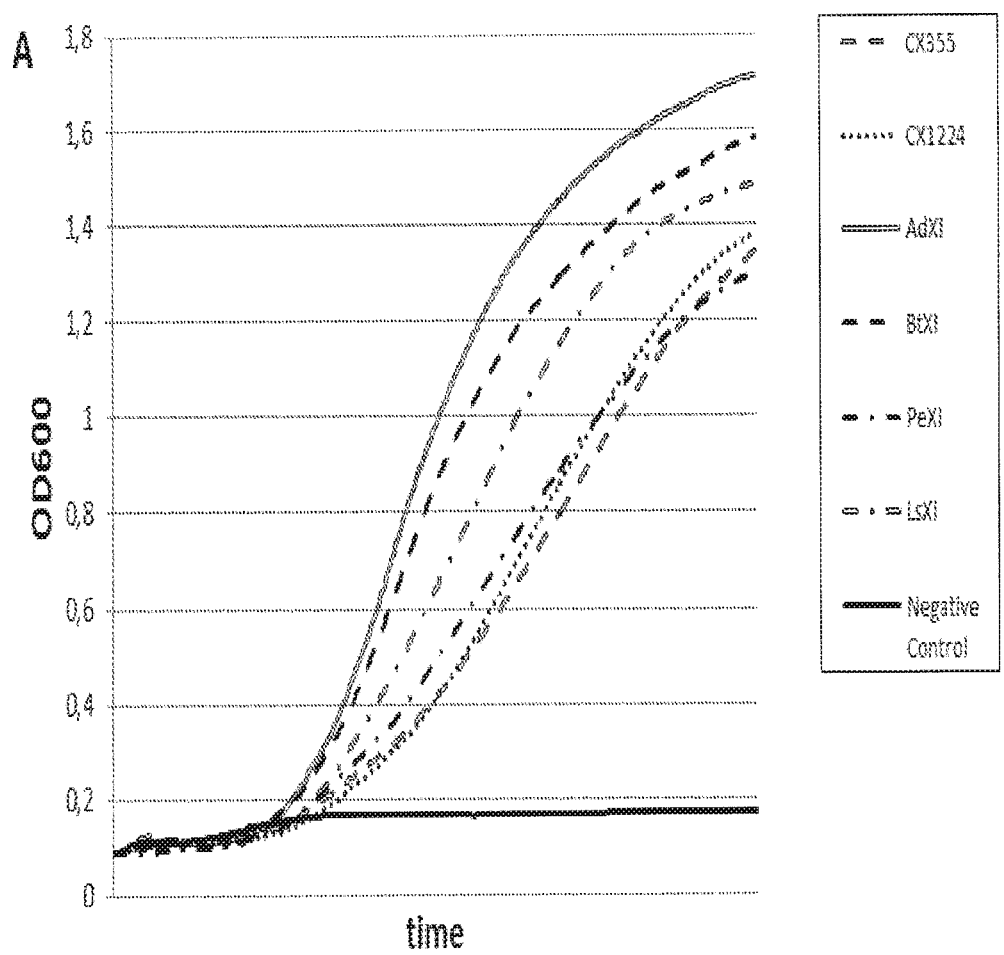
Figure 6:
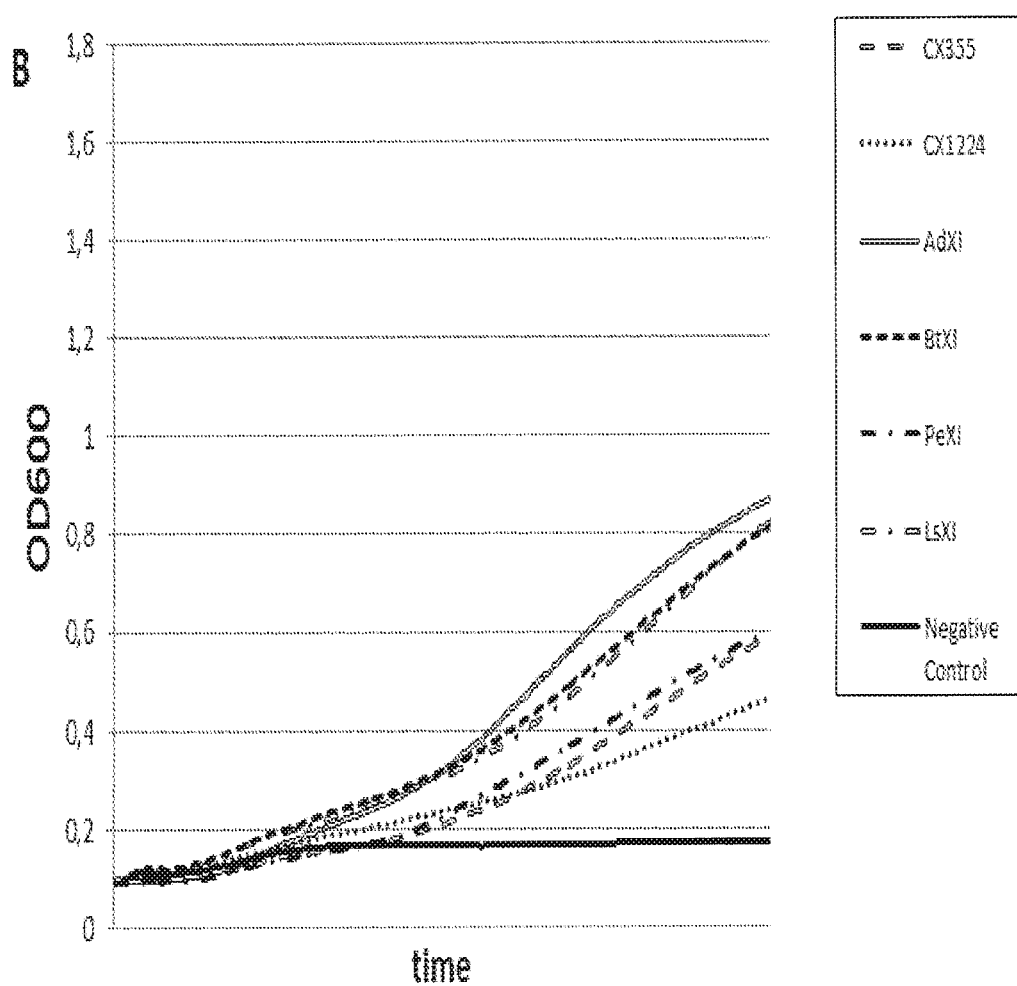

In a second set of experiments, strains were grown on YPX media (yeast extract, peptone, xylose) under anaerobic conditions in a Biotek plate reader at 35° C. OD600 measurements were used to determine changes in cell density over time (~48 hours) (FIGS. 6 A and B). The negative control is a strain unable to grow on xylose. FIG. 6A shows strains containing the wild type allele of YFH1. FIG. 6B shows strains containing the YFH1T163P allele. All of the XIs tested using this genomic integration format showed significantly improved growth on xylose with the YFH1T163P allele present. CX355=chimeric xylose isomerase 355, CX1224=chimeric xylose isomerase 1224, Ad=Abiotrophia defectiva, Bt=Bacteriodes thetaioatomicron, Pe=Piromyces, Ls=*Lachnoanaerobaculum saburreum*

Example 7—Mutations in AFT1 and CCC1 Improve Xylose Growth

Strains were grown on YPX media (yeast extract, peptone, and xylose) under anaerobic conditions in a Biotek plate reader. OD600 measurements were used to determine changes in cell density over time (~48 hrs) (FIG. 7). The negative control is a strain that is unable to grow on xylose. Xylose utilizing strain (XUS) is a strain engineered to utilize xylose. XUS1-1 strain was adapted for improved growth on xylose originating from strain XUS1 and was found by genome sequencing to contain a mutation in iron-sulfur cluster related gene YFH1; XUS1-1 serves as a positive control. Direct engineering of the AFT1-1UP allele into the XUS1 strain (XUS1+AFT1-1UP) slightly improved growth on xylose. Direct engineering of the AFT1-1UP allele into and deletion of both endogenous copies of CCC1 in the XUS1 strain (XUS1; +AFT1-1UP, ccc1Δ) result in significantly improved xylose growth close to that of the XUS1-1 strain.

Example 8—Addition of Iron Improves Growth on Xylose

Strains were grown on SP1 media (yeast nitrogen base with amino acids, tri-sodium citrate, glucose, xylose) under anaerobic conditions in serum bottles. Samples were taken and measured for ethanol, xylose and glucose concentrations over time (~65 hours)

(FIG. 8). Xylose Utilizing Strain 2 (XUS2) is engineered to utilize xylose. Strain XUS2-1 was adapted for improved growth on xylose originating from XUS2. Genome sequencing revealed mutations in iron-sulfur cluster related gene ISU1 in strain XUS2-1. Samples indicated as "+iron" were supplemented with iron at the start of the fermentation. The strains consumed all of the glucose at similar rates during the first ~18 hours of the fermentation and produced similar amounts of ethanol with no difference seen with the addition of iron. In contrast, the addition of iron significantly improved the rate of xylose utilization as seen in the increased ethanol production between 18 and 65 hours. The increased xylose utilization (and subsequent ethanol production) was seen for both strains with and without the mutations in the iron-sulfur cluster related genes.

Example 9—Iron Addition Enables Significant Activity of Xylose Isomerase in Vitro Xylose isomerase functions as a tetramer with the binding of two divalent cations per subunit essential for enzyme activity. $Mg^{2+}$, $Mn^{2+}$, $Co^{2+}$, and $Fe^{2+}$ ions activate the enzyme (Waltman et al. Protein Engineering, Design & Selection, 2014, p. 1-6). Using an in vitro enzymatic assay, the addition of $Fe^{2+}$ was found to result in significantly more xylose isomerase activity than the addition of $Mg^{2+}$ (FIG. 9). The protocol was essentially the same as described in Zou et al (Metabolic Engineering. 14, 2012, p. 611-622) with the exception of the use of three different buffers for the assay which varied in the absence or presence of the divalent metals $Mg^{2+}$ or $Fe^{2+}$. A cell extract was made from strain XUS1 which expresses the Bacteriodes thetaiotaomicron xylose isomerase. The cell extract was combined with Tris buffer +/− divalent metals, NADH, and sorbitol dehydrogenase. The assay was initiated with the addition of xylose and the reaction was monitored for 2 minutes at 340 nm to determine the initial rate. The reactions were performed under inert atmosphere and reducing conditions to deter oxidation of $Fe^{2+}$ to $Fe^{3+}$. One unit of activity is equal to 1umol NADH oxidized/min/ml, which corresponds directly with the consumption of the xylose that is added to initiate the reaction.

All documents cited herein, including journal articles or abstracts, published or corresponding U.S. or foreign patent applications, issued or foreign patents, or any other documents, are each entirely incorporated by reference herein, including all data, tables, figures, and text presented in the cited documents.

Following are particular embodiments of the disclosed invention

E1. A recombinant yeast cell comprising (a) at least one heterologous gene encoding a protein associated with iron metabolism and/or one or more mutations in one or more endogenous gene encoding a protein associated with iron metabolism; and (b) at least one heterologous gene encoding a polypeptide having xylose isomerase activity.

E2. The recombinant yeast cell of E1, wherein the at least one heterologous gene encoding a protein associated with iron metabolism and/or the one or more mutations in one or more endogenous gene encoding a protein associated with iron metabolism confers on the recombinant yeast cell an increased ability to utilize xylose as compared to a similar yeast cell lacking the one or more mutations.

E3. The recombinant yeast cell of E1 or E2, wherein the one or more mutations is a heterozygous mutation.

E4. The recombinant yeast cell of E1 or E2, wherein the one or more mutations is a homozygous mutation.

E5. The recombinant yeast cell of any one of E1-E4, wherein the recombinant yeast cell is a member of a genus selected from the group consisting of *Saccharomyces, Kluyveromyces, Candida, Pichia, Schizosaccharomyces, Hansenula, Kloeckera, Schwanniomyces,* and *Yarrowia*.

E6. The recombinant yeast cell of claim E5, wherein the recombinant yeast cell is a member of a species selected from the group consisting of *Saccharomyces cerevisiae, Saccharomyces bulderi, Saccharomyces exiguus, Saccharomyces uvarum, Saccharomyces diastaticus, Candida krusei, Kloeckera lactis, Kloeckera marxianus*, and *Kloeckera fragilis*.

E7. The recombinant yeast cell of claim E5, wherein the recombinant yeast cell is a member of a species selected from the group consisting of *Saccharomyces cerevisiae, Saccharomyces bulderi, Saccharomyces exiguus, Saccharomyces uvarum, Saccharomyces diastaticus, Kloeckera lactis, Kloeckera marxianus*, and *Kloeckera fragilis*.

E8. The recombinant yeast cell of any one of E1-E7, wherein the recombinant yeast cell is *S. cerevisiae*.

E9. The recombinant yeast cell of any one of E1-E4, wherein the one or more mutations in an endogenous gene is in a gene selected from the group consisting of ISU1, YFH1, NFS1, AFT1, AFT2, YAP5, FRA1, FRA2, GREX3, GREX4, CCC1, and any combination thereof.

E10. The recombinant yeast cell of E9, wherein the one or more mutations is a substitution of at least one nucleotide.

E11. The recombinant yeast cell of E10, wherein the recombinant yeast cell comprises one or more mutations in the endogenous ISU1 gene that results in a polypeptide comprising at least one amino acid substitution selected from the group consisting of D71N, D71G, and S98F, wherein the position of the substitution is relative to the amino acid positions of SEQ ID NO:29.

E12. The recombinant yeast cell of E10 or E11, wherein the recombinant yeast cell comprises one or more mutations in the endogenous YFH1 gene that results in a polypeptide comprising a T163P substitution, wherein the position of the substitution is relative to the amino acid positions of SEQ ID NO:31.

E13. The recombinant yeast cell of any one of E10-E12, wherein the recombinant yeast cell comprises one or more mutations in the endogenous NFS1 gene that results in a polypeptide comprising at least one amino acid substitution selected from the group consisting of L115W and E458D, wherein the position of the substitution is relative to the amino acid positions of SEQ ID NO:33.

E14. The recombinant yeast cell of any one of E9-E13, wherein the recombinant yeast cell comprises a mutation in the endogenous AFT1 gene that results in increased Aft1 activity.

E15. The recombinant yeast cell of any one of E9-E14, wherein the recombinant yeast cell comprises a mutation in the endogenous AFT2 gene that results in increased Aft2 activity.

E16. The recombinant yeast cell of any one of E9-E15, wherein the recombinant yeast cell comprises one or more mutations in one or more endogenous genes selected from FRA1, FRA2, GREX3, and GREX4; wherein the one or more mutations results in increased activity of Aft1 and/or Aft2; and/or wherein the one or more mutations results in increased expression of one or more genes regulated by Aft1 and/or Aft2.

E17. The recombinant yeast cell of E16, wherein the recombinant yeast cell further comprises a mutation in an endogenous gene selected from the group consisting of YAP5 and CCC1.

E18. The recombinant yeast cell of E17, wherein the recombinant yeast cell comprises a deletion or disruption of YAP5 or CCC1.

E19. The recombinant yeast cell of any one of E1-E18, wherein the heterologous gene (a) is selected from the group consisting of AFT1, AFT2, and orthologues and combinations thereof.

E20. The recombinant yeast cell of any one of E1-E18, wherein heterologous gene (a) encodes a protein that increases the activity of Aft1 and/or Aft2 and/or increases the expression of AFT1 and/or AFT2.

E21. The recombinant yeast cell of E18, wherein the heterologous gene (a) encodes a protein that suppresses or inhibits the activity and/or expression of a protein that suppresses or inhibits the activity of Aft1 and/or Aft2 and/or suppresses or inhibits the expression of AFT1 and/or AFT2.

E22. The recombinant yeast cell of any one of E1-E18, wherein the heterologous gene (a) encodes a target of Aft1 and/or Aft2.

E23. The recombinant yeast cell of any one of E1-E18, wherein the heterologous gene (a) encodes a polypeptide having iron transport activity.

E24. The recombinant yeast cell of any one of E1-E23, wherein the heterologous gene (a) is constitutively expressed.

E25. The recombinant yeast cell of any one of E1-E24, wherein the heterologous gene (b) encodes a xylose isomerase enzyme.

E26. The recombinant yeast cell of E25, wherein the heterologous gene (b) encodes a polypeptide having at least 80% sequence identity with an amino acid sequence selected from the group consisting of SEQ ID NOs: 1, 3, 5, 7, 9, 11, 13, 15, 17, 19, 21, 23, 25, 27, 35, 37, 39, and 41.

E27. The recombinant yeast cell of E25, wherein the heterologous gene (b) encodes a polypeptide having at least 80% sequence identity with an amino acid sequence selected from the group consisting of SEQ ID NOs: 1, 3, 5, 7, 9, 11, 13, 15, 17, 19, 21, 23, 25, and 27.

E28. The recombinant yeast cell of E26, wherein the heterologous gene (b) encodes a polypeptide having at least 85% sequence identity with an amino acid sequence selected from the group consisting of SEQ ID NOs: 1, 3, 5, 7, 9, 11, 13, 15, 17, 19, 21, 23, 25, 27, 35, 37, 39, and 41.

E29. The recombinant yeast cell of E27, wherein the heterologous gene (b) encodes a polypeptide having at least 85% sequence identity with an amino acid sequence selected from the group consisting of SEQ ID NOs: 1, 3, 5, 7, 9, 11, 13, 15, 17, 19, 21, 23, 25, and 27.

E30. The recombinant yeast cell of E28, wherein the heterologous gene (b) encodes a polypeptide having at least 90% sequence identity with an amino acid sequence selected from the group consisting of SEQ ID NOs: 1, 3, 5, 7, 9, 11, 13, 15, 17, 19, 21, 23, 25, 27, 35, 37, 39, and 41.

E31. The recombinant yeast cell of E29, wherein the heterologous gene (b) encodes a polypeptide having at least 90% sequence identity with an amino acid sequence selected from the group consisting of SEQ ID NOs: 1, 3, 5, 7, 9, 11, 13, 15, 17, 19, 21, 23, 25, and 27.

E32. The recombinant yeast cell of E30, wherein the heterologous gene (b) encodes a polypeptide having at least 95% sequence identity with an amino acid sequence selected from the group consisting of SEQ ID NOs: 1, 3, 5, 7, 9, 11, 13, 15, 17, 19, 21, 23, 25, 27, 35, 37, 39, and 41.

E33. The recombinant yeast cell of E31, wherein the heterologous gene (b) encodes a polypeptide having at least 95% sequence identity with an amino acid sequence selected from the group consisting of SEQ ID NOs: 1, 3, 5, 7, 9, 11, 13, 15, 17, 19, 21, 23, 25, and 27.

E34. The recombinant yeast cell of E32, wherein the heterologous gene (b) encodes a polypeptide having 100% sequence identity with an amino acid sequence selected from the group consisting of SEQ ID NOs: 1, 3, 5, 7, 9, 11, 13, 15, 17, 19, 21, 23, 25, 27, 35, 37, 39, and 41.

E35. The recombinant yeast cell of E33, wherein the heterologous gene (b) encodes a polypeptide having 100% sequence identity with an amino acid sequence selected from the group consisting of SEQ ID NOs: 1, 3, 5, 7, 9, 11, 13, 15, 17, 19, 21, 23, 25, and 27.

E36. The recombinant yeast cell of any one of E1-E35, wherein the recombinant yeast cell further comprises at least one genetic modification of one or more endogenous genes encoding a protein of the pentose phosphate pathway.

E37. The recombinant yeast cell of E36, wherein the recombinant yeast cell comprises at least one genetic modification in at least one of the endogenous genes selected from the group consisting of XKS1, RKI1, RPE1, TKL1, and TAL1.

E38. The recombinant yeast cell of E37, wherein the recombinant yeast cell comprises one or more genetic modifications that leads to the overexpression of at least one of the endogenous genes selected from the group consisting of XKS1, RKI1, RPE1, TKL1, and TAL1.

E39. The recombinant yeast cell of any one of E1-E38, wherein the recombinant yeast cell further comprises a deletion or disruption of one or more aldose reductase genes.

E40. The recombinant yeast cell of E39, wherein the aldose reductase gene is GRE3 or YPR1.

E41. The recombinant yeast cell of E40, wherein the recombinant yeast cell comprises a deletion or disruption of GRE3 and YPR1.

E42. The recombinant yeast cell of any one of E1-E41, wherein the yeast cell further comprises a modification of the endogenous PGM1 gene.

E43. The recombinant yeast cell of E42, wherein the modification of the endogenous PGM1 gene results in the overexpression of PGM1.

E44. The recombinant yeast cell of any one of E1-E43, wherein the recombinant yeast cell is capable of growing on xylose as the sole carbon source.

E45. A method for producing a fermentation product comprising contacting the recombinant yeast cell of any one of E1-E44 with a carbon source, wherein said carbon source comprises xylose and/or xylan.

E46. A method for producing a fermentation product comprising contacting the recombinant yeast cell of any one of E1-E44 with a carbon source, wherein said carbon source comprises xylose.

E47. The method of E45, wherein the recombinant yeast cell is further grown on a media supplemented with iron.

E48. The method of E45 or E46, wherein the fermentation product is selected from the group consisting of ethanol, lactic acid, 3-hydroxy-propionic acid, hydrogen, butyric acid, acrylic acid, acetic acid, succinic acid, citric acid, malic acid, fumaric acid, an amino acid, 1,3-propane-diol, ethylene, glycerol, acetone, isopropyl alcohol, butanol, a β-lactam, an antibiotic, a cephalosporin, and combinations thereof.

E49. The method of E47, wherein the fermentation product is ethanol.

E50. The method of any one of E45-E48, further comprising recovering the fermentation product.

E51. A method of producing ethanol comprising contacting a carbon source comprising xylose and/or xylan with the recombinant yeast cell of any one of E1-E44 in a fermentation medium under conditions wherein ethanol is produced.

E52. A method of producing ethanol comprising contacting a carbon source comprising xylose with the recombinant yeast cell of any one of E1-E44 in a fermentation medium under conditions wherein ethanol is produced.

E53. The method of E50, wherein the fermentation medium is supplemented with iron.

E54. The method of E50 or E51, wherein the carbon source comprises cellulosic or lignocellulosic biomass.

E55. The method of E52, wherein the cellulosic or lignocellulosic biomass is selected from the group consisting of insoluble cellulose, crystalline cellulose, pretreated hardwood, paper sludge, pretreated corn stover, pretreated sugar cane bagasse, pretreated corn cobs, pretreated switchgrass, pretreated municipal solid waste, pretreated distiller's dried grains, pretreated wheat straw, corn fiber, agave, trees, corn stover, wheat straw, sugar cane bagasse, switchgrass, and combinations thereof.

E56. The method of E53, wherein the biomass is corn stover.

E57. The method of claim any one of E50-E54, further comprising recovering the ethanol.

E58. The recombinant yeast cell of any one of E1-E44 for use in a fermentation which convert a carbon source into a fermentation product, wherein said carbon source comprises xylose and/or xylan.

E59. The recombinant yeast cell of E35, wherein the recombinant yeast cell comprises heterologous expression of one or more polynucleotides encoding XKS1, RKI1, RPE1, TKL1, and/or TAL1.

Those skilled in the art will recognize, or be able to ascertain using no more than routine experimentation, many equivalents to the specific embodiments of the invention described herein. Such equivalents are intended to be encompassed by the following claims.

The invention claimed is:

1. A recombinant yeast cell comprising (a) at least one heterologous gene encoding a protein associated with iron metabolism; and (b) at least one heterologous gene encoding a polypeptide having xylose isomerase activity, wherein the heterologous gene (b) encodes a polypeptide having at least 80%, 85%, 90%, 95% or 100% sequence identity with an amino acid sequence selected from the group consisting of SEQ ID NOs: 1, 3, 5, 7, 9, 11, 13, 15, 17, 19, 21, 23, 25, 27, 35, 37, 39 and 41.

2. The recombinant yeast cell of claim 1, wherein the heterologous gene (a) is selected from the group consisting of AFT1, AFT2, and orthologues and combinations thereof.

3. The recombinant yeast cell of claim 1, wherein heterologous gene (a) encodes a protein that increases the activity of Aft1 and/or Aft2 and/or increases the expression of AFT1 and/or AFT2 and/or suppresses or inhibits the activity and/or expression of a protein that suppresses or inhibits the activity of Aft1 and/or Aft2 and/or suppresses or inhibits the expression of AFT1 and/or AFT2.

4. The recombinant yeast cell of claim 1, wherein the heterologous gene encodes a target of Aft1 and/or Aft2.

5. The recombinant yeast cell of claim 1, wherein the heterologous gene (a) encodes a polypeptide having iron transport activity.

6. The recombinant yeast cell of claim 1, the recombinant yeast cell further comprises one or more mutations in one or more endogenous genes encoding a protein associated with iron metabolism.

7. The recombinant yeast cell of claim 6, wherein the one or more mutations in one ore more endogenous genes is in a gene of ISU1, YFH1, NFS1, AFT1, AFT2, YAP5, FRA1, FRA2, GREX3, GREX4, CCC1, or any combination thereof.

8. The recombinant yeast cell of claim 6, wherein the recombinant yeast cell comprises one or more mutations in the endogenous ISU1 gene that results in a polypeptide comprising at least one amino acid substitution selected from the group consisting of D71N, D71G, and S98F, wherein the position of the substitution is relative to the amino acid positions of SEQ ID NO:29.

9. The recombinant yeast cell of claim 6, wherein the recombinant yeast cell comprises one or more mutations in the endogenous YFH1 gene that results in a polypeptide comprising a T163P substitution, wherein the position of the substitution is relative to the amino acid positions of SEQ ID NO:31.

10. The recombinant yeast cell of claim 6, wherein the recombinant yeast cell comprises one or more mutations in the endogenous NFS1 gene that results in a polypeptide comprising at least one amino acid substitution selected from the group consisting of L115W and E458D, wherein the position of the substitution is relative to the amino acid positions of SEQ ID NO:33.

11. The recombinant yeast cell of claim 6, wherein the recombinant yeast cell comprises a mutation in the endogenous AFT1 gene that results in increased Aft1 activity and/or a mutation in the endogenous AFT2 gene that results in increased Aft2 activity.

12. The recombinant yeast cell of claim 6, wherein the recombinant yeast cell comprises one or more mutations in one or more endogenous genes FRA1, FRA2, GREX3, or GREX4; wherein the one or more mutations results in increased activity of Aft1 and/or Aft2; and/or wherein the one or more mutations results in increased expression of one or more genes regulated by Aft1 and/or Aft2.

13. The recombinant yeast cell of claim 6, wherein the recombinant yeast cell further comprises a mutation in an endogenous gene selected from the group consisting of YAP5 and CCC1.

14. The recombinant yeast cell of claim 1, wherein the recombinant yeast cell further comprises at least one genetic modification of one or more endogenous genes encoding a protein of the pentose phosphate pathway.

15. The recombinant yeast cell of claim 14, wherein the recombinant, yeast cell comprises at least one genetic modification in at least one of the endogenous genes selectec the group consisting of XKS1, RKI1, RPE1, TKL1, and TAL1.

16. The recombinant yeast cell of claim 1, wherein the recombinant yeast cell further comprises a deletion or disruption of one or more aldose reductase genes.

17. The recombinant yeast cell of claim 16, wherein the aldose reductase gene is GRE3 or YPR1.

18. The recombinant yeast cell of any one of claim 17, wherein the yeast cell further comprises a modification of the endogenous PGM1 gene.

19. The recombinant yeast cell of claim 1, wherein the recombinant yeast cell comprises heterologous expression of one or more polynucleotides encoding XKS1, RKI1, RPE1, TKL1, and/or TAL1.

20. The recombinant yeast cell of claim 1, wherein the heterologous gene (b) encodes a polypeptide having at least 80% sequence identity with an amino acid sequence selected from the group consisting of SEQ ID NOs: 1, 3, 5, 7, 9, 11, 13, 15, 17, 19, 21, 23, 25, and 27.

21. A method for producing a fermentation product comprising contacting the recombinant yeast cell of claim 1 with a carbon source, wherein said carbon source comprises xylose and/or xylan.

\* \* \* \* \*

UNITED STATES PATENT AND TRADEMARK OFFICE
CERTIFICATE OF CORRECTION

PATENT NO. : 10,465,181 B2
APPLICATION NO. : 15/884449
DATED : November 5, 2019
INVENTOR(S) : Allan C. Froehlich et al.

It is certified that error appears in the above-identified patent and that said Letters Patent is hereby corrected as shown below:

In the Claims

At Column 115, Claim number 4, Line number 2, please add "(a)" after "gene"

At Column 115, Claim number 7, Line number 2, please change "ore" to "or"

At Column 117, Claim number 15, Line number 3, please change "selectec" to "selected from"

Signed and Sealed this
Twenty-fourth Day of December, 2019

Andrei Iancu
*Director of the United States Patent and Trademark Office*